(12) United States Patent
Bunch et al.

(10) Patent No.: US 6,924,099 B1
(45) Date of Patent: Aug. 2, 2005

(54) BIOMARKERS AND ASSAYS FOR CARCINOGENESIS

(75) Inventors: Roderick T Bunch, Mt. Prospect, IL (US); Dale L Morris, Ballwin, MO (US); Sandra W. Curtiss, Ellisville, MO (US); Charles P. Rodi, Del Mar, CA (US)

(73) Assignee: G.D. Searle & Co., St. Louis, MO (US)

( * ) Notice: Subject to any disclaimer, the term of this patent is extended or adjusted under 35 U.S.C. 154(b) by 0 days.

(21) Appl. No.: 09/490,609

(22) Filed: Jan. 25, 2000

Related U.S. Application Data

(60) Provisional application No. 60/118,078, filed on Jan. 29, 1999.

(51) Int. Cl.[7] .......................... C12Q 1/68; C12P 19/34; C07H 21/02; C07H 21/04
(52) U.S. Cl. .................. 435/6; 435/91.1; 435/91.2; 435/91.21; 536/23.1; 536/24.3; 536/24.31; 536/24.33; 536/23.5
(58) Field of Search .................. 435/6, 91.1, 91.2, 435/91.21; 536/23.1, 24.3, 24.31, 24.33, 23.5

(56) References Cited

U.S. PATENT DOCUMENTS 5,958,690 A * 9/1999 Hillman et al. ............... 435/6
6,451,524 B1 * 9/2002 Ecker .......................... 435/6

OTHER PUBLICATIONS

Murata, T. et al. Mol. Cell Biochem. vol. 175, pp. 163–168 (1997).*
Makino, R. et al. Molecular and Cell. Biochem. vol. 155, pp. 85–90 (1996).*
Radek C. Skoda et al., Human Microsomal Xenobiotic Epoxide Hydrolase, The Journal of Biological Chemistry, vol. 263, No. 3, Jan. 25, 1988, pp. 1549–1554.*
Leigh Anderson et al., A comparison of selected mRNA and protein abundances in human liver, Electrophoresis (1997) 18. pp. 533–537.*
Norman H. Lee et al., Comparative expressed–sequence–tag analysis of differential gene expression profiles in PC–12 cells before and after nerve growth factor treatment, Proc. Natl. Acad. Sci. USA, vol. 92, pp. 8303–8307 (1995).*

* cited by examiner

*Primary Examiner*—John L. LeGuyader
*Assistant Examiner*—Jane Zara
(74) *Attorney, Agent, or Firm*—Harness, Dickey & Pierce, PLC

(57) ABSTRACT

The present invention relates to carcinogenesis biomarkers produced by phenobarbital-treated rat hepatocytes, nucleic acid molecules that encode carcinogenesis biomarkers or a fragment thereof and nucleic acid molecules that are useful as probes or primers for detecting or inducing carcinogenesis, respectively. The invention also relates to applications of the factor or fragment such as forming antibodies capable of binding the carcinogenesis biomarkers or fragments thereof.

6 Claims, 1 Drawing Sheet

Comparison of mRNA Levels of Differentially
Expressed Transcripts: Taqman (2- and 13-wk samples)
versus AFLP (13 wk)

BIOMARKERS AND ASSAYS FOR CARCINOGENESIS

This application is a continuation-in-part of U.S. provisional application Ser. No. 60/118,078, filed on Jan. 29, 1999, the contents of which are hereby incorporated herein.

FIELD OF THE INVENTION

The present invention relates to genes differentially regulated by phenobarbital, nucleic acid molecules or fragments thereof that act as biomarkers for carcinogenesis, and nucleic acid molecules that are useful as probes or primers for detecting or inducing carcinogenesis, respectively. The invention also relates to applications such as forming antibodies capable of binding carcinogenesis biomarkers or fragments thereof.

BACKGROUND

In the field of toxicology, high resolution assays now make it possible to discover differences in gene expression brought on by exposure to a particular xenobiotic. Such high-throughput, high-resolution molecular biology methods can be used to determine virtually all toxicant-induced changes in gene expression. A catalog of toxicant-induced gene expression changes would be useful to better predict animal toxicity in order to reduce costs, timelines and animal use by enhancing the probability that product candidates chosen for further development will pass regulatory testing requirements. Such a catalog would also enable scientists to better predict human toxicity, resulting in fewer compounds failing in clinical trials while better safeguarding human health.

The basis for these types of investigations is the expectation that toxicological endpoints (e.g. tumor formation) are the result of earlier molecular events. For example, by creating a catalog of changes in rat liver gene expression following treatment with phenobarbital, one can test whether early gene expression is as predictive as later readouts in assessing the nongenotoxic carcinogenicity of this compound in rats.

The power of transcriptional genomic analyses is that they can measure changes in the expression of thousands of genes, and a comprehensive catalog of expression changes can be envisioned. Using the same catalog of changes, other known nongenotoxic carcinogens (NGCs) could be assessed, as well as compounds known not to be NGCs in rats. Analysis of correlations between the changes and carcinogenesis, as well as analysis of the biological significance of the genes, should indicate whether there are specific genes or gene-expression patterns that predict carcinogenesis. Thus, there is a need in the art for catalogs or panels of predictive markers. Such panels of expressed genes would allow one to examine a greater number of candidate compounds in a shorter period of time prior to selecting a lead compound for traditional testing. As a result of this screening approach, the success rate of compounds in pre-clinical trials should improve dramatically.

These panels of predictive markers could also be used to assess the use of primary rat hepatocytes in high-throughput cell-based assays of toxicity and carcinogenicity. This would further increase the number of compounds that could be assessed, perhaps to the point where entire compound libraries could be assayed, and scores for potential toxicities could be created for each compound. Further, parallel analyses using both animal and human genes could be used to correlate the results from pre-clinical in vivo and in vitro data (using both cultured animal and cultured human cells) with human clinical data to create assays that better predict human toxicity.

SUMMARY OF THE INVENTION

It is an object of the present invention to provide a catalog or panel of changes in ene expression that are predictive of carcinogenicity. The catalogs includes substantially-purified nucleic acid sequences that have been discovered. In one embodiment, the present invention relates to a substantially-purified nucleic acid molecule comprising a nucleic acid sequence selected from the group consisting of SEQ NO: 1 through SEQ NO: 580 or fragments, substantial homologues, and substantial complements thereof.

In another embodiment, the present invention relates to a substantially-purified carcinogenesis biomarker or fragment thereof encoded by a first nucleic acid molecule which substantially hybridizes to a second nucleic acid molecule, the second nucleic acid molecule comprising a nucleic acid sequence selected from the group consisting of SEQ NO: 1 through SEQ NO:580 and complements thereof.

It is another object of the present invention to provide an assay for toxicity to predict the carcinogenicity of a composition. In a further embodiment, the present invention relates to a method for measuring the carcinogenicity of a composition comprising exposing a mammal to the composition; and determining the presence or absence of mRNA which substantially hybridizes to a nucleic acid sequence selected from the group consisting of SEQ NO: 1 through SEQ NO:580 and complements thereof.

It is a further object of the present invention to provide a quantitative and qualitative method of detection of carcinogenesis-related proteins or peptides of the present invention. In one embodiment, antibodies, proteins, peptides, or fusion proteins that specifically bind to one or more of the proteins encoded by the nucleic acid molecules of the present invention can be used to measure the cacinogenesis-related proteins.

Various other objects and advantages of the present invention will become apparent from the following figures and description of the invention.

DETAILED DESCRIPTION OF THE INVENTION

A. General Concepts and Definitions

Figure 1:
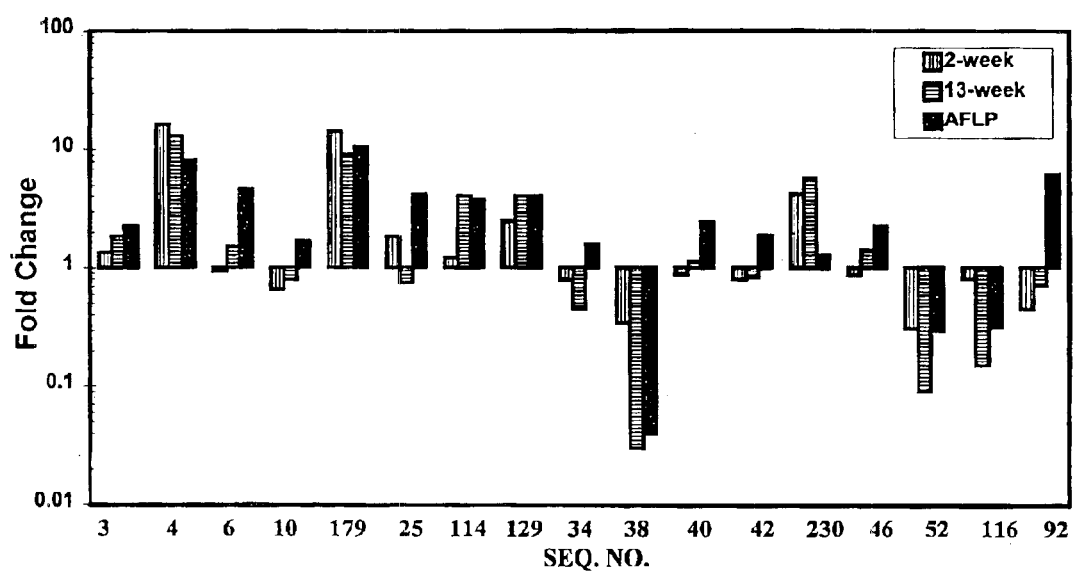
FIG. 1 shows a comparison of mRNA levels of differentially expressed transcripts.

These detailed descriptions are presented for illustrative purposes only and are not intended as a restriction on the scope of the invention. Rather, they are merely some of the embodiments that one skilled in the art would understand from the entire contents of this disclosure. All parts are by weight and temperatures are in Degrees centigrade unless otherwise indicated.

Abbreviations and Definitions

The following is a list of abbreviations and the corresponding meanings as used interchangeably herein:

IMDM=Iscove's modified Dulbecco's media
mg=milligram
ml or mL=milliliter
μg or ug=microgram
μl or ul=microliter
ODNs=oligonucleotides
PCR=polymerase chain reaction RP-HPLC=reverse phase high performance liquid chromatography The following is a list definitions of various terms used herein:

The tem "altered" means that expression differs from the expression response of cells or tissues not exhibiting the phenotype.

The term "amino acid(s)" means all naturally occurring 1.-amino acids.

The term "biologically active" means activity with respect to either a structural or a catalytic attribute, which includes the capacity of a nucleic acid to hybridize to another nucleic acid molecule, or the ability of a protein to be bound by an antibody (or to compete with another molecule for such binding), among others. Catalytic attributes involve the capacity of the agent to mediate a chemical reaction or response.

The term "cluster" means that BLAST scores from pairwise sequence comparisons of the member clones are similar enough to be considered identical with experimental error.

The term "complement" means that one nucleic acid exhibits complete complementarity with another nucleic acid.

The term "complementarity" means that two molecules can hybridize to one another with sufficient stability to permit them to remain annealed to one another under conventional high stingency conditions.

The term "complete complementarity" means that every nucleotide of one molecule is complementary to a nucleotide of another molecule.

The term "degenerate" means that two nucleic acid molecules encode for the same amino acid sequences but comprise different nucleotide sequences (see U.S. Pat. No. 4,757,006).

The term "exogenous genetic material" means any genetic material, whether naturally occurring or otherwise, from any source that is capable of being inserted into any organism.

The term "expression response" means the mutation affecting the level or pattern of the expression encoded in part or whole by one or more nucleic acid molecules.

The term "fragment" means a nucleic acid molecule whose sequence is shorter than the target or identified nucleic acid molecule and having the identical, the substantial complement, or the substantial homologue of at least 7 contiguous nucleotides of the target or identified nucleic acid molecule.

The term "fusion protein" means a protein or fragment thereof that comprises one or more additional peptide regions not derived from that protein. Such molecules may be derivatized to contain carbohydrate or other moieties (such as keyhole limpet hemocyanin, etc.).

The term "hybridization probe" means any nucleic acid capable of being labeled and forming a double-stranded structure with another nucleic acid over a region large enough for the double stranded structure to be detected.

The term "isolated" means an agent is separated from another specific component with which it occurred. For example, the isolate material may be purified to essential homogeneity, as determined by PAGE or column chromatography, such as HPLC. An isolated nucleic acid can comprise at least about 50, 80, or 90% (on a molar basis) of all macromolecular species present. Some of these methods described later lead to degrees of purification appropriate to identify single bands in electrophoresis gels. However, this degree of purification is not required.

The term "marker nucleic acid" means a nucleic acid molecule that is utilized to determine an attribute or feature (e.g., presence or absence, location, correlation, etc.) of a molecule, cell, or tissue.

The term "mimetic" refers to a compound having similar functional and/or structural properties to another known compound or a particular fragment of that known compound.

The term "minimum complementarity" means that two molecules can hybridize to one another with sufficient stability to permit them to remain annealed to one another under at least conventional low stringency conditions.

The term "PCR probe" means a nucleic acid capable of initiating a polymerase activity while in a double-stranded structure with another nucleic acid. For example, Krzesicki, et al., Am. J. Respir. Cell Mol. Biol. 16:693–701 (1997), incorporated by reference in its entirety, discusses the preparation of PCR probes for use in identifying nucleic acids of osteoarthrits tissue. Other methods for determining the structure of PCR probes and PCR techniques have been described.

The term "phenotype" means any of one or more characteristics of an organism, tissue, or cell.

The term "polymorphism" means a variation or difference in the sequence of the gene or its flanking regions that arises in some of the members of a species.

The term "primer" means a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template.

The term "probe" means an agent that is utilized to determine an attribute or feature (e.g. presence or absence, location, correlation, etc.) of a molecule, cell, tissue, or organism.

The term "product score" refers to a formula which indicates the strength of a BLAST match using the fraction of overlap of two sequences and the percent identity. The formula is as follows:

$$\text{Product Score} = \frac{\text{BLAST Score} \times \text{Percent Identity}}{5 \times \text{minimum}\{\text{length}(\text{Seq1}), \text{length}(\text{Seq2})\}}$$

The term "promoter region" means a region of a nucleic acid that is capable, when located in cis to a nucleic acid sequence that encodes for a protein or peptide, of functioning in a way that directs expression of one or more mRNA molecules.

The term "protein fragment" means a peptide or polypeptide molecule whose amino acid sequence comprises a subset of the amino acid sequence of that protein.

The term "protein molecule/peptide molecule" means any molecule that comprises five or more amino acids.

The term "recombinant" means any agent (e.g., DNA, peptide, etc.), that is, or results from, however indirectly, human manipulation of a nucleic acid molecule. The recombination may occur inside a cell or in a tube.

The term "selectable marker" means a gene who's expression can be detected by a probe as a means of identifying or selecting for transformed cells.

The term "specifically bind" means that the binding of an antibody or peptide is not competitively inhibited by the presence of non-related molecules.

The term "specifically hybridizing" means that two nucleic acid molecules are capable of forming an anti-parallel, double-stranded nucleic acid structure.

The term "substantial complement" means that a nucleic acid sequence shares at least 80% sequence identity with the complement.

The term "substantial fragment" means a fragment which comprises at least 100 nucleotides.

The term "substantial homologue" means that a nucleic acid molecule shares at least 80% sequence identity with another.

The term "substantial identity" means that 70% to about 99% of a region or fragment in a molecule is identical to a region of a different molecule. When the individual units (e.g. nucleotides or amino acids) of the two molecules are schematically positioned to exhibit the highest number of units in the same position over a specific region, a percentage identity of the units identical over the total number of units in the region is determined. Numerous algorithmic and computerized means for determining a percentage identity are known in the art. These means may allow for gaps in the region being considered in order to produce the highest percentage identity.

The term "substantially hybridizes" means that two nucleic acid molecules can form an anti-parallel, double-stranded nucleic acid structure under conditions (e.g. salt and temperature) that permit hybridization of sequences that exhibit 90% sequence identity or greater with each other and exhibit this identity for at least a contiguous 50 nucleotides of the nucleic acid molecules.

The term "substantially purified" means that one or more molecules that are or may be present in a naturally occurring preparation containing the target molecule will have been removed or reduced in concentration.

AGENTS OF THE INVENTION

A. Nucleic Acid Molecules

The present invention relates to nucleic acid sequences selected from the group consisting of SEQ NO:1 through SEQ NO: 580, substantial fragments thereof, substantial homologues thereof, and substantial complements thereof. By creating a catalog of changes in rat liver gene expression following treatment with phenobarbital, substantially-purified nucleic acid sequences selected from the group consisting of SEQ NO: 1 through SEQ NO: 580 have been discovered. These sequences are useful as biomarkers of carcinogenesis.

The present invention also relates to nucleic acid sequences derived from the one or more sequences identified in SEQ NOS:1–580. Fragment nucleic acids may encompass significant portion(s) of, or indeed most of, these sequences. For example, a fragment nucleic acid can encompass an carcinogens biomarker gene homolog or fragment thereof. Alternately, the fragments may comprise smaller oligonucleotides, for example an oligonucleotide having from about 10 to about 250 nucleotides or from about 15 to about 30 nucleotide.

A variety of computerized means for identifying sequences derived from the SEQ NO.: 1–580 exists. These include the five implementations of BLAST, three designed for nucleotide sequences queries (BLASTN, BLASTX, and TBLASTX) and two designed for protein sequence queries (BLASTP and TBLASTN), as well as FASTA and others (Coulson, *Trends in Biotechnology* 12:76–80 (1994); Birren et al., *Genome Analysis* 1:543–559 (1997)). Other programs which use either individual sequences or make models from related sequences to further identify sequences derived from SEQ NO 1–SEQ NO 580 exist. Model building and searching programs includes HMMer (Eddy), MEME (Bailey and Elkan, *Ismb* 3: 21–29(1995)) and PSI-BLAST (Altschul et al., *Nucleic Acids Res* 25: 3389–3402 (1997)). Another set of programs which use predicted, related, or known protein structures to further identify sequences derived from SEQ NO 1–SEQ NO 580 exists. Structure-based searching programs includes ORF and PROSITE. Other programs which use individual sequences or related groups of sequences relying on pattern discovery to further identify sequences derived from SEQ NO:1–580 exist. Pattern recognition programs include Teiresias (Rigoutsos, I. and A. Floratos, *Bioinformatics* 1: (1998)). These programs can search any appropriate database, such as GenBank, dbEST, EMBL, SwissProt, PIR, and GENES. Furthermore, computerized means for designing modifications in protein structure are also known in the art (Dahiyat and Mayo, *Science* 278:82–87 (1997)).

Nucleic acids or fragments thereof of the present invention are capable of specifically hybridizing to other nucleic acids under certain circumstances. The present invention further relates to nucleic acid sequences that will specifically hybridize to one or more of the nucleic acids set forth in SEQ NO: 1 through SEQ NO: 580, or complements thereof, under moderately stringent conditions, for example at about 2.0×SSC and about 65° C. Alternatively, the nucleic acid sequences of the present invention may specifically hybridize to one or more of the nucleic acids set forth in SEQ NO:1 through SEQ NO: 580, or complements thereof, under high stringency conditions.

The present invention also relates to nucleic acid sequences that share between 100% and 90% sequence identity with one or more of the nucleic acid sequences set forth in SEQ NO: 1 through to SEQ NO: 580 or complements thereof. In a further aspect of the invention, nucleic acid sequences of the invention share between 100% and 95% sequence identity with one or more of the nucleic acid sequences set forth in SEQ NO: 1 through SEQ NO: 580, or complements thereof. Alternatively, nucleic acid sequences of the present invention may share between 100% and 98% or between 100% and 99% sequence identity with one or more of the nucleic acid sequences set forth in SEQ NO: 1 through SEQ NO: 580, or complements thereof.

A region or fragment in a molecule with "substantial identity" to a region of a different molecule can be represented by a ratio. In a preferred embodiment, a 10 nucleotide in length nucleic acid region or fragment of the invention has a percentage identity of about 70% to about 99% with a nucleic acid sequence existing within one of SEQ NO.: 1–580 or a complement of SEQ NO.: 1–580.

The invention also provides a computer-readable medium having recorded thereon the sequence information of one or more of SEQ NO:1 through SEQ NO:580, or complements thereof. In addition, the invention provides a method of identifying a nucleic acid comprising providing a computer-readable medium of the invention and comparing nucleotide sequence information using computerized means.

i. Nucleic Acid Primers and Probes

The present invention also relates to nucleic acid primers and probes derived from the nucleic acid sequences set forth in SEQ NO: 1 through SEQ NO: 580. The nucleic acid primers and probes of the invention may be derived from the disclosed sequences, such as a fragment of 10 nucleotides or more or a sequence with 70% to 99% identity to a fragment of at least 10 nucleotides. Numerous methods for defining or identifying primers and probes for nucleic acid or sequence based analysis exist. Examples of suitable primers include, but are not limited to, the nucleic acid sequences set forth in SEQ NO: 519 through SEQ NO: 580. Examples of 5' primers (from the 5' to 3' direction) include, but are not limited to, SEQ NO: 550–580. Examples of 3' primers (from the 5' to 3' direction) include, but are not limited to, SEQ NO: 519–549. Examples of suitable probes include, but are not limited to, the nucleic acid sequences set forth in SEQ NO: 490 through SEQ NO: 518. The genes that corresponds to the primer and probe sequences (SEQ NO: 490–580) are described in Table 7.

Conventional stringency conditions are described by Sambrook, et al., *Molecular Cloning, A Laboratory Manual*, 2nd Ed., Cold Spring Harbor Press, Cold Spring Harbor, N.Y. (1989), and by Haymes, et al. *Nucleic Acid Hybridization, A Practical Approach*, IRL Press, Washington, D.C. (1985), the entirety of both is herein incorporated by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in Ausubel, et al., *Current Protocols in Molecular Biology*, John Wiley & Sons, N.Y. (1989) (see especially sections 6.3.1–6.3.6). [This reference and the supplements through January 2000 are specifically incorporated herein by reference and can be relied to make or use any embodiment of the invention.] For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Temperature and salt conditions may be varied independently.

Primers and probes of the present invention can be used in hybridization assays or techniques, in a variety of PCR-type methods, or in computer-based searches of databases containing biological information. Exemplary methods include a method of identifying a nucleic acid which comprises the hybridization of a probe of the invention with a sample containing nucleic acid and the detection of stable hybrid nucleic acid molecules. Also included are methods of identifying a nucleic acid comprising contacting a PCR probe of the invention with a sample containing nucleic acid and producing multiple copies of a nucleic acid that hybridizes, or is at least minimally complementary to the PCR probe.

The primers and probes of the invention may be labeled with reagents that facilitate detection (e.g. fluorescent labels. Prober et al. Science 238: 336–340 (1987). Albarella et al. EP 144914: chemical labels. Sheldon et al. U.S. Pat. No. 4,582,789. Albarella et al. U.S. Pat. No. 4,563,417: and modified bases. Miyoshi et al. EP 119448) all of which are incorporated by reference in their entirety)).

ii. Nucleic Acids Comprising Genes, Fragments, or Homologs Thereof

This invention also provides genes corresponding to the cDNA sequences disclosed herein, also called carcinogenesis biomarkers. The corresponding genes can be isolated in accordance with known methods using the sequence information disclosed herein. The methods include the preparation of probes or primers from the disclosed sequence information for identification and/or amplification of genes in appropriate genomic libraries or other sources of genomic materials.

In another preferred embodiment, nucleic acid molecules having SEQ NO: 1 through SEQ NO: 580, or complements and fragments of either, can be utilized to obtain homologues equivalent to the naturally existing homologues.

In a further aspect of the present invention, one or more of the nucleic acid molecules of the present invention differ in nucleic acid sequence from those encoding a homologue or fragment thereof in SEQ NO: 1 through SEQ NO: 580, or complements thereof, due to the degeneracy in the genetic code in that they encode the same protein but differ in nucleic acid sequence. In another further aspect of the present invention, one or more of the nucleic acid molecules of the present invention differ in nucleic acid sequence from those encoding an homologue of fragment thereof in SEQ NO: 1 through SEQ NO:580, or complements thereof, due to fact that the different nucleic acid sequence encodes a protein having one or more conservative amino acid residue. Examples of conservative substitutions are set forth below. Codons capable of coding for such conservative substitutions are well known in the art.

| Original Residue | Conservative Substitutions |
|---|---|
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Genomic sequences can be screened for the presence of protein homologues utilizing one or a number of different search algorithms have that been developed, such as the suite of BLAST programs. The BLASTX program allows the comparison of nucleic acid sequences in this invention to protein databases.

In a preferred embodiment of the present invention, the homologue protein or fragment thereof exhibits a BLASTX probability score of less than 1E-30, alternatively a BLASTX probability score of between about 1 E-30 and about 1 E-12 or a BLASTX probability score of greater than 1 E-12 with a nucleic acid or gene of this invention. In another preferred embodiment of the present invention, the nucleic acid molecule encoding the gene homologue or fragment thereof exhibits a % identity with its homologue of between about 25% and about 40%, or alternatively between about 40% and about 70%, or from 70% and about 90%, or from about 90% and 99%. In another embodiment, the gene homologue or fragment has a single nucleotide difference from its homologue.

The resulting product score of a BLAST program ranges from 0 to 100, with 100 indicating 100% identity over the entire length of the shorter of the two sequences, and 0 representing no shared identity between the sequences. The homologue protein or fragment thereof may also exhibit a product score of 100. Alternatively, the product score is between about 49 and about 99. The protein or fragment may also exhibit a product score of 0. Alternatively, the homolog or fragment exhibits a product score between about 1 and about 49.

The sequences of the present invention were searched for sequence similarity and given biological annotations based on that similarity.

Table 1: Sequences down-regulated at least 1.7-fold by 13 weeks of treatment with phenobarbitol are shown with their corresponding annotation.

Table 2: Sequences up-regulated at least 1.7-fold by 13 weeks of treatment with phenobarbitol are shown with their corresponding annotation.

Table 3: Sequences down-regulated at least 1.7-fold by 5 weeks of treatment with phenobarbitol are shown with their corresponding annotation.

Table 4: Sequences upregulated at least 1.7-told by 5 weeks of treatment with phenobarbitol are shown with their corresponding annotation.

iv. Vectors and Host Cells Containing Nucleic Acid Molecules

The present invention also relates to recombinant DNA molecules comprising a nucleic acid sequence of the invention and a vector. The invention further relates to host cells (mammalian and insect) that containing the recombinant DNA molecules. Methods for obtaining such recombinant mammalian host cell, comprising introducing exogenous genetic material into a mammalian host cell are also provided by the invention. The present invention also relates to an insect cell comprising a mammalian cell containing a mammalian recombinant vector. The present invention also relates to methods for obtaining a recombinant mammalian host cell, comprising introducing into a mammalian cell exogenous genetic material.

A recombinant protein may be produced by opererably linking a regulatory control sequence to a nucleic acid of the present invention and putting it into an expression vector. Regulatory sequences include promoters, enhancers, and other expression control elements which are described in Goeddel (*Hene Expression Technology: Methods in Enzymology* 185. Academic Press, San Diego, Calif. (1990)). For example, the native regulatory sequences or regulatory sequences native to the transformed host cell can be used. One of skill in the art is familiar with numerous examples of these additional functional sequences, as well as other functional sequences, that may optionally be included in an expression vector. The design of the expression vector may depend on such factors as the choice of the host cell to be transformed, and/or the type of protein desired. Many such vectors are commercially available, including linear or enclosed elements (see for example, Broach, et al. Experimental Manipulation of Gene Expression, ed. M. Inouye, Academic Press. (1983); Sambrook, et al., *Molecular Cloning, A Laboratory Manual,* 2nd Ed., Cold Spring Harbor Press, Cold Spring Harbor, New York (1989)). Typically, expression constructs will contain one or more selectable markers, including the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K 12 strains), *Streptomyces, Pseudomonas, Serratia marcescens* and *Salmonella typhimurium*, insect cells (baculovirus), including *Drosophila*, fungal cells, such as yeast cells, plant cells, and ovary cells (CHO), and COS cells.

One may use different promoter sequences, enhancer sequences, or other sequences which will allow for enhanced levels of expression in the expression host. Thus, one may combine an enhancer from one source, a promoter region from another source, a 5'-noncoding region upstream from the initiation methionine from the same or different source as the other sequences, and the like. One may provide for an intron in the non-coding region with appropriate splice sites or for an alternative 3'-untranslated sequence or polyadenylation site. Depending upon the particular purpose of the modification, any of these sequences may be introduced, as desired.

Where selection is intended, the sequence to be integrated will have an associated marker gene, which allows for selection. The marker gene may conveniently be downstream from the target gene and may include resistance to a cytotoxic agent, e.g. antibiotics, heavy metals, resistance or susceptibility to HAT, gancyclovir, etc. complementation to an auxotrophic host, particularly by using an auxotrophic yeast as the host for the subject manipulations, or the like. The marker gene may also be on a separate DNA molecule, particularly with primary mammalian cells. Alternatively, one may screen the various transformants, due to the high efficiency of recombination in yeast, by using hybridization analysis, PCR, sequencing, or the like.

For homologous recombination, constructs can be prepared where the amplifiable gene will be flanked, normally on both sides, with DNA homologous with the DNA of the target region. Depending upon the nature of the integrating DNA and the purpose of the integration, the homologous DNA will generally be within 100 kb, usually 50 kb, preferably about 25 kb, of the transcribed region of the target gene, more preferably within 2 kb of the target gene. Where modeling of the gene is intended, homology will usually be present proximal to the site of the mutation. The term gene is intended to encompass the coding region and those sequences required for transcription of a mature mRNA. The homologous DNA may include the 5'-upstream region outside of the transcriptional regulatory region, or comprise any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this position. The homologous regions may extend over all or a portion of the target gene or be outside the target gene comprising all or a portion of the transcriptional regulatory regions and/or the structural gene.

Thus, the nucleic acid molecules described can be used to produce a recombinant form of the protein via microbial or eukaryotic cellular processes. Ligating the polynucleic acid molecule into a gene construct, such as an expression vector, and transforming or transfecting into hosts, either eukaryotic (yeast, avian, insect, plant, or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of encoded proteins or polypeptides by recombinant technologies.

B. Proteins and Polypeptides

The present invention also relates to proteins, peptides and polypeptides encoded by the nucleic acid sequences of the invention. Protein and peptide molecules can be identified using known protein or peptide molecules as a target sequence or target motif in the BLAST programs of the present invention. These proteins, peptides and polypeptides of the invention can be made using the nucleic acids or derived from the sequence information of the nucleic acids are also disclosed in the present invention. This invention also provides a compound or composition comprising one or more polypeptides, which comprise: I) at least one fragment, segment, or domain of at least 15–1,000 contiguous amino acids, with at least one portion encoded by one or more of SEQ NOS: 1–580; 2) at least one amino acid sequence selected from those encoding at least one of SEQ NOS: 1–580; or 3) at least one modification corresponding to fragments, segments, or domains within one of SEQ NOS: 1–580. The proteins, peptides and polypeptides of the invention can be made recombinantly as described above. Alternatively, the proteins, peptides and polypeptides of the invention can be produced synthetically.

Protein fragments or fusion proteins may be derivatized to contain carbohydrate or other moieties (such as keyhold limpet hemocyanin, etc.). A fusion protein or peptide molecule of the present invention is preferably produced via recombinant means.

Modifications can be naturally provided or deliberately engineered into the nucleic acids, proteins, and polypeptides of the invention to generate variants. For example, modifications in the peptide or DNA sequences can be made by those skilled in the art using known techniques, such as site-directed mutagenesis. Modifications of interest in the protein sequences may include the alteration, substitution., replacement, insertion or deletion of one or more selected amino acid residues. For example, one or more cysteine residues may be deleted or replaced with another amino acid to alter the conformation of the molecule. Additional cysteine residues can also be added as a substitute at sites to promote disulfide bonding and increase stability. Techniques for identifying the sites for alteration, substitution, replacement, insertion or deletion are well known to those skilled in the art. Techniques for making alterations, substitutions, replacements, insertions or deletions (see, e.g. U.S. Pat. No. 4,518,584) are also well known in the art. Preferably, any modification of a protein, polypeptide, or nucleic acid of the invention will retain at least one of the structural or functional attributes of the molecule.

The polypeptide or protein can also be tagged to facilitate purification, such as with histidine- or methionine-rich regions [His-Tag; available from LifeTechnologies Inc. Gaithersvurg, Md.] that bind to metal ion affinity chromatography columns, or with an epitope that binds to a specific antibody [Flag, available from Kodak, New Haven, CT].

A number of purification methods or means are also known and can be used. For example, reverse-phase high performance liquid chromatography (RP-HPLC).

C. Antibodies

This invention also provides an antibody, polyclonal or monoclonal, that specifically binds at least one epitope found in or specific to a carcinogenesis biomarker protein or polypeptide or a protein or polypeptide, of fragment or variant thereof, of this invention. Antibodies can be generated by recombinant, synthetic, or hybridoma technologies. One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention.

Nucleic acid molecules that encode all or part of the protein of the present invention can be expressed, by recombinant means, to yield protein or peptides that can in turn be used to elicit antibodies that are capable of binding the expressed protein or peptide. Such antibodies may be used in immunoassays for that protein or peptide. Such protein-encoding molecules or their fragments may be a "fusion" molecule (i.e, a part of a larger nucleic acid molecule) such that, upon expression, a fusion protein is produced. It is understood that any of the nucleic acid molecules of the present invention may be expressed, by recombinant means, to yield proteins or peptides encoded by these nucleic acid molecules.

The antibodies that specifically bind proteins and protein fragments of the present invention may be polyclonal or monoclonal, and may comprise intact immunoglobulins, or antigen binding portions of immunoglobulins (such as (F(ab'), F(ab')$_2$ fragments), or single-chain immunoglobulins producible, for example, via recombinant means. Conditions and procedures for the construction, manipulation and isolation of antibodies (see, for example, Harlow and Lane, *Antibodies: A Laboratory Manual*, Cold Spring Harbor Press. Cold Spring Harbor. New York (1988), the entirety of which is herein incorporated by reference) are well known in the art.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. Combinatorial chemistry techniques, for example, can be used to produce libraries of peptides (see WO 9700267), polyketides (see WO 960968), peptide analogues (see WO 9635781, WO 9635122, and WO 9640732), oligonucleotides for use as mimetic compounds derived from this invention. Mimetic compounds and libraries can also be generated through recombinant DNA-derived techniques. For example, phage display libraries (see WO 9709436). DNA shuffling (see U.S. Pat. No. 5,811,238) other directed or random mutagenesis techniques can produce libraries of expressed mimetic compounds. It is understood that any of the agents of the present invention can be substantially purified and/or be biologically active and/or recombinant.

Uses of the Invention

The present invention also provides methods for identifying carcinogen compounds. The nucleic acids, peptides and proteins of the invention can be useful in predicting the toxicity of test compounds. Nucleic acids represent biomarkers which are correlated to an altered cellular state. These markers, individually or in combination, can be measured in response to compounds to screen for those compounds that suppress or activate the genes and thus alter the state of the cell in an undesired manner. Specifically, the nucleic acids, peptides and proteins can be used directly in numerous methods well know in the art to identify or detect the presence of specific nucleic acid or amino acid sequences.

Carcinogens can be identified by contacting an animal, tissue from a mammal, or a mammalian cell, such as a rat hepatocyte, with a compound, under conditions allowing production of mRNA by the cell. The resulting mRNA is then separated and its presence or absence detected. Differential expression of these biomarkers can be monitored in tissues and fluids at the mRNA level using methods well known in the art such as Northern hybridizations, RNAase protection, NMR, rt-PCR, and in situ hybridizations. In vitro techniques can also be used to detect differential expression of genomic DNA such as, for example, Southern hybridizations.

Similarly, differential expression of these biomarkers can be monitored at the protein level using, for example, enzyme linked immunosorbent assays (ELISAs), Western blots. HPLC-liquid chromatography, NMR, immunoprecipitations and immunofluorescence. Protein identification can also be performed using new techniques including biomolecular interaction analysis (BIA) and matrix-assisted laser desorption/ionization time-of-flight mass spectrometry (MALDI-TOF). (Nelson et al., Interfacing biomolecular interaction analysis with mass spectrometry and the use of bioreactive mass spectrometer probe tips in protein characterization, in Techniques in Protein Chemistry VIII, p. 493–504, 1997; Kalrsson et al., Experimental design for kinetic analysis of protein—protein interactions with surface plasmon resonance biosensors, J. Immun. Meth, 220, 121–133, 1997; Krone et al. BIA/MS: Interacting biomolecular interaction analysis with mass spectrometry, Anal. Chem. 244, 124–132, 1997; and Wong et al. Validation parameters for a novel biosensor assay which simultaneously measures serum concentrations of a humanized monoclonal antibody and detects induced antibodies. J. Immun. Meth. 209, 1–15, 1997.)

Using the catalog of the present invention, one skilled in the art can predict with the tested compound is a carcinogen. Compounds that results in the production of nucleic acids, peptides or protein from the catalog, or a subset of catalog, are carcinogenic. To be able to predict carcinogenic, one need not use all of the nucleic acids or peptides of the present invention. For example, if one tested for all of the disclosed biomarkers and found 20% or more to be differentially expressed this would predict that the test compound is a carcinogen. Alternatively, one could use a sub-set of the biomarkers, such as, for example. 20–30 of the nucleic acids. With such a sub-set one would expect 70–80% to be differentially expressed when the test compound is a carcinogen. In addition, one could select only a few of the biomarkers, for example, 10, and look for 100% of them to be differentially expressed as an indication of a carcinogen.

mRNA, protein, or genomic DNA of the invention can be detected in biological samples including, for example, tissues, cells, or biological fluids from a subject such as blood, urine, or liver and thyroid tissue.

Various microarrays, beads, glass or nylon slides, membranes or other repeatable assay apparati can be constructed using the nucleic acids, peptides, and proteins of the present invention. These apparati can then be used to detect differential expression of these biomarkers. A non-limiting description of selected methods follows.

A. Microarrays

In one embodiment, the nucleic acids of the invention can be used to monitor expression. A microarray-based method for high-throughput monitoring of gene expression may be utilized to measure carcinogenesis biomarker hybridization targets. This 'chip'-based approach involves using microarrays of nucleic acids as specific hybridization targets to quantitatively measure expression of the corresponding genes (Schena et al. Science 270:467–470 (1995), the entirety of which is herein incorporated by reference: Shalon. Ph.D. Thesis. Stanford University (1996), the entirety of which is herein incorporated by reference). Every nucleotide in a large sequence can be queried at the same time. Hybridization can also be used to efficiently analyze nucleotide sequences.

Several microarray methods have been described. One method compares the sequences to be analyzed by hybridization to a set of oligonucleotides or cDNA molecules representing all possible subsequences (Bains and Smith, *J. Theor. Biol.* 135:303 (1989), the entirety of which is herein incorporated by reference). A second method hybridizes the sample to an array of oligonucleotide or cDNA probes. An array consisting of oligonucleotides or cDNA molecules complementary to subsequences of a target sequence can be used to determine the identity of a target sequence, measure its amount, and detect differences between the target and a reference sequence. Nucleic acid microarrays may also be screened with protein molecules or fragments thereof to determine nucleic acids that specifically bind protein molecules or fragments thereof.

The microarray approach may also be used with polypeptide targets (see. U.S. Pat. Nos. 5,800,992, 5,445,934; 5,143, 854; 5,079,600, 4,923,901, all of which are herein incorporated by reference in their entirety). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides (Fodor el al., *Science* 251:767–773 (1991), the entirety of which is herein incorporated by reference).

B. Hybridization Assays

Oligonucleotide probes, whose sequences are complementary to that of a portion of the nucleic acids of the invention such as SEQ NO.: 1–580, can be constructed. These probes are then incubated with cell extracts of a patient under conditions sufficient to permit nucleic acid hybridization. The detection of double-stranded probe-mRNA hybrid molecules is indicative of biomarkers of carcinogenesis or sequences derived from rat liver hepatocytes treated with a nongenotoxic carcinogen. Thus, such probes may be used to ascertain the level and extent of carcinogenesis or the production of certain proteins. The nucleic acid hybridization may be conducted under quantitative conditions or as a qualitative assay.

C. PCR Assays

A nucleic acid of the invention, such as one of SEQ NO.: 1–580 or complements thereof, can be analyzed for use as a PCR probe. A search of databases indicates the presence of regions within that nucleic acid that have high and low regions of identity to other sequences in the database. Ideally, a PCR probe will have high identity with only the sequence from which it is derived. In that way, only the desired sequence is amplified. Computer generated searches using programs such as MIT Primer3 (Rozen and Skaletsky (1996, 1997, 1998)), or GeneUp (Pesole, et al. *BioTechniques* 25:112–123 (1998)), for example, can be used to identify potential PCR primers.

The PCR probes or primers can be used in methods such as described in Krzesicki, et al., *Am. J. Respir. Cell Mol. Biol.* 16:693–701 (1997) (incorporated by reference in its entirety) to identify or detect sequences expressed in carcinogenesis.

These detailed descriptions are presented for illustrative purposes only and are not intended as a restriction on the scope of the invention. Rather, they are merely some of the embodiments that one skilled in the art would understand from the entire contents of this disclosure. All parts are by weight and temperatures are in Degrees centigrade unless otherwise indicated.

EXAMPLES

The following examples will illustrate the invention in greater detail, although it will be understood that the invention is not limited to these specific examples. Various other examples will be apparent to the person skilled in the art after reading the present disclosure without departing from the spirit and scope of the invention. It is intended that all such other examples be included within the scope of the appended claims.

Example 1

Rats were treated with phenobarbital for thirteen weeks or in a separate experiment, for 5 days. Liver mRNAs were extracted and probed for those mRNAs specifically altered by phenobarbital treatment by comparing with mRNA expression in untreated rats. The relative abundance of cellular mRNAs in rat liver was determined using PE GenScope's AFLP (Amplified Fragment Length Polymorphism)-based Transcript Imaging technology. The mRNA is converted into double-stranded cDNA, which is then cut with restriction enzymes. The resulting restriction fragments are tagged with specific adapters of known sequences, which allows for subsequent amplification of the fragments under highly stringent conditions. Similar technology has been used in plants (Money. T. et al., Nucleic Acids Res. 24:2616–2617 (1996), incorporated by reference in its entirety).

Specifically, rats were treated by oral gavage for 88 days in the 13 week experiment, or for 5 days with 200 mg/kg phenobarbital or control vehicle. The average expression levels of mRNAs for three phenobarbital-induced genes (P450 2B1, P1450 3A1, and UDP-glucuronosyl transferase) were measured using RT-PCR, and showed substantial induction of mRNA expression levels as compared to control rats.

In one study, ten differentially expressed transcript derived fragments (TDF's) were isolated and cloned. For each TDF, four or five colonies were picked and their sequences determined using standard sequencing techniques. In each case, all colonies sequenced contained the same sequences. This is a reflection of the ability to reduce the complexity of the AFLP gel profile by using primers with additional selective nucleotides. The ten TDF sequences were BLASTed against GenBank. The identities of the bands were consistent with what one might predict would be altered by treatment with phenobarbital. PCR analysis of the samples confirmed that these genes are differentially expressed following treatment.

Example 2

Validation of AFLP Biomarkers by rt-PCR (Taqman)

After AFLP experiments were conducted, and results analyzed, the effects of phenobarbital on the expression of several biomarkers were validated. RNA was extracted from the same liver samples used in the AFLP study, in addition to liver samples from rats treated with phenobarbital for 2-weeks, followed by reverse transcription reactions to generate cDNA, followed by PCR, using Taqman technology. The genes analyzed for phenobarbital-induced alterations, and the corresponding AFLP sequence numbers are listed in Table 5, and a graph and a chart of the actual results are in Table 6 and FIG. 1.

The results indicate that AFLP technology can find biomarkers. Eleven of the 17 (65%) genes analyzed were also determined to be differentially expressed using rt-PCR. However, this is based on comparisons at the same timepoint (13 weeks). When the rt-PCR analyses performed on the 2 week samples are considered, another marker (S-033) is found to be differentially expressed. Theoretically, differences in sensitivity and or specificity between the two techniques could be accounted for these minor discrepancies. However, S-033 is an example of how AFLP has identified biomarkers which are optimal for carcinogen detection at timepoints other than 13 weeks.

As noted above, the specific examples should not be interpreted as a limitation to the scope of the invention. Instead, they are merely exemplary embodiments one skilled in the art would understand from the entire disclosure of this invention.

TABLE 1

| SEQ NO | Annotation* |
|---|---|
| 275 | rat mRNA for (S)-2-hydroxy acid oxidase |
| 276 | human NADH-ubiquinone oxidoreductase |
| 277 | rat mRNA organic anion transporter 3 |
| 278 | Ula-1 RNA from transformed mouse cell line |
| 279 | rat hemoglobin alpha chain gene |
| 280 | rat mRNA for calcium binding protein |
| 281 | rat heat shock protein 27 |
| 282 | rat mRNA for 50-kDa bone sialic acid |
| 283 | rat mRNA for lactate dehydrogenase |
| 284 | rat ribonuclease 4 mRNA |
| 285 | mouse Src-associated adaptor protein |
| 286 | rat mRNA for plasminogen protein |
| 287 | rat gene 33 DNA |
| 288 | rat mRNA for 50-kDa bone sialic acid |
| 289 | mouse glycolate oxidase mRNA |
| 290 | rat mRNA for cytochrome b5 |
| 291 | mouse mRNA for tripeptidyl peptidase II |
| 292 | human eukaryotic protein synthesis init. |
| 293 | rat fatty liver acid binding protein |
| 294 | rat mRNA for ATP-stimulated glucocorticoid receptor translocation promoter |
| 295 | mouse apolipoprotein A-I/CIII mRNA |
| 296 | rat fibronectin (cell-, heparin-, and fibrin-binding domains) |
| 297 | rat mRNA encoding liver fatty acid binding |
| 298 | rat RoBo-1 mRNA |
| 299 | rat mRNA for pre-alpha-inhibitor, heavy chain |
| 300 | rat pancreatic secretory trypsin inhibitor |
| 301 | rat apolipoprotein A-IV mRNA |
| 302 | rat apolipoprotein A-IV mRNA |
| 303 | rat lecithin: cholesterol acyltransferase |
| 304 | mouse mRNA for very-long-chain acyl-CoA |
| 305 | rat Cyp3a locus |
| 306 | rat gene for alpha-fibrinogen |
| 307 | mouse protein phosphatase-1 binding protein |
| 308 | novel human mRNA similar to rat 45 kDa secretory protein |
| 309 | |
| 310 | rat retinol dehydrogenase type III mRNA |
| 311 | rat mRNA for lecithin-cholesterol acyltransferase |
| 312 | rat oxidative 17 beta hydroxysteroid dehydrogenase |
| 313 | rat hydroxysteroid sulfotransferase mRNA |
| 314 | mouse major histocompatibility locus cla |
| 315 | mouse ubiquitinating enzyme E2-230 kDA mRNA |
| 316 | mouse fatty acid transport protein 5 mRNA |
| 317 | rat (TSC-22) mRNA |
| 318 | rat SMP30 mRNA for senescence marker protein |

TABLE 2

| SEQ NO | Annotation |
|---|---|
| 319 | rat cytochrome P450 |
| 320 | rat cytochrome P450b |
| 321 | rat cytochrome P450 |
| 322 | |
| 323 | rat cytochrome P450 mRNA, 3' end |
| 324 | rat mRNA for carboxylesterase precursor |
| 325 | rat cytochrome P450e |
| 326 | rat aldehyde dehydrogenase (ALDH) mRNA |
| 327 | rat mRNA for carboxylesterase precursor |
| 328 | rat aldehyde dehyrdogenase (ALDH) mRNA |
| 329 | rat lipoprotein lipase mRNA |
| 330 | rat cytochrome P450IIB3 |
| 331 | rat mRNA for P450IIIA23 protein |
| 332 | rat aflatoxin B1 aldehyde reductase |
| 333 | rat ,RMA for cytochrome P450 3A |
| 334 | rat testosterone 6-beta-hydroxylase (CYP 3A1) mRNA |
| 335 | rat mRNA for amyloidogenic glycoprotein |
| 336 | rat cytochrome P50 PB1 (PB1 allele) mRNA |
| 337 | rat epoxide hydrolase mRNA |
| 338 | rat mRNA for P450IIIA23 protein |
| 339 | rat CYP 3A1 mRNA |
| 340 | rat mRNA for hydroxysteroid sulfotransferase |
| 341 | rat mRNA for cytochrome P450 |
| 342 | rat NADPH-cytochrome P450 reductase mRNA |
| 343 | |
| 344 | rat liver glutathione-S-transferase Yb-1 |
| 345 | rat cytochrome P450 processed pseudogene |
| 346 | rat mRNA for glutathione S-transferase |
| 347 | rat NADPH-cytochrome P450 reductase mRNA |
| 348 | rat mRNA for P450IIIA23 protein |
| 349 | rat delta-aminolevulinate synthase mRNA |
| 350 | rat mRNA for glutathione S-transferase |
| 351 | rat mRNA for amyloidogenic glycoprotein |
| 352 | human GSTT1 mRNA |
| 353 | rat cytochrome P450IIB3 |
| 354 | rat mRNA for glutathione transferase subunit 8 |
| 355 | rat cytochrome P450IIB3 |
| 356 | rat NADPH-cytochrome P450 reductase mRNA |
| 357 | rat glutathione S-transferase mRNA |
| 358 | rat NADPH-cytochrome P450 oxidoreductase |
| 359 | mouse mRNA for glutathione S-transferase |
| 360 | glutathione S-transferase |
| 361 | rat mRNA for glutathione transferase subunit 8 |
| 362 | rat NADPH-cytochrome P450 oxidoreductase |
| 363 | rat cytochrome P450 PB1 (PB1 allele) mRNA |
| 364 | rat cytochrome P450 PB1 (PB1 allele) mRNA |
| 365 | glutathione S-transferase Ycl subunit |
| 366 | rat 5-aminolevulinate synthase mRNA |
| 367 | rat cytochrome P450f mRNA |
| 368 | rat mRNA for polyubiquitin, 5' end |
| 369 | *M. aureus* mRNA for cytochrome P450IIC |
| 370 | preprocathepsin β (mouse, B16a melanoma) |
| 371 | rat phosphoglucomutase mRNA |
| 372 | rat malic enzyme gene, exon 4 |
| 373 | rat mRNA for glutathione S-transferase |
| 374 | rat cytochrome P450 mRNA |
| 375 | rat cytochrome P450 mRNA |
| 376 | rat cytochrome P450 mRNA |
| 377 | |
| 378 | human mitochondrial prostatein C3 subunit homolog |
| 379 | rat cytochrome P450 3A9 mRNA |
| 380 | rat cytochrome P450-1/PB- (ps) gene. exon |
| 381 | rat Hsp70-1 gene |
| 382 | rat cytochrome P450 mRNA |
| 383 | |
| 384 | human mRNA for transcription factor BTF |
| 385 | mesocricetus auratus mRNA for carboxylesterase |
| 386 | rat aromatic L-amino acid decarboxylase |
| 387 | rat mRNA for putative progesterone binding protein |
| 388 | rat Y-b3 glutathione S-transferase mRNA |
| 389 | rat NADPH-cytochrome P450 reductase mRNA |
| 390 | rat cytochrome PB23 mRNA |
| 391 | UGT2B4, UDP-glucuronosyltransferase 2B4 |
| 392 | rat glutathione S-transferase A3 subunit |
| 393 | rat mRNA for cytochrome b5 |
| 394 | rat mRNA for glutathione S-transferase |
| 395 | rat cytochrome P450 3A9 mRNA |
| 396 | glutathione s-transferase Ycl subunit |
| 397 | bilirubin-specific UDP-glucuronosyltransferase |
| 398 | rat cytochrome P450 mRNA |
| 399 | rat p450Md mRNA for cytochrome P450 |
| 400 | mouse glutathione S-transferase class mu |
| 401 | |
| 402 | |
| 403 | rat mRNA for beta-tubulin T beta15 |
| 404 | human microsomal glutathione s-transferase |
| 405 | rat transketolase mRNA |
| 406 | rat cytochrome P450 (female-specific and growth hormone-inducible) mRNA |
| 407 | rat cytochrome P450 (female-specific and growth hormone-inducible) mRNA |
| 408 | NPT4, sodium phosphate transporter |
| 409 | rah- ras-related homolog (mouse HT4 neuro) |
| 410 | human mRNA for 16G2 |
| 411 | rat mRNA for analicular multidrug resistance |
| 412 | rat UDP-glucuronosyltransferase UGT1A7 mRNA |
| 413 | human sodium phosphate transporter (NPT4) |
| 414 | rat liver apolipoprotein A-1 mRNA |
| 415 | rat UDP-glucuronosyltransferase mRNA |
| 416 | rat apolipoprotein A-1 gene |
| 417 | mouse gene encoding tetranectin |
| 418 | mouse COP9 complex subunit 7a (COPS7a) mRNA |

TABLE 3

| SEQ NO | Annotation |
|---|---|
| 419 | rat mRNA for hydroxysteroid sulfotransferase |
| 420 | Zfp-29 gene for zinc finger protein |
| 421 | human HFREP-1 mRNA |
| 422 | mouse ATP sulfurylase/APS kinase 2 |
| 423 | |
| 424 | mouse secreted apoptosis-related protein |
| 425 | human zinc finger gene ZNF2 |
| 426 | rat angiotensinogen (PAT) gene, exon 2 |
| 427 | |
| 428 | mouse methyltransferase (Cyt19) |
| 429 | mouse activin beta-c precursor gene |
| 430 | |
| 431 | |
| 432 | |
| 433 | |
| 434 | rat mRNA for hepatic lipase |
| 435 | |
| 436 | human (H326) mRNA |
| 437 | human mRNA for K1AA00181 gene |
| 438 | |
| 439 | mouse mRNA for paladin gene |
| 440 | |
| 441 | mouse activin beta-c precursor gene |
| 442 | rat orphan receptor RLD-1 (rld-1) mRNA |
| 443 | mouse oncomodulin gene (exon 1) |
| 444 | rat kallistatin mRNA mRNA |
| 445 | |
| 446 | rat gonadotropin-releasing hormone |
| 447 | URP- nuclear calmodulin-binding protein gb113vrtp |
| 448 | mouse Jun co-activator Jab1 (Jab 1) mRNA |
| 449 | rat zinc finger binding protein mRNA |
| 450 | mouse inhibitor of apoptosis protein 2 mRNA |
| 451 | |
| 452 | rat mRNA for glutathione peroxidase 1 |
| 453 | mouse CRBPI mRNA for cellular retinol |
| 454 | mouse wagneri mRNA for heat shock |
| 455 | mouse NPCl (Npcl) mRNA |
| 456 | |
| 457 | |

TABLE 4

| SEQ NO | Annotation |
|---|---|
| 458 | rat UDP-glucuronosyltransferase-2 (UDPGT) |
| 459 | rat ribosomal protein S12 mRNA |
| 460 | rat ornithine decarboxylase (ODC) mRNA |
| 461 | rat cytokeratin 8 polypeptide mRNA |
| 462 | rat mRNA for cathepsin L |
| 463 | human rho GDI mRNA |
| 464 | rat CLP36 (clp36) mRNA |
| 465 | annexin II, 36 kDa calcium-dependent phos. |
| 466 | |
| 467 | rat ribosomal protein S18 mRNA |
| 468 | rat ornithine decarboxylase (ODC) mRNA |
| 469 | mouse (C57BL/6) GB-like mRNA |
| 470 | cyclic protein-2 cathepsin L proenzyme |
| 471 | human p27 mRNA |
| 472 | rat c-myc oncogene and flanking regions |
| 473 | rat mRNA for canalicular multispecific |
| 474 | mouse ctla-2-beta mRNA homolog |
| 475 | rat 3-hydroxy-3-methlyglutaryl CoA reductase |
| 476 | rat stathmin mRNA |
| 477 | rat mRNA for Mx1 protein |
| 478 | |
| 479 | rat mRNA for protein phosphatase-2A catalytic subunit |
| 480 | rat mRNA for Mx2 protein |
| 481 | human mRNA for MUF1 protein |
| 482 | mouse MA-3 (apoptosis-related gene) mRNA |
| 483 | human BRCA2 region, mRNA sequence CG012 |
| 484 | |
| 485 | pre-mtHSP70, 70 kDa heat shock protein |
| 486 | |
| 487 | house mouse mRNA for MAP kinase, kinase 3B |
| 488 | rat mRNA for 14-3-3 protein gamma-subtype putative protein kinase C |
| 489 | human homolog of the *Aspergillus nidulans* sudD gene product |

*ANNOTATIONS REPRESENT THE PREDICTION OF THE BIOLOGICAL FUNCTIONS OF THE SEQUENCES BASED ON SIMILARITY TO KNOWN SEQUENCES.

TABLE 5

| SEQ. NO. | Gene |
|---|---|
| 3 | Rat P-450 |
| 4 | Rat aldehyde dehydrogenase |
| 6 | Rat UDPGT1.1 |
| 10 | Rat vitamin D-binding protein |
| 179 | Rat UDPGT |
| 25 | Rat cytochrome B |
| 114 | Rat delta-aminolevulinate synthase |
| 129 | Glutathione S-transferase |
| 34 | Rat liver catalase |
| 38 | Rat alpha-2u globulin |
| 40 | Rat NADP-dep.isocitrate dehydrogenase |
| 42 | Mouse JAK1 (protein tyrosine kinase) |
| 230 | Rat carboxylesterase |
| 46 | Rat cathepsin B |
| 52 | (s)-2-hydroxy acid oxidase |
| 116 | Estrogen sulfotransferase |
| 92 | Rat nicotinic receptor alpha 7 subunit |

TABLE 6

| SEQ NO. | Fold Change | | |
|---|---|---|---|
| | 2-week | 13-week | AFLP |
| 3 | 1.34 | 1.85 | 2.3 |
| 4 | 16.36 | 12.88 | 8.2 |
| 6 | 0.93 | 1.5 | 4.6 |
| 10 | 0.66 | 0.79 | 1.7 |
| 179 | 14.11 | 9.05 | 10.5 |
| 25 | 1.85 | 0.75 | 4.2 |
| 114 | 1.22 | 4.03 | 3.8 |
| 129 | 2.52 | 4.03 | 4 |
| 34 | 0.79 | 0.45 | 16 |
| 38 | 0.35 | 0.03 | 0.04 |
| 40 | 0.88 | 1.14 | 2.5 |
| 42 | 0.8 | 0.83 | 1.9 |
| 230 | 4.24 | 5.74 | 1.3 |
| 46 | 0.87 | 1.41 | 2.3 |
| 52 | 0.31 | 0.09 | 0.3 |
| 116 | 0.81 | 0.15 | 0.32 |
| 92 | 0.45 | 0.72 | 6.3 |

TABLE 7

| Gene Description | 5' Primer Sequence 5' to 3' | 3' Primer Sequence 5' to 3' | Taqman Probe Sequence |
|---|---|---|---|
| Rat liver catalase | 550 | 519 | 490 |
| Rat Carboxylesterase | 551 | 520 | 491 |
| Rat cathepsin B | 552 | 521 | 492 |
| canalicular multidrug resistance protein | 553 | 522 | 493 |
| (s)-2-hydroxy acid oxidase | 554 | 523 | 491 |
| estrogen sulfotransferase | 555 | 524 | 495 |
| protective protein (heat shock proetin 90A | 556 | 525 | 496 |
| Rat hepatic alp-2u globulin | 557 | 526 | 497 |
| Rat transferrin | 558 | 527 | 498 |
| Cytocrhome P450 | 559 | 528 | 499 |
| Aldehyde dehydrogenase, rat | 560 | 529 | 500 |
| 3-methylcholanthrene-inducible UDP gluc.trans | 561 | 530 | 501 |
| rat senescence marker | 562 | 531 | 502 |
| Vitamin D binding protein, Rat | 563 | 532 | 503 |
| RB binding protein 2 | 564 | 533 | |
| UDP-glucoronosyltransferase 1 | 565 | 534 | 504 |
| mitochondrial gene fragment, Rat | 566 | 535 | 505 |
| Rat delta-aminolevulinate synthase | 567 | 536 | 506 |
| human flavoprotein | 568 | 537 | 507 |
| alpha-2u globulin, Rat | 569 | 538 | 508 |
| glutathione-S-transferase | 570 | 539 | 509 |
| rat cytosolic NADP-dependent isocitrate | 571 | 540 | 510 |
| Protein tyrosine kinase | 572 | 541 | 511 |
| hepatic steroid hydroxylase | 573 | 542 | 512 |
| Nicotinic receptor, alpha sub. unit | 574 | 543 | 513 |
| Alpha B-crystallin, heart | 575 | 544 | 514 |
| Bos Taurus aldehyde oxidase | 576 | 545 | 515 |
| lambda-crystallin | 577 | 546 | 516 |
| Vav2 | 578 | 547 | 517 |
| MDM2 | 579 | 548 | 518 |
| DAD1 | 580 | 549 | |

We claim:

1. A method for determining a level of a carcinogenesis biomarker in a cell in vitro comprising:
   (a) incubating, under conditions permitting specific nucleic acid hybridization, a marker nucleic acid molecule, said marker nucleic acid molecule having a nucleic acid sequence of SEQ NO. 488 or the component, with a nucleic acid molecule obtained from said cell, wherein nucleic acid hybridization between said marker nucleic acid molecule, and said complementary nucleic acid molecule obtained from said cell permits the detection of said carcinogenesis biomarker;
   (b) permitting hybridization between said marker nucleic acid molecule and said complementary nucleic acid molecule obtained from said cell; and
   (c) detecting the level of said complementary nucleic acid, wherein the detection of said complementary nucleic acid is predictive of the level of said carcinogenesis biomarker.

2. The method of claim 1, wherein said level is predictive of said carcinogenesis biomarker.

3. The method of claim 1, wherein said level is detected by in situ hybridization.

4. A method for measuring the carcinogenicity of a composition comprising:
   (a) culturing a cell line in vitro;
   (b) exposing said cell line to said composition; and
   (c) determining the presence or absence of mRNA which substantially hybridizes to at least one nucleic acid sequence selected from the group consisting of SEQ NOS: 280, 384, and 488 and the complements thereof.

5. A method for measuring the carcinogenicity of a composition comprising:
   (a) exposing a hepatocyte in vitro to said composition; and
   (b) detecting the presence or absence in said hepatocyte of mRNA which substantially hybridizes to at least one nucleic acid sequence selected from the group consisting of SEQ NOS: 280, 384, and 488 and the complements thereof.

6. The method of claim 5, wherein said hepatocyte is a rat hepatocyte.

* * * * *

UNITED STATES PATENT AND TRADEMARK OFFICE
CERTIFICATE OF CORRECTION

PATENT NO. : 6,924,099 B1
DATED : August 2, 2005
INVENTOR(S) : Roderick T. Bunch et al.

It is certified that error appears in the above-identified patent and that said Letters Patent is hereby corrected as shown below:

Column 263,
Lines 23-24, please replace "SEQ NO. 488 or the component" with -- SEQ NO. 488 or the complement thereof --.

Signed and Sealed this

Eleventh Day of October, 2005

JON W. DUDAS
*Director of the United States Patent and Trademark Office*

SEQUENCE LISTING

<160> NUMBER OF SEQ ID NOS: 580

<210> SEQ ID NO 1
<211> LENGTH: 271
<212> TYPE: DNA
<213> ORGANISM: Rattus norvegicus

<400> SEQUENCE: 1

```
gatccaccta acaagaagcc caaagtctag acgtcgcctt ttgcctgtga tgatttggta      60
ctgcagggta gccagcgtct gtctgatact aagtggtaaa tgaactacgt gttttatgg     120
gaaacaaaaa tattttgta atcatcaaat ttatactagc tatctgggtg ttagcatatc     180
tagtaattat gagtctagaa taattttac atatttttat attattgtcc tctcagttac     240
tgaatggatg gaaaacaatc atgttggttt a                                   271
```

<210> SEQ ID NO 2
<211> LENGTH: 206
<212> TYPE: DNA
<213> ORGANISM: Rattus norvegicus

<400> SEQUENCE: 2

```
gatccaagac cctcgctgac tccgtctgaa ttttggttt cagtttggta cccgaagctg      60
cgcggcgcgt ctgcttgtta cttgtttgac tgttggaatt gtttgtcttc tttgtgacct    120
gactgtggtt ttctggacgt gttgtgtctg ttagtgtctt tttgactttt gtttcgtgtt    180
tgaatttgga ctgacgactg tgttta                                         206
```

<210> SEQ ID NO 3
<211> LENGTH: 74
<212> TYPE: DNA
<213> ORGANISM: Rattus norvegicus

<400> SEQUENCE: 3

```
gatccatgat actgcatgtc agattttcat gtgaatattc tgattgttcg atgttgtttg      60
cctgttttg ttta                                                         74
```

<210> SEQ ID NO 4
<211> LENGTH: 207
<212> TYPE: DNA
<213> ORGANISM: Rattus norvegicus

<400> SEQUENCE: 4

```
gatccatggt caaacaatac cgagtgatgg agacattttc acttttacga gacgtgaacc      60
tattggggtg tgtggccaaa tcatcccttg gaattttcca ctgcttatgt tcatttggaa    120
gatagccctg ccctcagctg tgggaacaca gtggtcgtca agccagcaga gcaaactcct    180
ctcactgctc ttcacatggc atcttta                                        207
```

<210> SEQ ID NO 5
<211> LENGTH: 147
<212> TYPE: DNA
<213> ORGANISM: Rattus norvegicus

<400> SEQUENCE: 5

```
gatccacaat gggcagaagt tagtggttcc caggattgct gggagcatgg cactgtcaaa      60
tcactaccgc tctgaagatt tattagacgt tgacactgct gccggaggat tcagcagaga    120
cagggactga actactgtct cccttta                                        147
```

```
<210> SEQ ID NO 6
<211> LENGTH: 366
<212> TYPE: DNA
<213> ORGANISM: Rattus norvegicus
<220> FEATURE:
<221> NAME/KEY: unsure
<222> LOCATION: (1)..(366)
<223> OTHER INFORMATION: unsure at all n locations

<400> SEQUENCE: 6
gatccatggt ctcagagatt ccagagaaga aagcgatgga aatcgctgag gctttgggca      60
gaattcctcn agacggtcct gtggcngcta caccngggaa ctagaccatc gaaccttgca     120
aagaacacta ttcttgtcaa atggctaccc caaaacgatc tgcttggtca tccaaaggct     180
cgggcgttca tcacacactc ccggttccca tggtatttat gaaggaatat gcaatggggt     240
tcccaatggt gatgatgccc ttgtttggtg atcagatgga caacgccaag cgcatggaaa     300 ctcgggagc tggggtgacc ctgaatgtcc tgaaaatgac tgccgatgat ttggaaaacg      360
ccctta                                                                366

<210> SEQ ID NO 7
<211> LENGTH: 156
<212> TYPE: DNA
<213> ORGANISM: Rattus norvegicus
<220> FEATURE:
<221> NAME/KEY: unsure
<222> LOCATION: (1)..(156)
<223> OTHER INFORMATION: unsure at all n locations

<400> SEQUENCE: 7
gatccactga agncatcctt gaccgatagg natcaccccg gacttcgatg caccagaggg      60
cgcaaagcat gagggctggg agaggaccnn ggtgtttgcc tggccagtgt gaagcagtca     120
caaggaggtg actggacaaa ctagcatgtg gcctta                                156

<210> SEQ ID NO 8
<211> LENGTH: 103
<212> TYPE: DNA
<213> ORGANISM: Rattus norvegicus

<400> SEQUENCE: 8
gatccaggca agttgggaga atatgacgct agtatcataa acagggtgcc aggaaaatcc      60
actattacca acattccaa tgactcctat agctgttgcc tta                         103

<210> SEQ ID NO 9
<211> LENGTH: 127
<212> TYPE: DNA
<213> ORGANISM: Rattus norvegicus
<220> FEATURE:
<221> NAME/KEY: unsure
<222> LOCATION: (1)..(127)
<223> OTHER INFORMATION: unsure at all n locations

<400> SEQUENCE: 9
gatccaaaag ttcttcgggc aacacgtcct tcagtctgga ggctaactct aaatagtgtg      60
accatgtang acagagtaaa gggcagggag tgaattagag aagaagttgg aattggtctg     120
gggatta                                                                127

<210> SEQ ID NO 10
<211> LENGTH: 400
<212> TYPE: DNA
```

<213> ORGANISM: Rattus norvegicus
<220> FEATURE:
<221> NAME/KEY: unsure
<222> LOCATION: (1)..(400)
<223> OTHER INFORMATION: unsure at all n locations

<400> SEQUENCE: 10

```
gatccaaagg gattggccga tcagtttcta ttcgaatatt ccagcaatta cggacaagct      60
cntctgccac ttttagttgg gttacaccaa gagttatctc tctatggtcg gctcctgctg     120
tacttctgca aaaccaactg tgtgcttttt gaaggagaga ctccagatga aacagttatc     180
acttctcacc actatgtcaa acagagtctg ctcacaatat gctgcatatg gaaaggaaaa     240
atcaaggatg agccatctca taaaactagc ccaaaaagta ccaactgcta acctggagga     300
tgttctgcca ctcgctgaag accttactga aatcctgtcc agatgttgta agtctacctc     360
agaagactgc atggccagag agctgcctga acacacatta                           400
```

<210> SEQ ID NO 11
<211> LENGTH: 57
<212> TYPE: DNA
<213> ORGANISM: Rattus norvegicus

<400> SEQUENCE: 11

```
gatccagaaa cttctgctaa gacttcttca atggaaaaga gctgaataag agcatta        57
```

<210> SEQ ID NO 12
<211> LENGTH: 231
<212> TYPE: DNA
<213> ORGANISM: Rattus norvegicus
<220> FEATURE:
<221> NAME/KEY: unsure
<222> LOCATION: (1)..(231)
<223> OTHER INFORMATION: unsure at all n locations

<400> SEQUENCE: 12

```
gatccccagt tcatcagtg tccctgtagc tttctgcagc actcttgggc tggacagagc       60
tcctggaaac atttcaaaag atcactnccc ttaccctgcc cttccttggg gtccacctgg     120
tgctccagtg ggattgcaca agaatgtctg tgcagaagca aagacagcct ttttaccagt     180
gtggccaaag ccttcacaca tacgggtacc tgttttacac tgtgatgttt a              231
```

<210> SEQ ID NO 13
<211> LENGTH: 295
<212> TYPE: DNA
<213> ORGANISM: Rattus norvegicus
<220> FEATURE:
<221> NAME/KEY: unsure
<222> LOCATION: (1)..(295)
<223> OTHER INFORMATION: unsure at all n locations

<400> SEQUENCE: 13

```
gatcccacag cacagttgcc ttttgaacaa cacaagttgc tgcagcattt gaaacaccaa      60
cagcagtgca tacgaacaag atagtggcaa gggccatgcc aagccttcac cttccaaggg    120
ctaaataggc caccaagtga cagcaaaatg gtgccaaagn tctactacag cactgctaag    180
aaccgacagc tgagaagccg gatagcttct gacctagagt gcacacacct aagtcctcaa    240
ctggaccttg atagccaaca aatgggagca gtgtcttgtc tctttagcac cttta         295
```

<210> SEQ ID NO 14
<211> LENGTH: 188
<212> TYPE: DNA
<213> ORGANISM: Rattus norvegicus -continued

```
<400> SEQUENCE: 14
gatcccggag gccgaggcta gagactattc tgtcactcct ggtatccctt cagaagttgc      60
ctgtacgatt gcctgaagga gaagcactgc agtgtttgac agagcgtgct atgagttggc     120
aagatagagc acgacaagct ttagccacag atgaactgtc ttctgccctg ccaaactct      180 ctgtgtta                                                               188

<210> SEQ ID NO 15
<211> LENGTH: 194
<212> TYPE: DNA
<213> ORGANISM: Rattus norvegicus

<400> SEQUENCE: 15
gatccccttt cccagtgata cccagatttg atttgattgc ccgttttggt ccatgttggt      60
ataggttgga atggtgagca atatcagaga accatgtttt ctctcaggac actttctgtg    120
ctggggtagc acaggctgtc atgctcagca taggtgctcg ctctgctaca ctagtccttc    180
aaagtcgtgg ctta                                                       194

<210> SEQ ID NO 16
<211> LENGTH: 164
<212> TYPE: DNA
<213> ORGANISM: Rattus norvegicus
<220> FEATURE:
<221> NAME/KEY: unsure
<222> LOCATION: (1)..(164)
<223> OTHER INFORMATION: unsure at all n locations

<400> SEQUENCE: 16
gatccngact gagaagagtn tcaacacggt cccctacata gtgggcttca acaagcaaga      60
gtttggctgg atcattccaa cgatgatggg aaatctactc tctgaaggca gaatgaatga    120
gaaaatggcc agttctttct tgaagaggtt cagccctaac ctta                     164

<210> SEQ ID NO 17
<211> LENGTH: 43
<212> TYPE: DNA
<213> ORGANISM: Rattus norvegicus
<220> FEATURE:
<221> NAME/KEY: unsure
<222> LOCATION: (1)..(43)
<223> OTHER INFORMATION: unsure at all n locations

<400> SEQUENCE: 17
gatccctgag atgccctaga tcaatgncat gactatgaca tta                        43

<210> SEQ ID NO 18
<211> LENGTH: 426
<212> TYPE: DNA
<213> ORGANISM: Rattus norvegicus

<400> SEQUENCE: 18
gatccgtggc ccatgagaac acatccaatg ctgagacctg tggaggagtc agcaactggg      60
attgaaagga tcagcagggt tagaccacat ggagctgtag ctggccacag ctaagactca    120
gaagaccata ggcctgacac aggatgtcag tcaatgtcac agaatggatt tgaacactct    180
gtagtggact gtgtacggct aaacacaggg actcttctac aaccagggaa tgctggagct    240
gttctctgtg aaggccacac ccctgagtgt ccagtccttc cctgggctcc tcatatgaga    300
gctaggcatt gtctgatgtg gtgaccctgc agggacagcc ctttgttctt gacagccaca    360
```

-continued gccttcagtg agcctggatt tcctgtgtgc tttcctagga agttctccct ggatgactgc        420
tggtta        426

<210> SEQ ID NO 19
<211> LENGTH: 212
<212> TYPE: DNA
<213> ORGANISM: Rattus norvegicus

<400> SEQUENCE: 19
atccgttttg tccgcgaggg aaacagagcc gttgaccatg gttgcaacgg gcagtttgag        60
cagtaagaac acggccagca tttcagagtt gctggacggt ggctctcacc ctgggagtct       120
gctaagtgat ttcgactact gggattatgt cgtccccgag cccaacctca acgaggtggt       180
gtttgaagag acaacatgcc agaatttggt ta       212

<210> SEQ ID NO 20
<211> LENGTH: 215
<212> TYPE: DNA
<213> ORGANISM: Rattus norvegicus

<400> SEQUENCE: 20
gatccgagag taggtccacc ctgctggctc tgtgactgcg gggcttggat ttataacagg        60
agaaaaaggc ggcggctgat cttctaggct gcaaacgggt gtctctggcc atccctggat       120
actggctgga gaggagacag cgtcttcaca gttgtacttg tagccttcac aggtcaggct       180
gcgtctgccc actcctgtcc attgtacgtg cgtta       215

<210> SEQ ID NO 21
<211> LENGTH: 286
<212> TYPE: DNA
<213> ORGANISM: Rattus norvegicus

<400> SEQUENCE: 21
gatcctaaag gcggtcacat ggttcctgct gaccaaggga catggctctg aagatgatga        60
ggctggttac tcagcaggag tagctgagct gagctggccc tggaggcctg gagcctggag       120
gccctggagt agggcccagg atgcaggtgc taatgtctat ccccggcgct cttcttcccg       180
actctaccat gggatgtaac tccaggaccc ctgccatctc cggtaccaaa agactgtggc       240
ttccgtgtct actcagaaat cagttctact tcgtaaacag tgttta       286

<210> SEQ ID NO 22
<211> LENGTH: 227
<212> TYPE: DNA
<213> ORGANISM: Rattus norvegicus
<220> FEATURE:
<221> NAME/KEY: unsure
<222> LOCATION: (1)..(227)
<223> OTHER INFORMATION: unsure at all n locations

<400> SEQUENCE: 22
gatcctaagg agtaaattga gaaaccaaga gtgggggaga tgaggcgcaa cccaagaaag        60
atgctgtgat ctctgaaggg acaactctaa aatcaaagtg ctggaaggtt ggctccatcc       120
tgagntnctc ttcgcattgc aagtgttgtg tttgtcctgt gccttatgct cttctctcat       180
acctgcaaag gatgcatgta tacttgcttc tcaactcctc ctgttta       227

<210> SEQ ID NO 23
<211> LENGTH: 51
<212> TYPE: DNA
<213> ORGANISM: Rattus norvegicus

```
<220> FEATURE:
<221> NAME/KEY: unsure
<222> LOCATION: (1)..(51)
<223> OTHER INFORMATION: unsure at all n locations

<400> SEQUENCE: 23
gatccttggt gtgtgacctg tcntgttgta tagccgctct gtgtatgttt a            51

<210> SEQ ID NO 24
<211> LENGTH: 83
<212> TYPE: DNA
<213> ORGANISM: Rattus norvegicus

<400> SEQUENCE: 24
gatcctatta tagatggctg caaggcacca atgtagttac tgggaattga actcaggacc   60
tctagaagac agtcagtgcc tta                                           83

<210> SEQ ID NO 25
<211> LENGTH: 322
<212> TYPE: DNA
<213> ORGANISM: Rattus norvegicus
<220> FEATURE:
<221> NAME/KEY: unsure
<222> LOCATION: (1)..(322)
<223> OTHER INFORMATION: unsure at all n locations

<400> SEQUENCE: 25
gatcctacac tttcctagaa acctgaaaca ttggaatcat tnctactatt tgcagtcata   60
gcaactgcat tcatgggcta tgtactccca tgaggacaaa tatcattctg aggagctaca  120
gtaattacaa acctattatc agctatccct tacattggga ctaccctagt cgaatgaatc  180
tgaggaggct tctcagtaga caaagcaacc ctaaacgct tcttcgcatt ccacttcatc   240
ctcccattca ttatcgccgc ccttgcaatt gtacatcttc ttttcctcca cgaaacagga  300
tcaaataacc ccacanggat ta                                           322

<210> SEQ ID NO 26
<211> LENGTH: 178
<212> TYPE: DNA
<213> ORGANISM: Rattus norvegicus
<220> FEATURE:
<221> NAME/KEY: unsure
<222> LOCATION: (1)..(178)
<223> OTHER INFORMATION: unsure at all n locations

<400> SEQUENCE: 26
gatcctgaac aaccttccac tcctgcagga ctaaattcaa cagcgaaaat cctgaaacca   60
tcagtttcct gcaaagccgt tgagagagtc acagaccacc tccttacgga tctcagacct  120
ggacagagaa cagttcaaac tcngggagat gcaaagccgg tatgagcaac ctgcatta    178

<210> SEQ ID NO 27
<211> LENGTH: 275
<212> TYPE: DNA
<213> ORGANISM: Rattus norvegicus

<400> SEQUENCE: 27
gatctacctg cgtctcaaaa agctccaata atcttgacag cacaagacag ctccaacagc   60
atgctgtctg ccatttgtct ttctgtcagt cactcttgtc cccactccat ctgctcacat  120
ctcattcttt cttctcacct tgttcacctc cacccacctt ctgctgtgct tctggtctcc  180
ttgtctgtca gtctttctat ctcgacttct ggaatttcta cctgcttttc tctctacctg  240
```

```
gcccctacct gacttcatgt ttgaccttga cctta                              275
```

<210> SEQ ID NO 28
<211> LENGTH: 69
<212> TYPE: DNA
<213> ORGANISM: Rattus norvegicus

<400> SEQUENCE: 28

```
gatctcaatt tgatgtcatt ctcgcagatg ctgtgggtcc ctgtggtgag ctgctagcta   60
gaatgctta                                                          69
```

<210> SEQ ID NO 29
<211> LENGTH: 48
<212> TYPE: DNA
<213> ORGANISM: Rattus norvegicus

<400> SEQUENCE: 29

```
gatctctcta tagaccagaa acatgatatg tggaccatgc tggcctta               48
```

<210> SEQ ID NO 30
<211> LENGTH: 308
<212> TYPE: DNA
<213> ORGANISM: Rattus norvegicus
<220> FEATURE:
<221> NAME/KEY: unsure
<222> LOCATION: (1)..(308)
<223> OTHER INFORMATION: unsure at all n locations

<400> SEQUENCE: 30

```
gatctcagag acggccatga tcttcgccgg cgtggatgtc accaaggagc ccattccagt   60
ccttcccact gtgcattaca acatgggcgg gnntcccact aactacaagg gacaggtgct  120
gaagcacgtg aacggccagg atcagattgt gcctggtctg tacgcctgtg gggaggctgc  180
ctgcgcctca gtgcatggtg ccaaccggct tggagcaaac tctcttttgg accttgtcgt  240 cttttggccga gcctgtgccc tgagcattgc agaatcttgc aggcctggag ataaagttcc  300
tccgatta                                                          308
```

<210> SEQ ID NO 31
<211> LENGTH: 221
<212> TYPE: DNA
<213> ORGANISM: Rattus norvegicus
<220> FEATURE:
<221> NAME/KEY: unsure
<222> LOCATION: (1)..(221)
<223> OTHER INFORMATION: unsure at all n locations

<400> SEQUENCE: 31

```
gatctccaac tgcatgccag agtaacggag agactttgac agcccaggtt atcacagtgc   60
ctgctgttgc cactcagctc tcctatatgt ttttccactg gagttatgag ctgcctgtcc  120
ttctgtcctg tggtattcaa acaaactttt ccttctgcag tgtgcacttg ggggcggttc  180
ttggnntant gaggagacag cctgtcagcc tctgcccatt a                     221
```

<210> SEQ ID NO 32
<211> LENGTH: 186
<212> TYPE: DNA
<213> ORGANISM: Rattus norvegicus

<400> SEQUENCE: 32

```
gatctccgtg atgtcaagat ttgactccgg ttttcactaa acctgacctt tacagtgctc   60
aactctgcct acagggtgct tgcttattga tagtgaatta tcatttcttg tggtgtcttc  120
```

```
atccatgtct ataactttct tagaacatca tgaaatggtt actttactac atgatttata      180
acatta                                                                186

<210> SEQ ID NO 33
<211> LENGTH: 146
<212> TYPE: DNA
<213> ORGANISM: Rattus norvegicus

<400> SEQUENCE: 33
gatctcatcc tcccggaagg gttgctaggc ttctgtgtgg aaactgtggc gtcagcagcc      60
agagcacatg ctcctggccc agggctctca ggctcactct cacctcatgt attttgtctc      120
tgctcgtagg aaaatcatcg tcatta                                          146

<210> SEQ ID NO 34
<211> LENGTH: 125
<212> TYPE: DNA
<213> ORGANISM: Rattus norvegicus

<400> SEQUENCE: 34
gatctcggag gccataatcc gggtcttcct gtgcaagtct tcctgcctct tcaacaggca      60
agtttttgat gccctggtca gtcttgtaat ggaacttgca gtacactgcc tctccattcg      120
catta                                                                 125

<210> SEQ ID NO 35
<211> LENGTH: 49
<212> TYPE: DNA
<213> ORGANISM: Rattus norvegicus
<220> FEATURE:
<221> NAME/KEY: unsure
<222> LOCATION: (1)..(49)
<223> OTHER INFORMATION: unsure at all n locations

<400> SEQUENCE: 35
gatctgacac tctcccgaga cacccacaaa gaggatngtg ctgtgttta                 49

<210> SEQ ID NO 36
<211> LENGTH: 193
<212> TYPE: DNA
<213> ORGANISM: Rattus norvegicus

<400> SEQUENCE: 36
gatctgagga gtgtacagca aaggctttga ctttcctttg tggtggaagg atttggtttt      60
ttcattggcc acggaacgac tacaaatagt ggcgagatgc tgccctctgg tggcccgaaa      120
cgttgaactc ggttgtatag gtggattgat tacaacagtc aactcccagg gtctgacttt      180
ctaatccgcg tta                                                        193

<210> SEQ ID NO 37
<211> LENGTH: 205
<212> TYPE: DNA
<213> ORGANISM: Rattus norvegicus
<220> FEATURE:
<221> NAME/KEY: unsure
<222> LOCATION: (1)..(205)
<223> OTHER INFORMATION: unsure at all n locations

<400> SEQUENCE: 37
gatctgagtt cagacatcaa ggaaaagttt gcaaaactat gtgtggcaca tggaatcact      60
agggacaata tcattgacct aaccaagact gatcgctgtc tccaggcccg aggttgaaga      120
```

-continued

```
aaggcctgag cctccagatt gcagggcaag atccagtgag agcaagantg cttctctgtc      180
cagaagtcaa tccaagaagt gctta                                            205

<210> SEQ ID NO 38
<211> LENGTH: 177
<212> TYPE: DNA
<213> ORGANISM: Rattus norvegicus

<400> SEQUENCE: 38
gatctgagtt cagacatcaa ggaaaagttt gcaaaactat gtgtggcaca tggaattcac       60
tagggacaat atcattgacc taaccaagac tgatcgctgt ctccaggccc gaggttgaag      120
aaaggcctga gcctccagag tgcctctctg tccagaagtc aatccaagaa gtgctta        177

<210> SEQ ID NO 39
<211> LENGTH: 157
<212> TYPE: DNA
<213> ORGANISM: Rattus norvegicus

<400> SEQUENCE: 39
gatctggtca tgttgctggt gctcactctc acctgtctta ttctcctgtc aatctggaga       60
cagagttctg ggagaggaaa gctcccccag gcctattcct ctcccaatta ttggcaatat      120
ctttcagcta aatgtgaaga acatcaccca atcctta                              157

<210> SEQ ID NO 40
<211> LENGTH: 413
<212> TYPE: DNA
<213> ORGANISM: Rattus norvegicus

<400> SEQUENCE: 40
gatctggtat gaacacaggc tcatagatga catggtggcc caggctatga aatcagaagg       60
aggcttcatc tgggcctgta agaactatga tggtgatgtg cagtcagact cagtagccca      120
aggttatggc tcccttggca tgatgaccag tgtgctgatt tgtccagatg gtaagacggt      180
agaagcagag gctgcccatg gcactgtcac acgtcactac cgcatgtacc agaaaggaca      240
ggagacgtcc accaatccca ttgcttccat ttttgcctgg tcccgagggt tagcccacag      300
agcaaagctt gacaacaata ctgagctcag cttctttgca aatgctttgg aagaagtctg      360
cattgagacc attgaggctg gctttatgac taaggacttg gctgcttgca tta             413

<210> SEQ ID NO 41
<211> LENGTH: 346
<212> TYPE: DNA
<213> ORGANISM: Rattus norvegicus

<400> SEQUENCE: 41
gatctggggt aaccaaaggc ggcctttgaa tttgccacgt agctgaggct ggccttgaac       60
tccttaccct cttgcctcta tagagaaagt gctgggattg caggcagatg acacacctgt      120
ccaacaactg gttcataaag gcagatgcag ggtacttcac acacactggg ctgggcagct      180
gggactgcca gggagaggtc cttagcatac atgaaagtgg acaggacag ctctggggtt       240 taggcaggaa tagacaaagg tgacaagcct cacgacctca gggacaggag tccctgtgag      300
ggccctgcct acctcctgta tctcccctct cccctgtcag ccatta                    346

<210> SEQ ID NO 42
<211> LENGTH: 292
<212> TYPE: DNA
<213> ORGANISM: Rattus norvegicus
```

```
<400> SEQUENCE: 42
gatcttacgg aacttctacc acgagaacat tgtgaagtat aaaggaatct gcatggaaga    60
cggagggaat ggtatcaagc tcatcatgga gtttctgcct tcgggaagcc taaaggaata   120
tctgccaaag aataagaaca aaatcaacct caaacagcag ctaaaatatg ccatccagat   180
ttgtaagggg atggactatc tgggctctcg gcaatatgtt caccgggact agcagcaag    240 aaatgtcctt gttgagagtg aacaccaagt gaagatcgga gactttggtt ta           292

<210> SEQ ID NO 43
<211> LENGTH: 239
<212> TYPE: DNA
<213> ORGANISM: Rattus norvegicus

<400> SEQUENCE: 43
gatcccattg gcaggagagg gaggtagcct ttgctacgaa acaagccatc cccagactca    60
acagctaacc aagtattcac gtacccgtga ttctgtgggt tagctaagct cctttgagca   120
gctctactag tgtggcctgg tcctgctcat gagcccagtc acttctcact tcagctgggg   180
ctggttaggc tggggtcacc cagccattgt agcaagtgtt ggttgcatcg gcttggtta    239

<210> SEQ ID NO 44
<211> LENGTH: 121
<212> TYPE: DNA
<213> ORGANISM: Rattus norvegicus
<220> FEATURE:
<221> NAME/KEY: unsure
<222> LOCATION: (1)..(121)
<223> OTHER INFORMATION: unsure at all n locations

<400> SEQUENCE: 44
gatcccaagc ggcgctcctg tcagacagca ttggcggaan tctggatgtg ttggtccgtt    60 cttttttgcgc cgttcttcct tcacttggca gaagaagtgt gccagcacat cccctacgtt   120
a                                                                   121

<210> SEQ ID NO 45
<211> LENGTH: 117
<212> TYPE: DNA
<213> ORGANISM: Rattus norvegicus
<220> FEATURE:
<221> NAME/KEY: unsure
<222> LOCATION: (1)..(117)
<223> OTHER INFORMATION: unsure at all n locations

<400> SEQUENCE: 45
gatcccaacg tcaagtcaat ctttgtcacc tgtggagacn ggacttgaaa gtcatgcttc    60
caggccagtg ccattattta ggcttgcagt ggcgggatta cttcaagcag tggatta      117

<210> SEQ ID NO 46
<211> LENGTH: 105
<212> TYPE: DNA
<213> ORGANISM: Rattus norvegicus
<220> FEATURE:
<221> NAME/KEY: unsure
<222> LOCATION: (1)..(105)
<223> OTHER INFORMATION: unsure at all n locations

<400> SEQUENCE: 46
gatccagttc caggatgtgt gtccttgatc cttctctctt gcctgctggc actgacnagt    60
gcccatgaca agccttcctt tcaccactgt cggacgacat gatta                   105
```

```
<210> SEQ ID NO 47
<211> LENGTH: 52
<212> TYPE: DNA
<213> ORGANISM: Rattus norvegicus
<220> FEATURE:
<221> NAME/KEY: unsure
<222> LOCATION: (1)..(52)
<223> OTHER INFORMATION: unsure at all n locations

<400> SEQUENCE: 47
gatcctatgt gtctcnaaga ataagcacac tcagactaac acagtcccat ta          52

<210> SEQ ID NO 48
<211> LENGTH: 442
<212> TYPE: DNA
<213> ORGANISM: Rattus norvegicus

<400> SEQUENCE: 48
gatctcgaga cggatagcct cattcagacg accatccgaa aggagttctc ccagtgcacg   60
gtcatcacca tcgctcacag gctgcacacc atcatggaca gtgacaagat aatggtccta  120
gacaacggga agattgtcga gtatggcagt cctgaagaac tgctgtccaa cagaggttcc  180
ttctatctga tggccaagga agccggcatt gaaaatgtga atcacacaga agctctagca  240
gctggttccg tggctggcgg gactataaga acagtttcta ttatttgctt tgggtttctg  300
tgactgtgct ctaggtgcaa agacacatat tttgttcccg ttgctcaggc tgggcctcaa  360
actctaaggt ccagcaatct ctggtctcag ccagagacct gtaaaaatag acacttcaaa  420
gattatcatg aataaatatt ta                                           442

<210> SEQ ID NO 49
<211> LENGTH: 227
<212> TYPE: DNA
<213> ORGANISM: Rattus norvegicus
<220> FEATURE:
<221> NAME/KEY: unsure
<222> LOCATION: (1)..(227)
<223> OTHER INFORMATION: unsure at all n locations

<400> SEQUENCE: 49
gatctacgga ggacggcaga gaaacggtgt caggcccagc cacttcagca gaggctctaa   60
gagtgtggcc cgccgggtcc tccaagccct ggangggctg aaaatggtgg aaaaggacca  120
agatggggcc gcaagctaac acctcaggga cagagagatc tggacaggat cgccggacag  180
gtggcatgct gccaacaaga agcattagaa caaaggatgc tgggtta                227

<210> SEQ ID NO 50
<211> LENGTH: 248
<212> TYPE: DNA
<213> ORGANISM: Rattus norvegicus
<220> FEATURE:
<221> NAME/KEY: unsure
<222> LOCATION: (1)..(248)
<223> OTHER INFORMATION: unsure at all n locations

<400> SEQUENCE: 50
gatccacccc nggctaactn ttnacgannn tgcggagccc ctataaagtg cctntgacca   60
acggacacaa gaggaatatc ccctggaagt gaaccaagtg gaaagaatga gctgtgagac  120
tggatagtta tggtgcctca agctgatcct tctgagtggg cggggctagc accccagtgt  180
ccatcaagca aggtctatcc ttctgagtgg gcaggctagc actccagtgt ccagnnattc  240
cagtctta                                                           248
```

<210> SEQ ID NO 51
<211> LENGTH: 113
<212> TYPE: DNA
<213> ORGANISM: Rattus norvegicus
<220> FEATURE:
<221> NAME/KEY: unsure
<222> LOCATION: (1)..(113)
<223> OTHER INFORMATION: unsure at all n locations

<400> SEQUENCE: 51

```
gatccaactt nncagnnaan tgggagctan ctatctggaa tccacagctt gatgatttnt      60
acatcggaaa gtactttggg aggntgttgg agtatttnnt gattcaagcc tta           113
```

<210> SEQ ID NO 52
<211> LENGTH: 198
<212> TYPE: DNA
<213> ORGANISM: Rattus norvegicus
<220> FEATURE:
<221> NAME/KEY: unsure
<222> LOCATION: (1)..(198)
<223> OTHER INFORMATION: unsure at all n locations

<400> SEQUENCE: 52

```
gatccctaca agaggnagac aanacttcaa catagtgtgt gagctattct cttcggtccg      60
atcataccta gtagtttgag ccctctacct tgagaaatcc agatggatga agaaaagata    120
gctaacagct accagagggt gcatttggat gaaggaataa catctaatgt tntacaggat    180
aacnntaact gacaatta                                                   198
```

<210> SEQ ID NO 53
<211> LENGTH: 166
<212> TYPE: DNA
<213> ORGANISM: Rattus norvegicus
<220> FEATURE:
<221> NAME/KEY: unsure
<222> LOCATION: (1)..(166)
<223> OTHER INFORMATION: unsure at all n locations

<400> SEQUENCE: 53

```
gatcccatcg ctcangcngc anntcaggtg cantcctgga gagagatccc aaaattcttc      60
aggcaacacc tccttcagtc tggagnnaac tctaaatagt gtgaccatgt aggacagagt    120
aaagggcagg gagtgaatta gagaagagtt ggnngtctgg ggatta                   166
```

<210> SEQ ID NO 54
<211> LENGTH: 190
<212> TYPE: DNA
<213> ORGANISM: Rattus norvegicus
<220> FEATURE:
<221> NAME/KEY: unsure
<222> LOCATION: (1)..(190)
<223> OTHER INFORMATION: unsure at all n locations

<400> SEQUENCE: 54

```
gatccgagga catnctnctg gattcacaac tcttcaacct caggacggcg acgtcgctca      60
atggggattg gtttttcgat tgtcgtggcc tctgacaaaa gagaaaagat agaagagaac    120
ggcagcatga gagtttttgt gcagcacatc gatgtcttgg agaattcctt aggctncnag    180
ttccgtatta                                                            190
```

<210> SEQ ID NO 55
<211> LENGTH: 178
<212> TYPE: DNA

<213> ORGANISM: Rattus norvegicus
<220> FEATURE:
<221> NAME/KEY: unsure
<222> LOCATION: (1)..(178)
<223> OTHER INFORMATION: unsure at all n locations

<400> SEQUENCE: 55

```
gatcctagtt cagggnnggc tgnaggtaaa agctgttcta cagtcactct cttcctaata    60
cagtgctgtg acgtnacttc taatagacga naattagana cagcctgctt gcccataaca   120
ggaaagtgat cactgagatg atagcgtgtc catttgatgg gccnnctcag caacgtta     178
```

<210> SEQ ID NO 56
<211> LENGTH: 240
<212> TYPE: DNA
<213> ORGANISM: Rattus norvegicus
<220> FEATURE:
<221> NAME/KEY: unsure
<222> LOCATION: (1)..(240)
<223> OTHER INFORMATION: unsure at all n locations

<400> SEQUENCE: 56

```
gatcctatgt tccgnccgaa catacctgtg tgagtgaaat atgnanttct gaaaggatng    60
gctcaacaac tacagaacgc acctcccggt ctctctgctc taagatgcta aatatgaaag   120
ccagngtttc acagcccaga tcatccacng cactgcttta ctgattcgga agtttctctt   180
gaggatactc cagatacacc tgagacatta tanatcatat atcaannngc acaaatatta   240
```

<210> SEQ ID NO 57
<211> LENGTH: 222
<212> TYPE: DNA
<213> ORGANISM: Rattus norvegicus
<220> FEATURE:
<221> NAME/KEY: unsure
<222> LOCATION: (1)..(222)
<223> OTHER INFORMATION: unsure at all n locations

<400> SEQUENCE: 57

```
gatctacagg angancaagc ttngtntang tattgatgag gatgatccta ctgtggatga    60
taccagtgct gctgtaactg aagaaatgcc acccctggaa ggagatgatg acacatcacg   120
catggaagaa gtagactagg cttcaccagn actatgtgtt tgatgcttac cttcattcct   180
tctgatnata tattttccat gattttngnt ttattttgt ta                      222
```

<210> SEQ ID NO 58
<211> LENGTH: 112
<212> TYPE: DNA
<213> ORGANISM: Rattus norvegicus
<220> FEATURE:
<221> NAME/KEY: unsure
<222> LOCATION: (1)..(112)
<223> OTHER INFORMATION: unsure at all n locations

<400> SEQUENCE: 58

```
gatctagaaa gcacnnncag tttctggant tatagcacaa atccacttgt attatctctt    60
tcatatnaca atttatgntc ccttgtgtca ttgtgnnccc attcctgagt ta          112
```

<210> SEQ ID NO 59
<211> LENGTH: 176
<212> TYPE: DNA
<213> ORGANISM: Rattus norvegicus
<220> FEATURE:
<221> NAME/KEY: unsure
<222> LOCATION: (1)..(176)
<223> OTHER INFORMATION: unsure at all n locations

<400> SEQUENCE: 59
gatctccttg cangcttgac cctgtngcag taggcaccaa ggagaattac agtctcctga      60
gaagaaagct agnacaaatg cagaagaaag atgtctgatc tgcccttcat gttgngagtt     120
tgtgagtgtg tgcatgangc ctctgttcag atcntgtgct nnngtttagc cattta          176

<210> SEQ ID NO 60
<211> LENGTH: 91
<212> TYPE: DNA
<213> ORGANISM: Rattus norvegicus
<220> FEATURE:
<221> NAME/KEY: unsure
<222> LOCATION: (1)..(91)
<223> OTHER INFORMATION: unsure at all n locations

<400> SEQUENCE: 60
gatctcagnt tccgcctgtc tgtggaaaag gcaaaaaggc ccggtaatgg ctaccattgg      60
ggtgacacgg ggcttggnnn acacaacctt a                                     91

<210> SEQ ID NO 61
<211> LENGTH: 332
<212> TYPE: DNA
<213> ORGANISM: Rattus norvegicus
<220> FEATURE:
<221> NAME/KEY: unsure
<222> LOCATION: (1)..(332)
<223> OTHER INFORMATION: unsure at all n locations

<400> SEQUENCE: 61
gatctggacg ctgntgnctt cagtgantng ctgcctctgt gccattgaca tccacaacna      60
aacactctat cacatcacan tgtggacatt cctccttgcc ctgggacact tcntctcgga    120
gttgtttgta tttggnacag cggctcccac agttggtgtg ctggcaccct tgatggtagc    180
aagtttctca atcctgggta tgctagttgg gctccggtac ctanaagcag aaccagtatc    240
cagacagaag naaagaaatt gaggccancc ttgncagctc tgatacatca tggtnttcca    300
cctttgctct ntttanncac tctctgtcct ta                                  332

<210> SEQ ID NO 62
<211> LENGTH: 274
<212> TYPE: DNA
<213> ORGANISM: Rattus norvegicus
<220> FEATURE:
<221> NAME/KEY: unsure
<222> LOCATION: (1)..(274)
<223> OTHER INFORMATION: unsure at all n locations

<400> SEQUENCE: 62
gatctgattc agaccaagga aaatatgcaa aatatgtgag ggcgcatgga atcactaggg      60
acaatatcat tgatctaacc aagactgatc gctgtctcca ggcccgagga tgaagaaagg    120
cctgagcctc cagtggnnnn nnnnnnnnn nncaccagga ctctagcatc accatttcct     180
gtccatggag catcctgaga caaattctgc gatctgatgt ccatcctctg tcacagaaaa    240
gtgcaatcct gtctctccag ctcttcccta atta                                274

<210> SEQ ID NO 63
<211> LENGTH: 70
<212> TYPE: DNA
<213> ORGANISM: Rattus norvegicus
<220> FEATURE:
<221> NAME/KEY: unsure
<222> LOCATION: (1)..(70)

-continued

<223> OTHER INFORMATION: unsure at all n locations

<400> SEQUENCE: 63
gatcttcaat tacnnngtgn atgctactca accctgaata nanttcatag acagnccagt    60
tatctgctta                                                           70

<210> SEQ ID NO 64
<211> LENGTH: 280
<212> TYPE: DNA
<213> ORGANISM: Rattus norvegicus
<220> FEATURE:
<221> NAME/KEY: unsure
<222> LOCATION: (1)..(280)
<223> OTHER INFORMATION: unsure at all n locations

<400> SEQUENCE: 64
gatcttgggg ggnccttnnc ccctctggt ggccctgacc angcatagca gtcagaggct     60
ggccacttac tataggtnat aaggtcactg tgnccctcag caggnccaag cactgcatgt   120
agggaaggaa gggtccagga gctgtccaga gcgccattta gctctccttc tgtttaggaa   180
ataaagacag agtgtgcaaa gagaggcagt cagcactccc tcntgctcag ggaaccctgg   240
acagctgtgg acaggcatgg ggtannncta ctcttcatta                         280

<210> SEQ ID NO 65
<211> LENGTH: 202
<212> TYPE: DNA
<213> ORGANISM: Rattus norvegicus
<220> FEATURE:
<221> NAME/KEY: unsure
<222> LOCATION: (1)..(202)
<223> OTHER INFORMATION: unsure at all n locations

<400> SEQUENCE: 65
gatcttgctg ctannnagat cagcatctat gacaaacttt cagagactgt tgatttggtg    60
agacagacag gccatcagtg tggaatgtcc gagaaggcga ttgaaaagtt tatcagacag   120
ctactcgaaa agaatgactc aaagggacca ccccagtacc ctctccttat agccatgtat   180
aagtcnnctn actctgggat ta                                            202

<210> SEQ ID NO 66
<211> LENGTH: 162
<212> TYPE: DNA
<213> ORGANISM: Rattus norvegicus
<220> FEATURE:
<221> NAME/KEY: unsure
<222> LOCATION: (1)..(162)
<223> OTHER INFORMATION: unsure at all n locations

<400> SEQUENCE: 66
gatctttggg ncagtnatgt ccattctaac atttgagact gaagccgang ttctggagcg    60
ggccaatgac accacgttng gactagcagc tggggtcttt accaggacat tcagaggcgc   120
acaggtggcg gctgagctnc aggccgcnaa cgtgctacat ta                      162

<210> SEQ ID NO 67
<211> LENGTH: 57
<212> TYPE: DNA
<213> ORGANISM: Rattus norvegicus
<220> FEATURE:
<221> NAME/KEY: unsure
<222> LOCATION: (1)..(57)
<223> OTHER INFORMATION: unsure at all n locations

<400> SEQUENCE: 67

-continued gatctttata gacatgaatg cacaactcat tgaatggcaa gaannttcct gtcatta    57

<210> SEQ ID NO 68
<211> LENGTH: 131
<212> TYPE: DNA
<213> ORGANISM: Rattus norvegicus
<220> FEATURE:
<221> NAME/KEY: unsure
<222> LOCATION: (1)..(131)
<223> OTHER INFORMATION: unsure at all n locations

<400> SEQUENCE: 68
gatctttgca acnnccaaa ttctctctac cagagagtat ataattactt gagtttcttc    60
tgtagtaaan agagaatgtc ttagtgtggt tgtgagtgac agtgaaattc aatgncnnta   120
aaaggacatt a                                                       131

<210> SEQ ID NO 69
<211> LENGTH: 77
<212> TYPE: DNA
<213> ORGANISM: Rattus norvegicus

<400> SEQUENCE: 69
gatccacttc taatctggat gctgagctgg gaagacacac ccctttatca ggtcttgagt    60
gagaagacac ctgttta                                                  77

<210> SEQ ID NO 70
<211> LENGTH: 353
<212> TYPE: DNA
<213> ORGANISM: Rattus norvegicus
<220> FEATURE:
<221> NAME/KEY: unsure
<222> LOCATION: (1)..(353)
<223> OTHER INFORMATION: unsure at all n locations

<400> SEQUENCE: 70 gatcccctg tctccgcctc ctcgtgctgg gataaagctg tgcgtccagc ccccagctag    60
acactttgga actggtggtg tagccctcag tatcatcttg aacaccagtt ggggctcctg   120
cagtgccctt tgtgcttcac tgggttttgg acgaagcagt gaggcccctg cttcctgtca   180
tgtagtgact gtagtgtgct gcgtgactat ctcggtcaag tcccgtcaag aagatgaaag   240
tccacagcaa aaggcangtt cgattcccag tgcctgctca cagctgcctg tatcttgatc   300
tgcaggggac cctgtgcctc tggtttctgt ggatacaaat gtgtatgccc tta          353

<210> SEQ ID NO 71
<211> LENGTH: 187
<212> TYPE: DNA
<213> ORGANISM: Rattus norvegicus

<400> SEQUENCE: 71
gatccggaga aagcttaggg agctgcagtt gagaaattgt ctgcgtattc ttatggggga    60
gctctctaat caccacgacc atcacgatga attctgcctt atgccttgac ttcggtcatt   120
tcccctgaga ttcatactgt gattcccgct gtattcctag cccttgcatt ttcctgacat   180
gcccttta                                                           187

<210> SEQ ID NO 72
<211> LENGTH: 116
<212> TYPE: DNA
<213> ORGANISM: Rattus norvegicus

```
<400> SEQUENCE: 72
gatccgagcc tcttgtgcgt actgtgacac agaacagata tcaccagact ggagcccatc        60
atctgagccc caatgctctc tacacaccag aattctatct tttagcagtg acttta           116

<210> SEQ ID NO 73
<211> LENGTH: 147
<212> TYPE: DNA
<213> ORGANISM: Rattus norvegicus

<400> SEQUENCE: 73
gatccggtat ctattgtcct cataacacct ggctcccaag acttgattgt gaatgactag        60
gttattagca gaatgaagga tggcctcaaa cgaagaaaga tgcatcaccc tcgaggctct       120
tcagaatgct ggatagaggc ttactta                                           147

<210> SEQ ID NO 74
<211> LENGTH: 195
<212> TYPE: DNA
<213> ORGANISM: Rattus norvegicus

<400> SEQUENCE: 74
gatcctgggt gaccctccct gaagcagtga gcaccacagg ttctgctgtg gaccagagcc        60
cccctgtgga gagggagaaa gaaaggggag ccgctgacct gcaggatac agaccttccc       120 cacagcctgg cagccgcccg tttgttgcag cttattatca gactgtgggc tatcatagtt      180
catgctcgtt tctta                                                        195

<210> SEQ ID NO 75
<211> LENGTH: 100
<212> TYPE: DNA
<213> ORGANISM: Rattus norvegicus

<400> SEQUENCE: 75
gatcctagcc acatctgaag ccatgaacat aattctcatt cttacagaca cataccagcc        60
ttgaacaact tattttcctt gtatcgatag agggtgctta                             100

<210> SEQ ID NO 76
<211> LENGTH: 395
<212> TYPE: DNA
<213> ORGANISM: Rattus norvegicus

<400> SEQUENCE: 76
gatctaccac tgcagtgacc tgactgactg tgctcagctc ttcgcctcta tgaaatgtgc        60
ctgcctggtc tgtctcatcc tgtcttctga gagcgtggtt cacagacctt gtgtctgagt       120
gaagggaacc caggttcaga ttccgtttct ctgcttctgt cttttctca gcagcaggggt      180 aggaacaggc cttttgtgca catacaacag atgaagccca tgatgagtct gtgggaaaca      240
ccaacactca tgcaccctgt gggtgaccct ccctacacag cgcagagcag agagagcccg      300
ggaggtgctg caggcttcac tgagctttcc ttgcccagac tggcaaccga ctttgctctc      360
ttttgaaaga ctctagctaa agtcagcgtt gttta                                  395

<210> SEQ ID NO 77
<211> LENGTH: 56
<212> TYPE: DNA
<213> ORGANISM: Rattus norvegicus
<220> FEATURE:
<221> NAME/KEY: unsure
<222> LOCATION: (1)..(56)
<223> OTHER INFORMATION: unsure at all n locations
```

```
<400> SEQUENCE: 77
gatctacagg atgatcaagc ttggtctagg taaattgcag gntacgtgtt catttta        56

<210> SEQ ID NO 78
<211> LENGTH: 164
<212> TYPE: DNA
<213> ORGANISM: Rattus norvegicus
<220> FEATURE:
<221> NAME/KEY: unsure
<222> LOCATION: (1)..(164)
<223> OTHER INFORMATION: unsure at all n locations

<400> SEQUENCE: 78
gatctacgaa gccatttacc acggggtccn natggtgggc attcccatgt ttggtgatca        60
gccttacaac atcgctcaca tggaggccaa gggagcagcc gtgaaagtcg ccatcaacac       120
gatgaccagc gcagatttgc tcagtgcctt gagagcggtc atta                       164

<210> SEQ ID NO 79
<211> LENGTH: 207
<212> TYPE: DNA
<213> ORGANISM: Rattus norvegicus

<400> SEQUENCE: 79
gatctccacc gaactggtga agagcaagct cagggagacc actggggcag cctgcaaata        60
tggggccttt gggctgccca ccactgttgc ccacgtggat ggtaaaacct acatgctatt       120
tgggtctgac cgcatggagt tgctagctta cctgctagga gagaagtgga tgggccctgt       180
gcccccaacc ctgaatgcca gacttta                                         207

<210> SEQ ID NO 80
<211> LENGTH: 112
<212> TYPE: DNA
<213> ORGANISM: Rattus norvegicus
<220> FEATURE:
<221> NAME/KEY: unsure
<222> LOCATION: (1)..(112)
<223> OTHER INFORMATION: unsure at all n locations

<400> SEQUENCE: 80
gatctccgtc atttcttggg tgcttcacct tgagttggga actgacacat ttccaacttc        60
atgacacatc ccgggagttg ccacactagc aagagcctgg ctgnttcctt ta              112

<210> SEQ ID NO 81
<211> LENGTH: 183
<212> TYPE: DNA
<213> ORGANISM: Rattus norvegicus

<400> SEQUENCE: 81
gatctccaaa ggccagaatt tccacagaca atctcttcac aactgtttgg aaggcattta        60
gcacaattcc tgtgtgagtt ggaatgatgt atttgcttac caaagctcaa gatcatccac       120
aggacaacca cagagtccac atcaaggag agaggtggtc tttgttgatc cagactggcc        180
tta                                                                   183

<210> SEQ ID NO 82
<211> LENGTH: 118
<212> TYPE: DNA
<213> ORGANISM: Rattus norvegicus

<400> SEQUENCE: 82
```

```
gatctcctgg ttttctaaaa gactgaccaa taattcttca catgtcagaa tctgttatgt      60
ttgtctgacc tccatgggag attttgtttc tggctaaaat aaaggctaaa taagctta       118
```

<210> SEQ ID NO 83
<211> LENGTH: 264
<212> TYPE: DNA
<213> ORGANISM: Rattus norvegicus
<220> FEATURE:
<221> NAME/KEY: unsure
<222> LOCATION: (1)..(264)
<223> OTHER INFORMATION: unsure at all n locations

<400> SEQUENCE: 83

```
gatctcggaa gagctctggg tctcacttgt ttttcccata gactgaccat ccagggtccc      60
tgtggttaga tggggacagg agtttttctc ccttgccttt ctgggatgg agaagggcta      120 aaccaagncc atgttgtctg gagaggtgca cccagggggtg aaggggtctg agaggccttc    180 cacctacccct cagagagcct ggttcctca ggggctcagt ggggcagcac tttttgttat    240
tgtcgtgata agttcgtagc atta                                           264
```

<210> SEQ ID NO 84
<211> LENGTH: 60
<212> TYPE: DNA
<213> ORGANISM: Rattus norvegicus

<400> SEQUENCE: 84

```
gatctcccag gactcaagac accagttggc agaggaagag cctggcttcg gttggcatta      60
```

<210> SEQ ID NO 85
<211> LENGTH: 136
<212> TYPE: DNA
<213> ORGANISM: Rattus norvegicus

<400> SEQUENCE: 85

```
gatcttggtg agtgtcacct tttttatttt tttgttttc gagacagggt tcttctgta       60 tagccctggc tgtcttggaa ctctgtagac tgggctggct tctgactcag agctctgcct    120
gcctctgctg ggatta                                                    136
```

<210> SEQ ID NO 86
<211> LENGTH: 85
<212> TYPE: DNA
<213> ORGANISM: Rattus norvegicus

<400> SEQUENCE: 86

```
gatccaaggt atgaagacgc agagtaaacc ctcagttatc aaacggaaaa agatgggcag      60
ctaagatgca tataaagggg agcta                                            85
```

<210> SEQ ID NO 87
<211> LENGTH: 145
<212> TYPE: DNA
<213> ORGANISM: Rattus norvegicus

<400> SEQUENCE: 87

```
gatccaaaga tttctaactt ggctcccttg ggcattcctc gaaggattat caagaacaca      60
accttccgtg gcttcttcct ccccaagggc acgatgtgt tccctatatt aggttctctg     120
atgacagacc caaagttctt cccta                                           145
```

<210> SEQ ID NO 88
<211> LENGTH: 346

<212> TYPE: DNA
<213> ORGANISM: Rattus norvegicus

<400> SEQUENCE: 88

```
gatccagtaa attctcttca attccctgta gatttactaa gtgaccaccc atttcctgcc      60
ctcactaagt gacaatacct tccctgcaga cccactaata cacgcttcct tcatatccta     120
ctcaggaagt gaccatgtca actgagccct tctgactgac tgtccgactg tccttgtcaa     180
ttgccactct catgtcccct ccctctctca ctgccacact cctccatcag catgtagaga     240
gtgtcttttt caactttggt ctttcctttt gtggacaaca tttctgcaaa agagcaaggg     300
tctggaactt gccctggcct ctgaccctg gatgtgtgtg ctgcta                     346
```

<210> SEQ ID NO 89
<211> LENGTH: 205
<212> TYPE: DNA
<213> ORGANISM: Rattus norvegicus

<400> SEQUENCE: 89

```
gatccagagt tcaaggtcag ccttggatac atatgcagtt ccagaccaac ctgggatata      60
ggagacccca tctcaaaaaa acaaaccaac cctgccctcc agtaaccgtc caggagagtg     120
tggtggtgca ggctgagccg ctctataccc agcctctgag aactttgtcc tctcggcaac     180
ttgatagcct gcggttggtt ggcta                                           205
```

<210> SEQ ID NO 90
<211> LENGTH: 211
<212> TYPE: DNA
<213> ORGANISM: Rattus norvegicus

<400> SEQUENCE: 90

```
gatccagaag acatcacaaa taatcctctt gaatagtcct tgggcaactg ggccttcctg      60
acctgtatca gagagaattc tgggggcgtt cgaggcaccc tacactccat gctccagttt     120
tcagccgccc ccacctcacc cccatctctt tagtcttacc tgaggttggt tgacagcctg     180
cctatgtttt ctctgttgtc ttcctaccct a                                    211
```

<210> SEQ ID NO 91
<211> LENGTH: 166
<212> TYPE: DNA
<213> ORGANISM: Rattus norvegicus

<400> SEQUENCE: 91

```
gatccatagt atagtcctcg tcccacatgg aggaataggc agatgaaaaa tattgaggcg      60
ccgttggcgt gtaggtatcg gattagtcag ccgtagttta cgtctcggca gatgtgggtg     120
actgatgaaa atgctgttat ggtatcagac gtgtagtgta ttgcta                    166
```

<210> SEQ ID NO 92
<211> LENGTH: 148
<212> TYPE: DNA
<213> ORGANISM: Rattus norvegicus
<220> FEATURE:
<221> NAME/KEY: unsure
<222> LOCATION: (1)..(148)
<223> OTHER INFORMATION: unsure at all n locations

<400> SEQUENCE: 92

```
gatccattac actgggatga gagagactca atgattcttt gatcagccct tctacatcgc      60
tgaggtttcc tcattgcatg cgatagggtg atcatgattt ccccactaac tcattttctg     120
```

```
gctggcctct tttatanagc tcgccta                                        148
```

<210> SEQ ID NO 93
<211> LENGTH: 52
<212> TYPE: DNA
<213> ORGANISM: Rattus norvegicus

<400> SEQUENCE: 93

```
gatccatgga ggtggactaa taatagcgga gcatcaccct atagtgtgac ta             52
```

<210> SEQ ID NO 94
<211> LENGTH: 43
<212> TYPE: DNA
<213> ORGANISM: Rattus norvegicus

<400> SEQUENCE: 94

```
gatccatttc tttagcagtt gaaacagctg gccattgtaa cta                      43
```

<210> SEQ ID NO 95
<211> LENGTH: 228
<212> TYPE: DNA
<213> ORGANISM: Rattus norvegicus

<400> SEQUENCE: 95

```
gatcccagcc gtcgtggatc ctctcaccat tacttcttcc ctgtcatcgg atggagtcct     60
cactgtgaat ggaccaagga acaggcctc tggccctgag cgcaccattc ccatcacccg     120
tgaagagaag cctgctgtca ctgcagcccc taagaagtag attcccttc ctcgttgcat     180 tttttaagac aaggaagttt cccatcagcg aatgaacatc tgtgacta                 228
```

<210> SEQ ID NO 96
<211> LENGTH: 103
<212> TYPE: DNA
<213> ORGANISM: Rattus norvegicus

<400> SEQUENCE: 96

```
gatccccaag actgtggact ggagagaaaa gggttgtgtg actcctgtga agaatcaggg     60
ccagtgtggt tcttgctggg cttttagcgc atcgggttgc cta                      103
```

<210> SEQ ID NO 97
<211> LENGTH: 343
<212> TYPE: DNA
<213> ORGANISM: Rattus norvegicus

<400> SEQUENCE: 97

```
gatccccggg aacaatcttg cctcaggccc ctcccccgca actccctgcg atgcccatc     60 cccttgcct tgaaagccct tctaagctcg gcctgagaac tcctcctcac ccttcaccct     120
tcccagccca aggctccgag ggtcccatca gtgctgatga gtctggcctt tgagcttttc    180
ttgacaattc ctaatggttc taaagcctgg agccccggga actgtgagc taaggagaca     240 tagcacaaaa tcataaatga gttgcgggga gaggctggaa acagtgtgca agaaatacag    300 gccagggtt ggggatttag ctcagcggta gagcgcttgc cta                       343
```

<210> SEQ ID NO 98
<211> LENGTH: 50
<212> TYPE: DNA
<213> ORGANISM: Rattus norvegicus

<400> SEQUENCE: 98

```
gatccccatt agcttgtgcc tgtggccaga aaaggccaaa gccagcccta               50
```

<210> SEQ ID NO 99
<211> LENGTH: 48
<212> TYPE: DNA
<213> ORGANISM: Rattus norvegicus

<400> SEQUENCE: 99
gatccctggg gcttgctggc cagccagaag ctgcatctgt gagctcta      48

<210> SEQ ID NO 100
<211> LENGTH: 72
<212> TYPE: DNA
<213> ORGANISM: Rattus norvegicus

<400> SEQUENCE: 100
gatccctaca agaggaagac aagacttcaa catagtgtgt gagcctattc ttcttcggtc      60
cgatcatacc ta      72

<210> SEQ ID NO 101
<211> LENGTH: 200
<212> TYPE: DNA
<213> ORGANISM: Rattus norvegicus

<400> SEQUENCE: 101
gatccctgcc atctgcgaca tccccaccga gatgcacatt tcttttttgc ccccatccga      60
acactcaaac accctgtatt catctaaggg tctgggagag tctggggtgt tcctgggctg      120
ttcggtattt tttgccatcc atgacgcagt gagggcagcg cggcaggaga gaggcatctc      180
tggaccatgg aagctcacta      200

<210> SEQ ID NO 102
<211> LENGTH: 143
<212> TYPE: DNA
<213> ORGANISM: Rattus norvegicus

<400> SEQUENCE: 102
gatccgagag aagcaagcag caaacaaaaa cttccctttc tctgtgcatg acaaccgcca      60
ctgttttgag aactccggat actactttga ctctggcttg gggcgaagga agtgcacccc      120
agatcaaaag caacacattt cta      143

<210> SEQ ID NO 103
<211> LENGTH: 343
<212> TYPE: DNA
<213> ORGANISM: Rattus norvegicus

<400> SEQUENCE: 103
gatccgaagc aggtagccct gagtcattat ggcgctctct gacttcagca atcagcagcc      60
cttacaatcc tgcaaggatt ccacccaagt cagcagcagt cacgggcctc cttcactgat      120
gtgtgttctg cctgctcagc ccctgccaca gaggcctgga ggtgtgggag tgtggcctaa      180
gcacagtctg ccatccttga ccgcagacct cttggaccca cccccactcc ctccagacac      240
tggtaagaga agccttcctg caacatgtcc tgtcctcagg aggtgagaca gcagagtgct      300
tccattcact cgatgacccc attttttgctc ttcctttggg cta      343

<210> SEQ ID NO 104
<211> LENGTH: 41
<212> TYPE: DNA
<213> ORGANISM: Rattus norvegicus
<220> FEATURE:

<221> NAME/KEY: unsure
<222> LOCATION: (1)..(41)
<223> OTHER INFORMATION: unsure at all n locations

<400> SEQUENCE: 104
gatccgagnc aatgcgtggc atttccctct cattggccct a         41

<210> SEQ ID NO 105
<211> LENGTH: 67
<212> TYPE: DNA
<213> ORGANISM: Rattus norvegicus

<400> SEQUENCE: 105
gatccggagg aactacagag acatggatat ctacgtcaca gccaatggca ttgatgatct    60
tgctcta                                                             67

<210> SEQ ID NO 106
<211> LENGTH: 192
<212> TYPE: DNA
<213> ORGANISM: Rattus norvegicus

<400> SEQUENCE: 106
gatccgggag cattccctttt gcagtgtcat agataccgaa gtaggcagca cggtagatga   60
taatgccctg cactgacaca ttaaagcctt ggtacaggcc cttaatccca tcagatttgt   120
agatcttaac caggcagtca ccaaggcctt tgaattccct ttcagctcca gctttgccca   180
catcagctgc ta                                                       192

<210> SEQ ID NO 107
<211> LENGTH: 97
<212> TYPE: DNA
<213> ORGANISM: Rattus norvegicus

<400> SEQUENCE: 107
gatcctatga tcctgaacgg cagcctgtgc tctctgtcta ccagccagag gacaaccttg    60
gaggctctcc cgagactccc tgtactcacc cctgcta                            97

<210> SEQ ID NO 108
<211> LENGTH: 42
<212> TYPE: DNA
<213> ORGANISM: Rattus norvegicus
<220> FEATURE:
<221> NAME/KEY: unsure
<222> LOCATION: (1)..(42)
<223> OTHER INFORMATION: unsure at all n locations

<400> SEQUENCE: 108
gatcctatcg tgacctgttg gacangaagg gagtgtttgc ta        42

<210> SEQ ID NO 109
<211> LENGTH: 67
<212> TYPE: DNA
<213> ORGANISM: Rattus norvegicus

<400> SEQUENCE: 109
gatcctatct taaagtagaa tgaaatctag ggttggggat ttagctcagt ggtagagcac    60
ttgccta                                                             67

<210> SEQ ID NO 110
<211> LENGTH: 207
<212> TYPE: DNA
<213> ORGANISM: Rattus norvegicus

<400> SEQUENCE: 110

| gatcctcacc gtggaggacc actactatga aggtggcata ggcgaggcag tatctgctgc | 60 |
| ggtagtgggc gaacctggag tcacagtcac tcgcctggcg gtcagccaag taccacgaag | 120 |
| tgggaagcca gctgagctgc tgaagatgtt tggtattgac aaagacgcca ttgtgcaagc | 180 |
| tgtgaagggc cttgtcacca agggcta | 207 |

<210> SEQ ID NO 111
<211> LENGTH: 271
<212> TYPE: DNA
<213> ORGANISM: Rattus norvegicus

<400> SEQUENCE: 111

| gatcctccat gacaagggaa caggaagaaa tgataatatg aatggtggat catgaatatc | 60 |
| ttcacaatct ttccctgtga tgaattagca tctccagctc tctgcctata tagtagatat | 120 |
| ggaccacaaa gaagtaaata atggtgtgca attttgtca aggaatcttt agaggcccac | 180 |
| acaattccaa attctcactt catgtcagag attgaatgat tgaaaagctt tctgcagtaa | 240 |
| attatttacc ctattttctt agcatgtact a | 271 |

<210> SEQ ID NO 112
<211> LENGTH: 415
<212> TYPE: DNA
<213> ORGANISM: Rattus norvegicus

<400> SEQUENCE: 112

| gatcctcaaa gtggctcagg aacactttgg caaaggcaaa tcaaaagact tccaactgtt | 60 |
| cggctctcct cttgggaaag acctgctgtt taaggattct gcctttgggc tgttacgggt | 120 |
| gccccccaagg atggactaca ggctgtacct cggccacagc tatgtcactg ccattcgaaa | 180 |
| tcagcgggaa ggcgtgtgcc cggagggctc catcgacagc gcgccagtga atggtgtgc | 240 |
| actgagtcac caagagagag ccaagtgtga tgagtggagc gtcagcagca atgggcagat | 300 |
| agagtgtgag tcagcagaga gcactgagga ctgcattgac aagattgtga atggagaagc | 360 |
| agatgccatg agcttggatg gaggtcatgc ctacatagca ggccagtgtg gacta | 415 |

<210> SEQ ID NO 113
<211> LENGTH: 152
<212> TYPE: DNA
<213> ORGANISM: Rattus norvegicus

<400> SEQUENCE: 113

| gatcctctca gaacaccagt ctgtgccaat gagggagcag catggcctct gagtgaggag | 60 |
| gtgctgggtg taagaccaca ccctccagag ggaagaaagg ctcctctctg ggttgtgcgc | 120 |
| tgactttctt atactgctcc cttgtgccac ta | 152 |

<210> SEQ ID NO 114
<211> LENGTH: 295
<212> TYPE: DNA
<213> ORGANISM: Rattus norvegicus

<400> SEQUENCE: 114

| gatcctgaag agcaatgagg gacgtgccct ttcgccgcca gcaccagcgc aatgtcaagc | 60 |
| ttatgaggca gatgctaatg gacgctggcc ccccagtcat ccactgcccc agccacatca | 120 |
| tccctgtgcg ggttgcctga tgctgctaaa aacacagaaa tctgtgatga agttgatgac | 180 |

```
caggcataat atctacgtcc aggccattaa ttacccaaca gtgcctcgtg gggaggagct      240
cctccggatc gcccccaccc cgcaccacac accgcagatg atgaacttct tccta           295

<210> SEQ ID NO 115
<211> LENGTH: 76
<212> TYPE: DNA
<213> ORGANISM: Rattus norvegicus

<400> SEQUENCE: 115
gatccttgcc tgccactatt tctgtgatct caatgttttg ttttctcctg acttctgaca      60
ccaagctgat ttgcta                                                      76

<210> SEQ ID NO 116
<211> LENGTH: 290
<212> TYPE: DNA
<213> ORGANISM: Rattus norvegicus
<220> FEATURE:
<221> NAME/KEY: unsure
<222> LOCATION: (1)..(290)
<223> OTHER INFORMATION: unsure at all n locations

<400> SEQUENCE: 116
gatctaaaag tatcgccttt catgagaaag ggaattgtag gagactggag gaaccacttc      60
cctgaagccc tgagggagag atttgaggag cactaccagc ggcatatgaa ggactgccct      120
gtgaagttta gagcagagct ctgagacact tccttgtgtc tgaaattgga gtagtctcca      180
atttatcctt cagtttttct tgttttgaat tcagtagaag tagaagtctt ttgaagactg      240
atggtttaaa ttcattctgg ttttttaaac naacntttat tttaatctac                 290

<210> SEQ ID NO 117
<211> LENGTH: 228
<212> TYPE: DNA
<213> ORGANISM: Rattus norvegicus

<400> SEQUENCE: 117
gatctaacca agactgatcg ctgtctccag gcccgaggat gaagaaaggc ctgagcctcc      60
agtgctgagt ggagacttct caccaggact ccagcatcac catttcctgt ccatggagca      120
tcctgagaca aattctgcga tctgatttcc atcctctctc acagaaaagt gcaatcccgg      180
tctctccagc atcttcccta gttacccagg acaacacatc gagaatta                   228

<210> SEQ ID NO 118
<211> LENGTH: 93
<212> TYPE: DNA
<213> ORGANISM: Rattus norvegicus

<400> SEQUENCE: 118
gatctactta aaaactgctt cgtgacaaaa accacacctg aagaaatttt aagaatttgg      60
cacagttagt cactttgtgt cacccggaat cta                                   93

<210> SEQ ID NO 119
<211> LENGTH: 145
<212> TYPE: DNA
<213> ORGANISM: Rattus norvegicus

<400> SEQUENCE: 119
gatctacacc acagtttcta acagtagcaa cattacagcc atgaagtagc agtgaaaata      60
acttgatggt gggggaatc accagaatat gaggaactgt attaaagggt cgcagcattc       120
ggaaggttga gaagccactg ggcta                                            145
```

<210> SEQ ID NO 120
<211> LENGTH: 34
<212> TYPE: DNA
<213> ORGANISM: Rattus norvegicus
<220> FEATURE:
<221> NAME/KEY: unsure
<222> LOCATION: (1)..(34)
<223> OTHER INFORMATION: unsure at all n locations

<400> SEQUENCE: 120
gatctacatt ggaaggcgtn gacaactanc acta                                34

<210> SEQ ID NO 121
<211> LENGTH: 45
<212> TYPE: DNA
<213> ORGANISM: Rattus norvegicus

<400> SEQUENCE: 121
gatctaggcc cctttcctcc tctaaccttc tttctctcct gccta                    45

<210> SEQ ID NO 122
<211> LENGTH: 363
<212> TYPE: DNA
<213> ORGANISM: Rattus norvegicus
<220> FEATURE:
<221> NAME/KEY: unsure
<222> LOCATION: (1)..(363)
<223> OTHER INFORMATION: unsure at all n locations

<400> SEQUENCE: 122
gatctcattg gtgcagggac agagacaatg agcacaacat tgagatatgc tctcctgctt    60
ctgatgaagt accncacatg tcacagctaa agtccaggaa gagattgacc gtgtgattgg   120
cagacatcgc agcccctgca tgcaggatag aaaacacatg ccctacacag atgccatgat   180
tcatgaggta ncagagattc attaactttg tcccgaccaa cctgccccat gcagtgacct   240
gtgacattaa attcaggaac tacctcatcc cgaagggaac aaaagtgtta acatcactga   300
catcagtgct gcatgacagc aaggagttcc ccancccana gatgtttgcc cnanccactt   360
cta                                                                 363

<210> SEQ ID NO 123
<211> LENGTH: 132
<212> TYPE: DNA
<213> ORGANISM: Rattus norvegicus

<400> SEQUENCE: 123
gatctcaggg gaggtatgct taaggccaga gctcttcctc agtatttgat ttttccagtg    60
tttgtttttt taaaaactga caggtgctac atttctatct gttggtttca attctgccat   120
atttcatgtc ta                                                       132

<210> SEQ ID NO 124
<211> LENGTH: 89
<212> TYPE: DNA
<213> ORGANISM: Rattus norvegicus

<400> SEQUENCE: 124
gatctcagca gcctggttgt cacagtagaa taagaatggc tggccttaac cttccctgtg    60
agtgacgtga atgaatgcct acctggcta                                      89

<210> SEQ ID NO 125

<211> LENGTH: 206
<212> TYPE: DNA
<213> ORGANISM: Rattus norvegicus

<400> SEQUENCE: 125

```
gatctcattg atcacagcct gggtgtaggg catcttcatg tggtcctcat actgaggctg      60
tcggttcctg ccgatcacct gctcaatttc ctcatggacc ttggcctcca catctggatg     120
cttcatgagt agaaggaagc cgtagcgtag tgtggagctg actgtctcag acccagcaaa     180
gaagaggctt agtgttgtca tcacta                                          206
```

<210> SEQ ID NO 126
<211> LENGTH: 71
<212> TYPE: DNA
<213> ORGANISM: Rattus norvegicus

<400> SEQUENCE: 126

```
gatctcccag atcaagtcct ctttgccatc tccatttcga gccacaacag catgagaagg      60
gatccgggct a                                                           71
```

<210> SEQ ID NO 127
<211> LENGTH: 129
<212> TYPE: DNA
<213> ORGANISM: Rattus norvegicus

<400> SEQUENCE: 127

```
gatctcccgg ggagtgatgc tggaagaaag gcaaagccag aaactcaata agtatgacg       60
tttaacgtgt ggcctccagg tgctttctta ctgtttgcca aaattgagct gcctcaagac     120
aaggtacta                                                             129
```

<210> SEQ ID NO 128
<211> LENGTH: 247
<212> TYPE: DNA
<213> ORGANISM: Rattus norvegicus

<400> SEQUENCE: 128

```
gatctctccc gagagacaca gccagaatac agcaaataca taggcaaatg ccagcagcaa      60
accaccgaac tgaaaacggg accccgtttt aaggaatcag agaaaggact ggaagagctt     120
gaagggcttt gagaccccat atgaacaatg ccaagcaacc agagcttcca gaaactaagc     180
cactacccaa agactgtaaa tggactgacc ctgggctcca acctcatagg tagcaatgaa     240
tagccta                                                               247
```

<210> SEQ ID NO 129
<211> LENGTH: 347
<212> TYPE: DNA
<213> ORGANISM: Rattus norvegicus

<400> SEQUENCE: 129

```
gatctctgcc tacatgaaga gcagccgcta cctctcaaca cctatatttt cgaagttggc      60
ccaatggagt aacaagtagg cccttgctac actgggcact cacagagagg acctgtccac     120
attggatcct gcaggcaccc tggccttctg cactgtggtt ctctctcctt cctgctccct     180
tctccagctt tgtcagcccc atctcctcaa cctcaccccca gtcatgccca catagtcttc    240
attctcccca ctttctttca tagtggtccc cttctttatt gacaccttaa cacaacctca     300
cagtcctttt ctgtgatttg aggtctgccc tgaactcagt ctccta                    347
```

```
<210> SEQ ID NO 130
<211> LENGTH: 431
<212> TYPE: DNA
<213> ORGANISM: Rattus norvegicus
<220> FEATURE:
<221> NAME/KEY: unsure
<222> LOCATION: (1)..(431)
<223> OTHER INFORMATION: unsure at all n locations

<400> SEQUENCE: 130
gatctgactg aaatgattat gcaattggta atatgtcccc cagaccaaaa agaagccaag      60
accgccttgg caaaagacag gaccaaaaac cggtacttgc ctgcctttga aaaggtgttg     120
aagagccatg gccaagacta ccttgtaggt aacaggctga cccgggtaga catccacctg     180
ctggaacttc tcctctatgt tgaagagttt gatgccagcc ttctgacctc tttccctctg     240
ctgaaggcct tcaagagcag aatcagcagc ctccccaatg tgaagaagtt cctgcagcct     300
ggcagtcaga gaaagcttcc cgtggatgca aaacaaatcg aagaagcang gaagattttc     360
aagttttagc ggagctgcac tgtccaattt ctttatgctt tgcanaaaat gagaagcaat     420
tgttgatcct a                                                         431

<210> SEQ ID NO 131
<211> LENGTH: 180
<212> TYPE: DNA
<213> ORGANISM: Rattus norvegicus

<400> SEQUENCE: 131
gatctggatg aaatagttct ccattaccct tacattcccc ctggggagaa agaggcaagt      60
cttgccaaaa tcaaggacaa agcaaggaac cgttactttc ctgcctttga aaaggtgttg     120
aagagccatg gacaagatta tctcgttggc aataggctga gcagggctga tgtttaccta     180

<210> SEQ ID NO 132
<211> LENGTH: 156
<212> TYPE: DNA
<213> ORGANISM: Rattus norvegicus

<400> SEQUENCE: 132
gatcttactg tgcacagctt tagatcatga tgtttagcag attgtaactt ccattcatga      60
gaagaaactg cacaaaccat ctcattcctg tcttatcttt attgtattgg aagctttctt     120
taagttacca tattttagag cgttgttagt gccta                                156

<210> SEQ ID NO 133
<211> LENGTH: 187
<212> TYPE: DNA
<213> ORGANISM: Rattus norvegicus

<400> SEQUENCE: 133
gatcttcagt taattcagtc agctatggat acactgtacc cacaaagcca gcctcagaaa      60
gctctgcaac aatgaagtat tttgactaaa tgttgaccgt acttattggg agggtaacat     120
gttttctaag gcttctgtgt taattcatat agacatgact catgaggaat tgctgggatg     180
ccatcta                                                              187

<210> SEQ ID NO 134
<211> LENGTH: 295
<212> TYPE: DNA
<213> ORGANISM: Rattus norvegicus

<400> SEQUENCE: 134
```
gatcttggta acctgacgga agcacagaga ctgcagaatg ttggcaatgc cagagaatat    60
gttcctgtgg gaaaggtccc agatacacac tccagagcta actctgaaac gtcaagaaat   120
caaagcccag aatctcgtgt aggcgaatgg agactcccca aggacacga aacagctgtt   180 aaagtagcgg gcagtgtgtc cgagaagctg ccctccagca gcctgctcat ggacagagct   240
gaagcagcca gccttgcaca gtcggcaggc cacgaggact gggaagtggt gtcta         295

<210> SEQ ID NO 135
<211> LENGTH: 93
<212> TYPE: DNA
<213> ORGANISM: Rattus norvegicus

<400> SEQUENCE: 135
gatcttggca aggggaatgg tcagcatcag cccttgtcct cagcctgtgc tttgagtcct    60
tgtccccatc cctcacactt tccctccatg cta                                  93

<210> SEQ ID NO 136
<211> LENGTH: 156
<212> TYPE: DNA
<213> ORGANISM: Rattus norvegicus

<400> SEQUENCE: 136
gatcttgaga ggtgccctgg gatgaatgcc gtttacagtg tgcatgtcct ttgaggtgtg    60
ttggaaaagt gcagcgaatt ttaacgtatg tgatccgcca tgctgtgaaa acactattgg   120 gataccctccc ctgtgacggt attggaggtt tggcta                            156

<210> SEQ ID NO 137
<211> LENGTH: 73
<212> TYPE: DNA
<213> ORGANISM: Rattus norvegicus

<400> SEQUENCE: 137
gatcttgttc atcacatgac ctcttgcggt ggtcacaggg agtaaaaatg tgtccctgtc    60
ctgttgtcag cta                                                        73

<210> SEQ ID NO 138
<211> LENGTH: 137
<212> TYPE: DNA
<213> ORGANISM: Rattus norvegicus

<400> SEQUENCE: 138
gatcttgaag ttttcatgat ttttaagagt cagaatcttt tgtgatgatt cacagtacgc    60
ttagaataag gtgattttg tttagcccac agactcatgg gagtagatta gtgtaagtta   120
ggatgaactt caccta                                                    137

<210> SEQ ID NO 139
<211> LENGTH: 125
<212> TYPE: DNA
<213> ORGANISM: Rattus norvegicus

<400> SEQUENCE: 139
gatccaggct ccagttgtca tggctgcttt gatgagccct ttcccgaaga cttgcttgag    60
tttgggctgg agttcaaagt tctgcagccc tccgtgcaca gagatgagaa gtttgggaag   120
ctcta                                                                125

<210> SEQ ID NO 140
<211> LENGTH: 103

```
<212> TYPE: DNA
<213> ORGANISM: Rattus norvegicus

<400> SEQUENCE: 140
gatccatgga ggtgcactgg ttataggcat ggcttcattg tatgatggct ccatgctggc     60
agccatggag aatgtagtgg tggtcactat ccaataccgc cta                     103

<210> SEQ ID NO 141
<211> LENGTH: 172
<212> TYPE: DNA
<213> ORGANISM: Rattus norvegicus

<400> SEQUENCE: 141
gatccaacca caaacccaca gggtgacaca ctggatgtct ccttcctcta cctggagcct     60
gaggaaaaga aactggtggt cctgcctttc cctgggaagg aacagcgctc ccctgagtgc    120
ccggggcccg aaaagcaaag aaccccctga tgctccccgc tgagactcac ta           172

<210> SEQ ID NO 142
<211> LENGTH: 238
<212> TYPE: DNA
<213> ORGANISM: Rattus norvegicus

<400> SEQUENCE: 142
gatccgtgct ggccacaccc agagcaccaa ggatggggag ctcaggccat atggccaagc     60
atgtgtggat gacagcaaag gtcagaagct actgcctgcc cctctggttt agatggttgc    120
tcaggagccc agacttcgac tcatggtgtg ccagggaggg ctgggacaa caggggtcc     180 cttcccaggc ccatctgctg ccccacactg atctgcctgt cttttctgct gctctcta     238

<210> SEQ ID NO 143
<211> LENGTH: 104
<212> TYPE: DNA
<213> ORGANISM: Rattus norvegicus

<400> SEQUENCE: 143
gatccgtatc tggctgtagc ttcgctcctc agcaaacaga gcgcccatga aagcccaat     60 ggatgtccct ccgattatgt ccacggggat gccacattct gcta                    104

<210> SEQ ID NO 144
<211> LENGTH: 178
<212> TYPE: DNA
<213> ORGANISM: Rattus norvegicus
<220> FEATURE:
<221> NAME/KEY: unsure
<222> LOCATION: (1)..(178)
<223> OTHER INFORMATION: unsure at all n locations

<400> SEQUENCE: 144
gatccgggac agtgcagggc agaagggcac tgggaagtgg acggccatct ccgcgctgga     60
gtacggcatg cctgtcaccc tcatcggaga agctgtcttt gctcggtgct tgtcttctct    120
gaaggaggag cgagttcagg ccagcagana gctgaagggc cccaagatgg tccagcta     178

<210> SEQ ID NO 145
<211> LENGTH: 157
<212> TYPE: DNA
<213> ORGANISM: Rattus norvegicus
<220> FEATURE:
<221> NAME/KEY: unsure
<222> LOCATION: (1)..(157)
<223> OTHER INFORMATION: unsure at all n locations
```

<400> SEQUENCE: 145

```
gatcctaaag cgcaaagtca tagagaaagc gcaacagatt caggttctgc agaaagacgt      60
ccgggatcag ctgatagaca tgaagcgcct gnaggtaagc ctgaggcncn ggccccaatt     120
tgtctttgac taagaaaaaa ggaatangaa cactcta                              157
```

<210> SEQ ID NO 146
<211> LENGTH: 207
<212> TYPE: DNA
<213> ORGANISM: Rattus norvegicus

<400> SEQUENCE: 146

```
gatcctccgg gttatagatc aagagcttca tggggttagg atggcatcct gccaaaatat      60
ctccggtggc tggatcaaca gtcaggttat ccactaaggt gcccagctga attaccttca     120
ctggagttaa atcccaatta ttgtgttttt tcattatgtg aatgttctta gctgttacat     180
cagctacata gacatacttc tggtcta                                         207
```

<210> SEQ ID NO 147
<211> LENGTH: 453
<212> TYPE: DNA
<213> ORGANISM: Rattus norvegicus
<220> FEATURE:
<221> NAME/KEY: unsure
<222> LOCATION: (1)..(453)
<223> OTHER INFORMATION: unsure at all n locations

<400> SEQUENCE: 147

```
gatccttagc ccatgcagca gtgttctttc cgttcgtgtt ttccaggaca gtctggtgct      60
tcacaaaggc tacgtctccc ttctcaacga ggcactggaa agcccctgta taaccattat     120
atccctctct gttgttcgga gcacattttg ctgggccaat acacaggtca cagagggtgg     180
aattcttctt atagccagga gcacagcctt gactgaaaaa ttcatcgaac ttgcagtggt     240
tgatcctgct gaacagcagg cccatagggga tgttccagcc ggcggttctg tctactccag     300
tatggcagga cttcttgcct ttcaggttgt tccagttgat gctggagtct gatgccttca     360
ccacagccac ggcataatac cctttaggaa agacatctga ttgtgggttt gtacacgaag     420
agatatcata gttctctgcc atgacnggca cta                                  453
```

<210> SEQ ID NO 148
<211> LENGTH: 140
<212> TYPE: DNA
<213> ORGANISM: Rattus norvegicus

<400> SEQUENCE: 148

```
gatctatttc ttcatccttt gttctataca atagaatgcc tctctgtcct gaagtcagtc      60
caagaaatgc ttaatgggtt cctgtattct ttcttcctgg attactcagt gctgagtgga     120
gacttctcac caggactcta                                                 140
```

<210> SEQ ID NO 149
<211> LENGTH: 258
<212> TYPE: DNA
<213> ORGANISM: Rattus norvegicus

<400> SEQUENCE: 149

```
gatctacgca accgactcgg gcagtaccgc aacgaggtaa acaccatgct gggccagagc      60
acagaggagc tgcggtcgcg cctctccaca cacctgcgca agatgcgcaa gcgcctgatg     120
cgggatgcgg atgatctgca gaagcgcctg gcggtgtaca aggccggggc acaggagggc     180
```

```
gccgagcgcg gtgtgagtgc tatccgtgag cgcctggggc cactggtgga gcagggtcgt      240
cagcgcacag ccaaccta                                                    258

<210> SEQ ID NO 150
<211> LENGTH: 98
<212> TYPE: DNA
<213> ORGANISM: Rattus norvegicus

<400> SEQUENCE: 150
gatctagaag gcaagagtaa tctcggtgct gacgctccac atcagaacgg tgaatgccac       60
cctaatgaga agggctctgt cagcatggac ctggacta                              98

<210> SEQ ID NO 151
<211> LENGTH: 64
<212> TYPE: DNA
<213> ORGANISM: Rattus norvegicus

<400> SEQUENCE: 151
gatctagatg acacggagga gccccaggac cttccctgag gtgatttcac ccttggtgcc       60
acta                                                                   64

<210> SEQ ID NO 152
<211> LENGTH: 136
<212> TYPE: DNA
<213> ORGANISM: Rattus norvegicus

<400> SEQUENCE: 152
gatctccaca tcagtactac aatggctatg agaaaggcct gcaagctttc tccatggaca       60
aacacctggg ccacggcttc gctccgcagg tagatatttt cgatcttttc tggagctatg      120
tactctcctt gggcta                                                      136

<210> SEQ ID NO 153
<211> LENGTH: 132
<212> TYPE: DNA
<213> ORGANISM: Rattus norvegicus

<400> SEQUENCE: 153
gatctccgga ggtgcggtgc ctctggttgt aagaccagct ttgaagcact cctacagagc       60
catctgagca gagggcctg gcactccagg caggcgagcg atgctcaagc ttgttaccag       120
tctggtctcc ta                                                          132

<210> SEQ ID NO 154
<211> LENGTH: 218
<212> TYPE: DNA
<213> ORGANISM: Rattus norvegicus

<400> SEQUENCE: 154
gatctccacc gaactggtga agagcaagct cagggagacc actggggcag cctgcaaata       60
tggggtaagc aactacatgt gtattcccag tccctgtcta agatagaga cgtcatgttg      120 ccatagctgc tcacgctcct gtgagctgcc ttctccccat cctaagtcct cctcagcttt      180
cctaaacacc tcatccactc ccttcctccc taagccta                              218

<210> SEQ ID NO 155
<211> LENGTH: 124
<212> TYPE: DNA
<213> ORGANISM: Rattus norvegicus
<220> FEATURE:
```

<221> NAME/KEY: unsure
<222> LOCATION: (1)..(124)
<223> OTHER INFORMATION: unsure at all n locations

<400> SEQUENCE: 155

| gatctccatc agaaaccaaa atgatcagag agactgagtc gggggttcagc aatcccatgt | 60 |
| tactggcttc gttcagaatg aaaattgctc tcagcagncc tcattgatat ttgtgcctcc | 120 |
| acta | 124 |

<210> SEQ ID NO 156
<211> LENGTH: 218
<212> TYPE: DNA
<213> ORGANISM: Rattus norvegicus

<400> SEQUENCE: 156

| gatctccccc agcagcagct ccaccacaat cagaagcttg tgcaccgtct gtttgaagcc | 60 |
| aactgctgtg tgctgtggtg cctttcgaag ggcattggtc atcgttctcc gggcttcaga | 120 |
| gtactccagt tggatagcct tgattcgccc tgtgtagtag aggtacctgg cccactcatt | 180 |
| gttgttagcc tgttcgggga acacagactt ggacacta | 218 |

<210> SEQ ID NO 157
<211> LENGTH: 43
<212> TYPE: DNA
<213> ORGANISM: Rattus norvegicus

<400> SEQUENCE: 157

| gatctcattt taacccgtaa ccagtctata tgtgtttgga cta | 43 |

<210> SEQ ID NO 158
<211> LENGTH: 357
<212> TYPE: DNA
<213> ORGANISM: Rattus norvegicus

<400> SEQUENCE: 158

| gatctgaagc aggaagactt ccagctgctg tgccctgatg gtaccaagaa gcctgtaacc | 60 |
| gagttcgcca cctgccacct ggcccaagct ccaaaccatg ttgtggtctc acgaaaagag | 120 |
| aaggcagccc gggttagcac tgtgctgact gcccagaagg atttattttg gaaaggtgac | 180 |
| aaggactgca ctggcaattt ctgtttgttc cggtcttcca ccaaggacct tctgttcaga | 240 |
| gatgacacca gtgtttgac taaacttcca gaaggtacca catatgaaga gtacttagga | 300 |
| gcagagtact tgcaagctgt tggaaacata aggaagtgtt caacctcacg actccta | 357 |

<210> SEQ ID NO 159
<211> LENGTH: 47
<212> TYPE: DNA
<213> ORGANISM: Rattus norvegicus

<400> SEQUENCE: 159

| gatcttggcc ttcacgttct cgatggtgtc actgggctcc acctcta | 47 |

<210> SEQ ID NO 160
<211> LENGTH: 113
<212> TYPE: DNA
<213> ORGANISM: Rattus norvegicus

<400> SEQUENCE: 160

| gatcttatca caccagccag caaagtaccg gaaggtctgg atggacatgc ccacgtgcgt | 60 |
| cttcagggcc agcgtgtaga cggcacctgc atccagggcc tcaatggtgg cta | 113 |

<210> SEQ ID NO 161
<211> LENGTH: 163
<212> TYPE: DNA
<213> ORGANISM: Rattus norvegicus

<400> SEQUENCE: 161

| gatcttggat gatgacaatt ttctgggagc tgagaatgcc tttaacttgt ttgtgtgtca | 60 |
| gaaggacagt gctgccacca ctgatgagga gcggcagcac ctacaggagg ttggtctctt | 120 |
| ccacctgggc gagtttgtca atgtgttctg ccatggctcc cta | 163 |

<210> SEQ ID NO 162
<211> LENGTH: 180
<212> TYPE: DNA
<213> ORGANISM: Rattus norvegicus

<400> SEQUENCE: 162

| gatcttggtg accatgctac cctgaagagg tccccaggag attgcaagag tgccccaact | 60 |
| acagaggaga ctcgcaggct gtctcaggcc atgatggctt ttactactga cctgttctcc | 120 |
| ctggtggccc aaacatccac cagctccaac cttgtcctgt cacccttag tgtggccta | 180 |

<210> SEQ ID NO 163
<211> LENGTH: 179
<212> TYPE: DNA
<213> ORGANISM: Rattus norvegicus

<400> SEQUENCE: 163

| gatcttaact gcagattcta cacatttctc atcctctaat ggcttcctct ggctgccagg | 60 |
| ctgaagaaac ttcttcactg tggggaggtt gctgactctg gttctcaggg ccttcagcag | 120 |
| agggaagttg gccaaagcgc tggggtccag ctcttccaca tggtagagaa cttgaacta | 179 |

<210> SEQ ID NO 164
<211> LENGTH: 217
<212> TYPE: DNA
<213> ORGANISM: Rattus norvegicus

<400> SEQUENCE: 164

| aattcacagc tgaggaatgc taaatggctg agaagcacct aaagaaatgt tcaacatttt | 60 |
| tagtcataag ggaaatgcaa atcaaaacaa ccctgagatt ctacctcaca ccagtcagaa | 120 |
| tggctaagat caaaaactca ggtgacagca aatgctggaa aggatgtgga gaaagaggaa | 180 |
| cactcctcca tttttggtgg gattacagaa tggttta | 217 |

<210> SEQ ID NO 165
<211> LENGTH: 197
<212> TYPE: DNA
<213> ORGANISM: Rattus norvegicus

<400> SEQUENCE: 165

| aattcacaga gacggctgcc atatttgaag atggctccag ggaggatgac attgatgtgg | 60 |
| tcatctttgc cacaggctac agctttgcct ttccttttct tgaggactct gtcaaagtag | 120 |
| tccaaaacaa ggtctccttg tataaaaagg tctttccccc taacctggaa aaaccaactc | 180 |
| ttgcaatcat cggttta | 197 |

<210> SEQ ID NO 166
<211> LENGTH: 419
<212> TYPE: DNA

<213> ORGANISM: Rattus norvegicus

<400> SEQUENCE: 166

| | | | | | |
|---|---|---|---|---|---|
| aattcagttt | acatcttggt | cacagcccat | ctctctcctc | ttccttagtc | ccatccttgc | 60 |
| cagatccctg | tcccaattgc | ccctccact | tgggtaccac | ctaaccctgg | gacatctgct | 120 |
| tcatgtagta | ctagctatat | cctttctcac | tgaggcctaa | ccaggcagtc | ttggtaagga | 180 |
| tgagatccaa | tgctaggaac | tatagactga | gacaaccca | gttctgttgg | gagcagctaa | 240 |
| agatggcacg | acatccagtg | gtcttttgtg | gtatacaacc | ataacatggg | tatatagcca | 300 |
| tgtccctggc | cttcttctgg | catttacaag | gccagggtga | taagcatgtc | aataaggtat | 360 |
| ctcacacccc | accaatcctc | agaaggacaa | gtttacagcc | actgcctgtt | ttgtactta | 419 |

<210> SEQ ID NO 167
<211> LENGTH: 159
<212> TYPE: DNA
<213> ORGANISM: Rattus norvegicus

<400> SEQUENCE: 167

| | | | | | |
|---|---|---|---|---|---|
| aattcagtct | tatcaatgaa | ggtcagagcc | attgggaaag | gtgaagtggg | ggagccctgt | 60 |
| catcgatccc | aactgggtcg | gaaccctccc | acgcatgact | caattcagag | ctgtttccca | 120 |
| ggaggctggg | gcgggatgca | gacagattcc | aacaccta | | | 159 |

<210> SEQ ID NO 168
<211> LENGTH: 110
<212> TYPE: DNA
<213> ORGANISM: Rattus norvegicus

<400> SEQUENCE: 168

| | | | | | |
|---|---|---|---|---|---|
| aattcagcag | aactccttga | gggaaaatca | tgatccagtt | atgatttcat | cccgtggcac | 60 |
| aacctttaga | ataatgggtt | ttgttggttg | aagaagtcct | tgtctgctta | | 110 |

<210> SEQ ID NO 169
<211> LENGTH: 199
<212> TYPE: DNA
<213> ORGANISM: Rattus norvegicus

<400> SEQUENCE: 169

| | | | | | |
|---|---|---|---|---|---|
| aattcatcgt | aaatggactc | ctcaacaaaa | agtctggatg | ctgcgacaca | aatctgaccc | 60 |
| tggtggaaga | atactccttg | gtgtgcaaac | tcatcagcac | tatccaagtc | agcatctgca | 120 |
| aacacaatgc | aagggctctt | tccccaagc | tccagggtga | ccctcttcag | attgcttttc | 180 |
| cctgcagctt | ctttgatta | | | | | 199 |

<210> SEQ ID NO 170
<211> LENGTH: 380
<212> TYPE: DNA
<213> ORGANISM: Rattus norvegicus
<220> FEATURE:
<221> NAME/KEY: unsure
<222> LOCATION: (1)..(380)
<223> OTHER INFORMATION: unsure at all n locations

<400> SEQUENCE: 170

| | | | | | |
|---|---|---|---|---|---|
| aattcctagg | gaagtcggaa | ccagagcgcc | agcactgagc | ctggcccgtg | aaggagcatg | 60 |
| gagacccacc | ttccttccct | tctccctgaa | cagcagtctg | gcacccagaa | gctcagagtg | 120 |
| ccaccacctg | tggtgctcag | gagcccagcc | tagaaagagg | actccgacac | agcgggcagn | 180 |
| ggctccacag | acggatctat | gaggaaaata | cgggggcagg | cangcaggca | ggcgacccc | 240 |

| | |
|---|---:|
| tgaccctctg gtggccgctg tatctgagcc cttttgggaa ggcttataga caacaggtgg | 300 |
| agcccatacg ctgggcatag ggagcctggg aagggctcag gagctcagga ccactccagg | 360 |
| ctctctagca ccaccgctta | 380 |

<210> SEQ ID NO 171
<211> LENGTH: 366
<212> TYPE: DNA
<213> ORGANISM: Rattus norvegicus

<400> SEQUENCE: 171

| | |
|---|---:|
| aattccctgg cttggcagac gtcaccatcg cagaagtgga ctgcaccgct gagcgtggtg | 60 |
| tttgcagcaa gtactcggta cgaggctacc ccacattgct gcttttccgg gggaggtgag | 120 |
| aaagtgggtg agcacaatgg aggcagagac ctcgactctc tacacagctt tgttctgcgc | 180 |
| caggcaaagg atgaactcta agaacctgg tgaagccgtc atccaccctg gccttatgca | 240 |
| ccccgtgcat aggagtgacc tcacatggac atgcgtatct tcactgtggt tagtcagaac | 300 |
| gctgaatgta ttgagcttgt gttgcttgct gtgtgccctt tgagccacca cacactacgg | 360 |
| acctta | 366 |

<210> SEQ ID NO 172
<211> LENGTH: 339
<212> TYPE: DNA
<213> ORGANISM: Rattus norvegicus

<400> SEQUENCE: 172

| | |
|---|---:|
| aattccatca gtaaagctaa agcagctacg tctggtccgg tctcttcttg atctgtttct | 60 |
| agatatggaa gcagctacag ggcaggaggt cgagctatgt ttagaatgca tcgaatgggc | 120 |
| caaatcagag aaaagaacct tcttacgcca agcattggag gcaaggctgg tgtctttgta | 180 |
| ttttgatacc aagaggtccc aggaagcatt acatttgggt tctcagctgc ttcgggagtt | 240 |
| gaaaaagatg gatgataaag ctcttttggt gaagtacagc ttttagaaag caaaacttac | 300 |
| catgctctga gtaatctgcc gaaagcccga gctgcctta | 339 |

<210> SEQ ID NO 173
<211> LENGTH: 290
<212> TYPE: DNA
<213> ORGANISM: Rattus norvegicus

<400> SEQUENCE: 173

| | |
|---|---:|
| aattccaaga gttcgaggtg gtggcaccca ccgttctggc cagggtgcct ttggaaacat | 60 |
| gtgtcgtgga ggccgcatgt ttgcaccaac caaaacctgg cgtcgttggc atcgcagagt | 120 |
| gaacacaact cagaaacgat atgccatctg ttctgccctg gctgcctcgg ccttaccagc | 180 |
| tttggtgatg tctaaaggtc atcgtgttga ggaagttcct gaactgcctt tggtggttga | 240 |
| agataaagtt gaaagttata agaagaccaa ggaggctgtt cagctgctta | 290 |

<210> SEQ ID NO 174
<211> LENGTH: 199
<212> TYPE: DNA
<213> ORGANISM: Rattus norvegicus

<400> SEQUENCE: 174

| | |
|---|---:|
| aattcctaac actcaggctc tgcccgtggg cttggctgca ggacagcgac ttgactccat | 60 |
| gacttgactc caccccagct tccaccttgg ccgggactgc tctaccctgt gagccaaaca | 120 |

```
ctttaggtgt aagtaggtac actttgtgat gtcactgacc tagtgtaccc tttctttttt    180
catatctata ctgacctta                                                  199

<210> SEQ ID NO 175
<211> LENGTH: 165
<212> TYPE: DNA
<213> ORGANISM: Rattus norvegicus

<400> SEQUENCE: 175
aattcccagc aacagataca atgaggggct gcgctgagct cttcctgcca gaagcagacc    60
atcttctcac ggcatccctc atctcacaag tgtccaggac catggggaca ttgcattcaa    120
agcaccgtac ctgctttcta attgatggtc aaggttatat gctta                   165

<210> SEQ ID NO 176
<211> LENGTH: 46
<212> TYPE: DNA
<213> ORGANISM: Rattus norvegicus

<400> SEQUENCE: 176
aattccagca ataagaaatg aacaaagatt ggagctgaag acctta                   46

<210> SEQ ID NO 177
<211> LENGTH: 39
<212> TYPE: DNA
<213> ORGANISM: Rattus norvegicus

<400> SEQUENCE: 177
aattccgaat gtggattgtg attttcctgc ttccactta                           39

<210> SEQ ID NO 178
<211> LENGTH: 283
<212> TYPE: DNA
<213> ORGANISM: Rattus norvegicus

<400> SEQUENCE: 178
aattccaccc aaggctgctg ggtctgactg gttctacaga acaagtggcc catgctagtc    60
gcaactaccg tgtatactac agcgctggtc ccaaggacga ggaccaggac tatattgtgg    120
accattccat tgccatctac ttgctcaacc cagatggtct cttcactgat tactatggtc    180
gtagcaggtc agcagagcag atcgtagaga gtgtactgcc ggcacatagc tgccttccat    240
agcatactgc cctgaactgt gtactgccta ggccctgtca tta                     283

<210> SEQ ID NO 179
<211> LENGTH: 223
<212> TYPE: DNA
<213> ORGANISM: Rattus norvegicus
<220> FEATURE:
<221> NAME/KEY: unsure
<222> LOCATION: (1)..(223)
<223> OTHER INFORMATION: unsure at all n locations

<400> SEQUENCE: 179
aattccacag aaggttgtat ggagatttga tggtaagaaa ccagatacct taggatctaa    60
cactcggctg tacaagtgga tcccccagaa tgacnttctt ggtcatccna aaaccnaaa    120 gcttttgtag ctcatggtgg aacaaatggc atctatgagg caatctacca tggcattcct   180
attgttggta ttcccttgtt tgcagatcaa ccggataaca tta                     223

<210> SEQ ID NO 180
<211> LENGTH: 182
```

-continued

<212> TYPE: DNA
<213> ORGANISM: Rattus norvegicus

<400> SEQUENCE: 180

```
aattccctgg ctttctgggt ctagagtgtt ctgtgcctcc aaggactgtc tagcgatgac      60
ttgtattggc caccaactgt agatgtatat acggtgtcct tctgatgcta agactccaga     120
cctttcttgg ttttgcttgc tttttctgat tttataccaa ctgtgtggac taagatgcat     180
ta                                                                    182
```

<210> SEQ ID NO 181
<211> LENGTH: 189
<212> TYPE: DNA
<213> ORGANISM: Rattus norvegicus

<400> SEQUENCE: 181

```
aattcctcat tggtcatgtc accgaaggcg ttcatctcca tggtaaagcc gtgcttcccg      60
ttgctgtact ccccattgtg tagctggatc atcctcatgt tcttctccca cactgctctc     120
ctccactctt cctcattcgt gccatacagt cttctgtgtg tggacttcca ctggtgccac     180
tgtgcatta                                                             189
```

<210> SEQ ID NO 182
<211> LENGTH: 160
<212> TYPE: DNA
<213> ORGANISM: Rattus norvegicus

<400> SEQUENCE: 182

```
aattcggggt cctctgaaag ctacccaggg ttctcatctt ccctagagct tgtagtgtaa      60
agtgacagct agtgtgtgcg cgcgctctct cgctctctct ccttctccct ctctctctcc     120
ctattccctc ccctcctctc ctctgcccct cctggttta                            160
```

<210> SEQ ID NO 183
<211> LENGTH: 287
<212> TYPE: DNA
<213> ORGANISM: Rattus norvegicus
<220> FEATURE:
<221> NAME/KEY: unsure
<222> LOCATION: (1)..(287)
<223> OTHER INFORMATION: unsure at all n locations

<400> SEQUENCE: 183

```
aattcggggt gaagnagaag ccgatataca tcaatgtcgt cagggaccga ttgagaggct      60
agtttcctac tattactttc tgaggtttgg agatgattac agnccggac taaggaggcg     120
gacacaagga gacaagaaga ccttcgatga atgcgtggct gaggcggctc agactgtgct     180
ccagagaagc tctggcttca gatcccgttc ttctgtggcc actagctcag aatgctggaa     240
tgttggaagc agatgggcga tggatcaagc taagtacanc ctggtta                   287
```

<210> SEQ ID NO 184
<211> LENGTH: 135
<212> TYPE: DNA
<213> ORGANISM: Rattus norvegicus

<400> SEQUENCE: 184

```
aattcgtcaa agcagcacca ggcccccgac tgtgccaaac cactgaagaa gcgccccatc      60
atctgaaagg caagcaaagc tgatcaactt caggctgcct tgttggtcat ctctaacatt     120
cataatctag agtta                                                      135
```

<210> SEQ ID NO 185
<211> LENGTH: 79
<212> TYPE: DNA
<213> ORGANISM: Rattus norvegicus

<400> SEQUENCE: 185

```
aattcgacag tgtcccatgc agacattact aattgattct gttcttatta tggaaccttt    60
tggctggcca ggtgtgtta                                                 79
```

<210> SEQ ID NO 186
<211> LENGTH: 413
<212> TYPE: DNA
<213> ORGANISM: Rattus norvegicus

<400> SEQUENCE: 186

```
aattcgtagg aagcttcaaa accaaacaag acttcataga tttgattgaa gtcatctacc    60
ggggagctat gcgaggaaaa cttattgttc aaagtcctat tgaccccaag aacataccca   120
aatacgacct cctctatcaa gacatttagc actcgctgct gttggagaga agagaggcac   180
aggctgaagc agaacctgaa ctcagagagc ctgtggtctg gagtccctca gagacatgct   240
cactgcctga gcaaagaggt ttcataggtc tgtaatcaac ggcccctctg cagaagcccc   300
agtgctccca gaatggagat gcctgagcgc ccattctctg agagcctcag agcagtgagc   360
gagtgacagg tggcattgta acggacccctt tatcttgact gtctttcccc tta         413
```

<210> SEQ ID NO 187
<211> LENGTH: 362
<212> TYPE: DNA
<213> ORGANISM: Rattus norvegicus
<220> FEATURE:
<221> NAME/KEY: unsure
<222> LOCATION: (1)..(362)
<223> OTHER INFORMATION: unsure at all n locations

<400> SEQUENCE: 187

```
aattcgggca gggcatcatg gtccataaac atgaggggat gaaggtcttt gtgcccactg    60
gcttttcagc cttcccttcc gagctactgc atgccccaga aaagtgggtg aaggtcaagt   120
ccccaaactc atctcctatt cctacatgga acgtggggc cnctttgctg cctttgaaga   180
gcccaagctt ctggcccagg acatccgcaa gttcgggtcc ctggctgagc tgcagtagtg   240
acactggata ccaactgtgg ctttagcagc agccctggtt cctcccaagt cacacttatg   300
gaagatgacc cctttctnag gaataagttt gttccctgac cacactcgag gacccagact   360
ta                                                                  362
```

<210> SEQ ID NO 188
<211> LENGTH: 74
<212> TYPE: DNA
<213> ORGANISM: Rattus norvegicus

<400> SEQUENCE: 188

```
aattcggggc tgtttcagat ttcctacact ctgattggta ggtgtgtcca tctggacagt    60
ttattctagc ctta                                                     74
```

<210> SEQ ID NO 189
<211> LENGTH: 267
<212> TYPE: DNA
<213> ORGANISM: Rattus norvegicus
<220> FEATURE:
<221> NAME/KEY: unsure

```
<222> LOCATION: (1)..(267)
<223> OTHER INFORMATION: unsure at all n locations

<400> SEQUENCE: 189
aattcggggg gccgttgggc ttcacggcga tgctgatcct gctgcctgcc accatgttcc    60
acctgcttct ggcggcccgc tcgggtccgg cgcgcctcct ggccctacca gcctatctgc   120
ctgggctgga ggagctgtgg agcccacggg ctctgctgct gttgttcatc tggctcggcc   180
tgcaggtggc gctctatttg ctgcctgcac gcaaggtggc cgagggctg ganctgaagg    240 acaagagtcg cctgcgctac cctatta                                      267

<210> SEQ ID NO 190
<211> LENGTH: 192
<212> TYPE: DNA
<213> ORGANISM: Rattus norvegicus

<400> SEQUENCE: 190
aattctaaac atatgccatt gtggaagaag caaagccacg gagatagcag gccagtgcag    60
attcactgat gtgacaactg cattctctca ggttaggaca ttggtggaag gagcctctgc   120
acttatgggc tgtgtagcta tgggaacctt gtacttcctg ccaattttgc tctgaaactc   180
aaactgcctt ta                                                      192

<210> SEQ ID NO 191
<211> LENGTH: 83
<212> TYPE: DNA
<213> ORGANISM: Rattus norvegicus

<400> SEQUENCE: 191
aattctagat ttcttggtaa actatcaaat ctgtatatgt atgtaataaa gtgtctaatg    60
ctaggagttt attggaaggt tta                                           83

<210> SEQ ID NO 192
<211> LENGTH: 56
<212> TYPE: DNA
<213> ORGANISM: Rattus norvegicus

<400> SEQUENCE: 192
aattctcaga aactatataa tacattctgc tgttggccaa tgcaaagtgt acttta        56

<210> SEQ ID NO 193
<211> LENGTH: 42
<212> TYPE: DNA
<213> ORGANISM: Rattus norvegicus

<400> SEQUENCE: 193
aattcttcag aaatgtggtg tctaagaaca ccagaccctt ta                      42

<210> SEQ ID NO 194
<211> LENGTH: 133
<212> TYPE: DNA
<213> ORGANISM: Rattus norvegicus

<400> SEQUENCE: 194
aattctatgc attgatttac atgtactgaa ccatacttct ttgactgtaa tggagccaac    60
ttgtggtaaa tggttatttt catatgttct tgacttgata tgaaatattt tactataaac   120
ttttcatatg tta                                                     133

<210> SEQ ID NO 195
```

```
<211> LENGTH: 79
<212> TYPE: DNA
<213> ORGANISM: Rattus norvegicus

<400> SEQUENCE: 195
aattctgacc acatgagctt cctagacaga gtgaagaata tgctttatcc tgtgccatgg      60
atgtatttat gccatgtta                                                  79

<210> SEQ ID NO 196
<211> LENGTH: 65
<212> TYPE: DNA
<213> ORGANISM: Rattus norvegicus

<400> SEQUENCE: 196
aattctcctt gtagtagcgt tgggaggaga caatggttcc tgtcgtccag tagatcatga      60
tgtta                                                                 65

<210> SEQ ID NO 197
<211> LENGTH: 64
<212> TYPE: DNA
<213> ORGANISM: Rattus norvegicus

<400> SEQUENCE: 197
aattcttcag aaggtatgtg aagctatttg catatgtaaa taaactgcta agattgtcat      60
gtta                                                                  64

<210> SEQ ID NO 198
<211> LENGTH: 41
<212> TYPE: DNA
<213> ORGANISM: Rattus norvegicus
<220> FEATURE:
<221> NAME/KEY: unsure
<222> LOCATION: (1)..(41)
<223> OTHER INFORMATION: unsure at all n locations

<400> SEQUENCE: 198
aattctgcga nnaagttcaa atacaatagt gctggcagtt a                         41

<210> SEQ ID NO 199
<211> LENGTH: 36
<212> TYPE: DNA
<213> ORGANISM: Rattus norvegicus

<400> SEQUENCE: 199
aattctgcaa attgccttac agactagcca tactta                               36

<210> SEQ ID NO 200
<211> LENGTH: 218
<212> TYPE: DNA
<213> ORGANISM: Rattus norvegicus

<400> SEQUENCE: 200
aattctctac catctgttac aggctgtggg atgtcagagg aaggaacggg gtttggtggt      60
ggtacccagg gcaggaccga gcagcaggat tcccgcaaga gaaggaggc agatgggcct     120 ttcaagagct ttaggaagcg actaacagca gagtgtctgg gaacatacga atcagtctct    180
tgcatattgt aataaaccaa acacaagact cgccatta                            218

<210> SEQ ID NO 201
<211> LENGTH: 151
<212> TYPE: DNA
<213> ORGANISM: Rattus norvegicus
```

```
<220> FEATURE:
<221> NAME/KEY: unsure
<222> LOCATION: (1)..(151)
<223> OTHER INFORMATION: unsure at all n locations

<400> SEQUENCE: 201
aattcagcct gaggaggaaa tcagtctatg gtntacttcg tcctgcctct tagcttctgt      60
acctgcttgt cacatttgca cctatgagtc aagacatgtt tgttaccttt attttgattt    120
atttctatta caattcaatt tttttccttt a                                   151

<210> SEQ ID NO 202
<211> LENGTH: 63
<212> TYPE: DNA
<213> ORGANISM: Rattus norvegicus

<400> SEQUENCE: 202
aattcagtca cggactttat gcctttgaaa gttgtcacca ttttattgtc accctccatc     60
tta                                                                  63

<210> SEQ ID NO 203
<211> LENGTH: 221
<212> TYPE: DNA
<213> ORGANISM: Rattus norvegicus
<220> FEATURE:
<221> NAME/KEY: unsure
<222> LOCATION: (1)..(221)
<223> OTHER INFORMATION: unsure at all n locations

<400> SEQUENCE: 203
aattcctctt atcaactgca tacaaagtgt nttcaataca attttttccg tataaaata      60 ctgggaaaaa ttgataaata acaggtaaga gaaagatatt tctaggcaat taggattgtt   120
gggacagtga gtcctgtggg gtgtttggac acagccacag gacaggcctc ctgacagtgc   180
tgcagatcag acggcaaaag aaagcagaac tgtctggttt a                      221

<210> SEQ ID NO 204
<211> LENGTH: 178
<212> TYPE: DNA
<213> ORGANISM: Rattus norvegicus

<400> SEQUENCE: 204
aattcctcca tcattgcaga ccggattgca ctcaagctgg ttggccctga gggctttgta    60
gtgacagaag caggattcgg agcagacata ggaatggaaa agttcttcaa catcaagtgc   120
cggtattctg gtctccagcc tcatgtggtg gttcttgttg ccactgtcag ggctctta     178

<210> SEQ ID NO 205
<211> LENGTH: 233
<212> TYPE: DNA
<213> ORGANISM: Rattus norvegicus

<400> SEQUENCE: 205
aattccagaa gaaaaggca ggatcacagt cctagtgggg aagctgcttc ctggtccacc      60
cgaagacacc aagttcaacc accgtccatc cagaaatgag aagaacaata ccctagagca   120
aagtcatcca cacccagtac acactccgct gctaacctga aatgcatgaa cagaaaccca   180
tagtatttat gcccctctag gcaggtgtcc acaataaaat tgtgagcagc tta          233

<210> SEQ ID NO 206
<211> LENGTH: 74
<212> TYPE: DNA
```

```
<213> ORGANISM: Rattus norvegicus
<220> FEATURE:
<221> NAME/KEY: unsure
<222> LOCATION: (1)..(74)
<223> OTHER INFORMATION: unsure at all n locations

<400> SEQUENCE: 206
aattcggaag gaactctcca acnnctcgtt cagggagata tagccgcttt ctatctaaaa      60
gactcattac ttta                                                        74

<210> SEQ ID NO 207
<211> LENGTH: 54
<212> TYPE: DNA
<213> ORGANISM: Rattus norvegicus

<400> SEQUENCE: 207
aattctccag ataatggtca ttaagacaat tctttccagc atgctcaagg gtta            54

<210> SEQ ID NO 208
<211> LENGTH: 240
<212> TYPE: DNA
<213> ORGANISM: Rattus norvegicus
<220> FEATURE:
<221> NAME/KEY: unsure
<222> LOCATION: (1)..(240)
<223> OTHER INFORMATION: unsure at all n locations

<400> SEQUENCE: 208
aattcacggg aaatgncttg tgcttagcat ggagaagaag gaagtggaag ggaatgggga      60
tcaaactctt ctaacattgc aatatgctaa tattgttaga ctgctacaga tgcactgaaa     120
cacagaatat gatcttttaa ggggccaaaa atgctacggt gtgaaaatat cacaatgact     180
gtctttncct taaaaagtc acataaaatg cagtttagaa caaggngaaa cataggtcta      240

<210> SEQ ID NO 209
<211> LENGTH: 147
<212> TYPE: DNA
<213> ORGANISM: Rattus norvegicus
<220> FEATURE:
<221> NAME/KEY: unsure
<222> LOCATION: (1)..(147)
<223> OTHER INFORMATION: unsure at all n locations

<400> SEQUENCE: 209
aattcagggt atgnnnngtg gntataaagt acatttctgt agtgtgtgtg ctaccttagt      60
ttnatgttct ttatgaaaaa ttaaaaacct ccccctccac aactttcctc ttgctttgaa     120
tataggtaag atcataacat ctatcta                                         147

<210> SEQ ID NO 210
<211> LENGTH: 67
<212> TYPE: DNA
<213> ORGANISM: Rattus norvegicus
<220> FEATURE:
<221> NAME/KEY: unsure
<222> LOCATION: (1)..(67)
<223> OTHER INFORMATION: unsure at all n locations

<400> SEQUENCE: 210
aattcatgga aaacnnntat gttatttta atacataatg ttcaaaataa nnatatgttc      60
tactcta                                                               67

<210> SEQ ID NO 211
<211> LENGTH: 41
```

```
<212> TYPE: DNA
<213> ORGANISM: Rattus norvegicus

<400> SEQUENCE: 211
aattcattct gttttttttaa tctaactttt atatcaatct a                 41

<210> SEQ ID NO 212
<211> LENGTH: 99
<212> TYPE: DNA
<213> ORGANISM: Rattus norvegicus
<220> FEATURE:
<221> NAME/KEY: unsure
<222> LOCATION: (1)..(99)
<223> OTHER INFORMATION: unsure at all n locations

<400> SEQUENCE: 212
aattcatctc ctccngaaag caaagttatg actattcttt ttcacagatc aaattacaag    60
gggactaata gtgatgtaat ggnacccatg ccctgccta                          99

<210> SEQ ID NO 213
<211> LENGTH: 141
<212> TYPE: DNA
<213> ORGANISM: Rattus norvegicus
<220> FEATURE:
<221> NAME/KEY: unsure
<222> LOCATION: (1)..(141)
<223> OTHER INFORMATION: unsure at all n locations

<400> SEQUENCE: 213
aattccatgt ctatggnttc caagtcngna gagaancacn nggatgactg ccaggaggac    60
ccaggtttcc agtgtgagag ctgaaancag gtccatccct gcttgtctgt cancaaatta   120
ctcctcggtg ttctccctct a                                            141

<210> SEQ ID NO 214
<211> LENGTH: 134
<212> TYPE: DNA
<213> ORGANISM: Rattus norvegicus

<400> SEQUENCE: 214
aattcctcca ccatttaatt cagctccaat caatttcaa tattgtctac actgttccct     60
gcaaacccat acccattaag atttatgact attcctccta ccctgtttcg cttgctgtgc   120
cacgtgctaa tcta                                                    134

<210> SEQ ID NO 215
<211> LENGTH: 121
<212> TYPE: DNA
<213> ORGANISM: Rattus norvegicus
<220> FEATURE:
<221> NAME/KEY: unsure
<222> LOCATION: (1)..(121)
<223> OTHER INFORMATION: unsure at all n locations

<400> SEQUENCE: 215
aattccccga cccagagata tttgaccctg gccactttt agatgggaat ggaaagttta     60
agaaaagtga ctatttcatg cctttctcag caggaaaacg gatgtnncag ganagggtct   120
a                                                                  121

<210> SEQ ID NO 216
<211> LENGTH: 254
<212> TYPE: DNA
<213> ORGANISM: Rattus norvegicus
<220> FEATURE:
```

```
<221> NAME/KEY: unsure
<222> LOCATION: (1)..(254)
<223> OTHER INFORMATION: unsure at all n locations

<400> SEQUENCE: 216
aattccgtaa agaaataata ttctccttca aaaagaggct ggcccgattc caccgaagga      60
aagagatgga aaaaaacaaa caaaccatcc tgaagtcagc ttctccatgt actgtcacaa    120
tgagagactc aattgcctcg tgagtgtggt ggagggagga aaaagggttc atacctgcct   180
cattaggaag agcagaacta tggttaagan cacagtggac tggatgttac actcantnnn    240
ccacttaata gcta                                                      254

<210> SEQ ID NO 217
<211> LENGTH: 107
<212> TYPE: DNA
<213> ORGANISM: Rattus norvegicus
<220> FEATURE:
<221> NAME/KEY: unsure
<222> LOCATION: (1)..(107)
<223> OTHER INFORMATION: unsure at all n locations

<400> SEQUENCE: 217
aattccgnnc cgaacaaggc cacangtgan ncttactgga ntccatgctg ccatttttt     60 gtctgaaaat gtcagtactt aaaagtattt aggnaacact cgagcta                 107

<210> SEQ ID NO 218
<211> LENGTH: 37
<212> TYPE: DNA
<213> ORGANISM: Rattus norvegicus

<400> SEQUENCE: 218
aattccttgg tattcggtat cagtaggaat ggggcta                              37

<210> SEQ ID NO 219
<211> LENGTH: 291
<212> TYPE: DNA
<213> ORGANISM: Rattus norvegicus
<220> FEATURE:
<221> NAME/KEY: unsure
<222> LOCATION: (1)..(291)
<223> OTHER INFORMATION: unsure at all n locations

<400> SEQUENCE: 219
aattcctgac cantgnnggt ctgganaaga ncccagagga gatccaacgc ctgtnccagg     60
anaagaaggt ggacntgtcc aagcccttgg taagccacat gcggctccgg tgtcacagcc   120
tgccacgtgg tcctggggggc cttcctctgt ggcaaacccg atgtgcctgt ctacgatggc   180
tcctgggtgg agtggtacat gcgtgcccaa ccggagcacg tcatntntca gggccggggg   240
aagaccctgt gaangacaca gtgcagcttg ggtgacaccg gaaccatcct a             291

<210> SEQ ID NO 220
<211> LENGTH: 289
<212> TYPE: DNA
<213> ORGANISM: Rattus norvegicus
<220> FEATURE:
<221> NAME/KEY: unsure
<222> LOCATION: (1)..(289)
<223> OTHER INFORMATION: unsure at all n locations

<400> SEQUENCE: 220
aattcctgga aaaagacata tcagaggaan ttcttaataa aatcatctac cacacctcct     60
ttgatgtaat gaaggaaaac ccaatggcca actataccac tctaccctcc agtatcatgg   120
```

-continued

| | |
|---|---|
| accactctat atctcctttc atgaggaaag ggatgcctgg agactggaan aactacttta | 180 |
| ctgtggcaca aagtgaggat tttgatgaag actaccggag gaagatggca gggagcaata | 240 |
| ttaccttccg cacagagatc tgagagcagt gaggnagagg ganncccta | 289 |

<210> SEQ ID NO 221
<211> LENGTH: 91
<212> TYPE: DNA
<213> ORGANISM: Rattus norvegicus
<220> FEATURE:
<221> NAME/KEY: unsure
<222> LOCATION: (1)..(91)
<223> OTHER INFORMATION: unsure at all n locations

<400> SEQUENCE: 221

| | |
|---|---|
| aattccaggc cagctnntca antaagatcc tatcttaaag tanaatgaaa tagggttggg | 60 |
| gatttagcta cantgnnana gcacttgcct a | 91 |

<210> SEQ ID NO 222
<211> LENGTH: 166
<212> TYPE: DNA
<213> ORGANISM: Rattus norvegicus
<220> FEATURE:
<221> NAME/KEY: unsure
<222> LOCATION: (1)..(166)
<223> OTHER INFORMATION: unsure at all n locations

<400> SEQUENCE: 222

| | |
|---|---|
| aattcccaaa acctnnnacg aagtctccgg antgagtcaa ctataccgct ttcttggcat | 60 |
| gagtccagag gcctccgact ccacagagan cagctcagtn ttcgtcttta ctgcgctaca | 120 |
| cgtagaagag ctaagaaatg gagccggttn ncagaccccn ggacta | 166 |

<210> SEQ ID NO 223
<211> LENGTH: 112
<212> TYPE: DNA
<213> ORGANISM: Rattus norvegicus
<220> FEATURE:
<221> NAME/KEY: unsure
<222> LOCATION: (1)..(112)
<223> OTHER INFORMATION: unsure at all n locations

<400> SEQUENCE: 223

| | |
|---|---|
| aattccagan tcagcaccaa nngacagacc attctaaaat gggcaaagga ctgaacggat | 60 |
| gntccggatt gacagtgacc acacagccca tganganccc acaggaccac ta | 112 |

<210> SEQ ID NO 224
<211> LENGTH: 65
<212> TYPE: DNA
<213> ORGANISM: Rattus norvegicus
<220> FEATURE:
<221> NAME/KEY: unsure
<222> LOCATION: (1)..(65)
<223> OTHER INFORMATION: unsure at all n locations

<400> SEQUENCE: 224

| | |
|---|---|
| aattcgtaaa gaggannctc acnntgaaaa cataaactgc cacagtaagn ncacaaacct | 60 |
| gtcta | 65 |

<210> SEQ ID NO 225
<211> LENGTH: 44
<212> TYPE: DNA
<213> ORGANISM: Rattus norvegicus
<220> FEATURE:

```
<221> NAME/KEY: unsure
<222> LOCATION: (1)..(44)
<223> OTHER INFORMATION: unsure at all n locations

<400> SEQUENCE: 225
aattcgccaa gagcgtttga ntgacagctc tttgtgtatg tcta                    44

<210> SEQ ID NO 226
<211> LENGTH: 105
<212> TYPE: DNA
<213> ORGANISM: Rattus norvegicus
<220> FEATURE:
<221> NAME/KEY: unsure
<222> LOCATION: (1)..(105)
<223> OTHER INFORMATION: unsure at all n locations

<400> SEQUENCE: 226
aattcgatgt gggnnccata naaagtangg aaaaatatgg ggttgtntga tggtcaaatg    60
cctctgtttg ccatcacnga cacagaaatg ancaagaatg tgcta                  105

<210> SEQ ID NO 227
<211> LENGTH: 110
<212> TYPE: DNA
<213> ORGANISM: Rattus norvegicus
<220> FEATURE:
<221> NAME/KEY: unsure
<222> LOCATION: (1)..(110)
<223> OTHER INFORMATION: unsure at all n locations

<400> SEQUENCE: 227
aattcgagac ccaanncacn aaccnaaacc cacaaccaca acagtaacna gaacaagaag    60
aaagaaagca aagggttgg gatttagntc agtggnagag cgcttgccta              110

<210> SEQ ID NO 228
<211> LENGTH: 392
<212> TYPE: DNA
<213> ORGANISM: Rattus norvegicus
<220> FEATURE:
<221> NAME/KEY: unsure
<222> LOCATION: (1)..(392)
<223> OTHER INFORMATION: unsure at all n locations

<400> SEQUENCE: 228
aattcgggag tgnggnncct tctgantctt gcancaaaga ggctnttcta tagcatgnnc    60
nangatgctg gcttggtgtg aacnnatctc tggcatatct gatgangatg cangnccagg   120
atcccantgt ccangnatga nccagcaacc ctggaaacct acactcccca gagaaaaacc   180
anaaattgaa agaanancaa actaaaagga ngcnaaacac ataaagcatc antcacagtt   240
tgnnccagcc tngatctgac ntcgaanaag cctgaagaca gatgtgcccc ncttcanaca   300
cgtctggctt ctggcaccac ttgtgagctn cctgaaagtc accannctcn tgctgtntcc   360
caanncaang nnatgagnnc ccnaacacac ta                                392

<210> SEQ ID NO 229
<211> LENGTH: 81
<212> TYPE: DNA
<213> ORGANISM: Rattus norvegicus

<400> SEQUENCE: 229
aattcggaag gactctccaa tgtcgttcag ggagatatag ccgctttcta tctaagaaca    60
tcattacttt aacaagtact a                                             81
```

<210> SEQ ID NO 230
<211> LENGTH: 203
<212> TYPE: DNA
<213> ORGANISM: Rattus norvegicus
<220> FEATURE:
<221> NAME/KEY: unsure
<222> LOCATION: (1)..(203)
<223> OTHER INFORMATION: unsure at all n locations

<400> SEQUENCE: 230
aattctggac caagactctg ccccagaaga tccaagagct aaagggttct caggacaatc     60
acacagagct ataatgtcct gtgtcaagaa aactgtgtag acttgangta cagggtttct    120
gaagcctcta aagtctacac ttgaatggat atatcacatc tgttggatga ccctgcaatt    180
aaggttgaag tcgaccatgt cta                                            203

<210> SEQ ID NO 231
<211> LENGTH: 110
<212> TYPE: DNA
<213> ORGANISM: Rattus norvegicus

<400> SEQUENCE: 231
aattctgctc tgtgtatcct gatccaccaa gcagtcactt ggtagcagaa aagtggtctt     60
atgtctgctc ttaactgtgg tggcgcttct gggactgtct ccagctcta               110

<210> SEQ ID NO 232
<211> LENGTH: 252
<212> TYPE: DNA
<213> ORGANISM: Rattus norvegicus
<220> FEATURE:
<221> NAME/KEY: unsure
<222> LOCATION: (1)..(252)
<223> OTHER INFORMATION: unsure at all n locations

<400> SEQUENCE: 232
aattctggaa taaganncct gttttttaaaa aaggaactgc cgcaatctga aagacttcca    60
aagaangtta gagcacagta catactaccc ctgccctgct cccaccaccc gctctccaca   120 accctcccccc atgtgcaact gacactcctc cccagtcgat gctcctacct acctttcagc  180
ccacgtcatt cgtagtgtcc atcttgtnaa gccctgttgt gccacacagt ntaacnngcc   240
cccctgcagc ta                                                       252

<210> SEQ ID NO 233
<211> LENGTH: 120
<212> TYPE: DNA
<213> ORGANISM: Rattus norvegicus
<220> FEATURE:
<221> NAME/KEY: unsure
<222> LOCATION: (1)..(120)
<223> OTHER INFORMATION: unsure at all n locations

<400> SEQUENCE: 233
aattctgtgt gaaaancctc anaccacttc tcctgggncc tttaaactcc tggaggttta    60
gggaggccag tttccatccg cactgaattg gggagaanaa aactggnccc aattacgcta   120

<210> SEQ ID NO 234
<211> LENGTH: 47
<212> TYPE: DNA
<213> ORGANISM: Rattus norvegicus

<400> SEQUENCE: 234
aattctaagc cgagtttaac atgttcaaga tatctccgtt tcagcta                  47

-continued

```
<210> SEQ ID NO 235
<211> LENGTH: 121
<212> TYPE: DNA
<213> ORGANISM: Rattus norvegicus
<220> FEATURE:
<221> NAME/KEY: unsure
<222> LOCATION: (1)..(121)
<223> OTHER INFORMATION: unsure at all n locations

<400> SEQUENCE: 235
aattctccga cccggnnata tttgaccctg gccactttt agatgggaat ggaaagttta      60
agaaaagtga ctatttcatg cctttctcag caggaaaacg gatgtgtnca ggagaggcct    120
a                                                                    121

<210> SEQ ID NO 236
<211> LENGTH: 65
<212> TYPE: DNA
<213> ORGANISM: Rattus norvegicus

<400> SEQUENCE: 236
aattcatcca caccaactgg acatgcccac ggtggcagtg tgtcgtcctc ttcatacaat     60
gccta                                                                65

<210> SEQ ID NO 237
<211> LENGTH: 49
<212> TYPE: DNA
<213> ORGANISM: Rattus norvegicus

<400> SEQUENCE: 237
aattccctac acagaccaga actggctttt aactctacca ctacgtcta                49

<210> SEQ ID NO 238
<211> LENGTH: 48
<212> TYPE: DNA
<213> ORGANISM: Rattus norvegicus

<400> SEQUENCE: 238
aattccctgg gtgcctttct ttacaaaatg ggttcaataa ataagcta                 48

<210> SEQ ID NO 239
<211> LENGTH: 74
<212> TYPE: DNA
<213> ORGANISM: Rattus norvegicus

<400> SEQUENCE: 239
aattccatat gtaataggat gcaagtctaa gcgtttcatg tggacataaa tgtatctaaa     60
taaaacttcc ccta                                                      74

<210> SEQ ID NO 240
<211> LENGTH: 142
<212> TYPE: DNA
<213> ORGANISM: Rattus norvegicus
<220> FEATURE:
<221> NAME/KEY: unsure
<222> LOCATION: (1)..(142)
<223> OTHER INFORMATION: unsure at all n locations

<400> SEQUENCE: 240
aattccaggc tgggnttgcc tttctctgct ttcatgacct cttgaccca acgagctgat      60 gttaggacca caacactggt aggtggttaa aaacaagca acaagggctg gggatttagc    120
tcagtggtag agcgcttacc ta                                            142
```

<210> SEQ ID NO 241
<211> LENGTH: 184
<212> TYPE: DNA
<213> ORGANISM: Rattus norvegicus

<400> SEQUENCE: 241

| aattccaaga gtgacttgct ccctcccct tctccaccga aaaccaccca aagtgggaaa | 60 |
| tgaatctctt caccagcacc cctctggcca caggcaaagt atgccacagg cctctgacat | 120 |
| actttggaca gactgccagc taacacccac cacccccatg ttaagacaca tctctggatc | 180 |
| ccta | 184 |

<210> SEQ ID NO 242
<211> LENGTH: 71
<212> TYPE: DNA
<213> ORGANISM: Rattus norvegicus

<400> SEQUENCE: 242

| aattcccaag gtcaaatgcg gttagctgct gtggacttcg atatggaaca tgttacctct | 60 |
| ccctttgcct a | 71 |

<210> SEQ ID NO 243
<211> LENGTH: 391
<212> TYPE: DNA
<213> ORGANISM: Rattus norvegicus

<400> SEQUENCE: 243

| aattcccta cacattggat taatcttact aacatgacaa aaaattgctc cactatcaat | 60 |
| tctataccaa ttttatcaac tcctaagccc aactatcacc accattctcg caatttcatc | 120 |
| agtctttgtt ggcgcctgag gaggacttaa ccagacccaa acacgaaaaa tcatagcata | 180 |
| ttcatcaatt gcccacatag gatgaataac agcaatcctt ccatcaaacc ctaacttaac | 240 |
| cctcctaaac ttaacaattt acatcctact tactgttcca atattcatca cactcataac | 300 |
| aaactcagca acaacaatca acacactctc actcgcatga aataaaactc ccataatcct | 360 |
| aaccatagca tccatcatcc tcctatcact a | 391 |

<210> SEQ ID NO 244
<211> LENGTH: 175
<212> TYPE: DNA
<213> ORGANISM: Rattus norvegicus

<400> SEQUENCE: 244

| aattcgccct gtcgggatga gagagtggga gactgagtaa ccatggctcc gccgtgccct | 60 |
| cactggctct tttccgtgta gcatctctgg gcaagtgagg gaggcatatt agtttccatt | 120 |
| tgcaggtgtg gaacactgag ccccagaaag gacaagaaga ctcattcagt agcta | 175 |

<210> SEQ ID NO 245
<211> LENGTH: 194
<212> TYPE: DNA
<213> ORGANISM: Rattus norvegicus

<400> SEQUENCE: 245

| aattcgccaa ggatgactcc gatagcatga gccgaagaca gacttcttat tctaacaacc | 60 |
| ggagcccaac gaacagcact gggatgtgga aggactcgcc caaatcttcc aaatccatca | 120 |
| gattcattcc tgtctccact tgagccccac gttcacgcag cccgactctt gggagggact | 180 |

```
tttgtgtcca gcta                                                      194

<210> SEQ ID NO 246
<211> LENGTH: 44
<212> TYPE: DNA
<213> ORGANISM: Rattus norvegicus
<220> FEATURE:
<221> NAME/KEY: unsure
<222> LOCATION: (1)..(44)
<223> OTHER INFORMATION: unsure at all n locations

<400> SEQUENCE: 246
aattcgggct ggggatttag ctcagtggan aaacgcttgg ccta                      44

<210> SEQ ID NO 247
<211> LENGTH: 198
<212> TYPE: DNA
<213> ORGANISM: Rattus norvegicus

<400> SEQUENCE: 247
aattctggag atgggacacg aggatcagtt caaggtcatc cttagctact cactgcatag     60
taagtttgag gtctgcctgt gctacatgag accgagggag agaaaggagg ggaaggagtc    120
aagcggtagt tgcctttaat cgcagcattt gggaggcaga ggcaggtgga tctctcggtt    180
tgaggccagc ctggtcta                                                  198

<210> SEQ ID NO 248
<211> LENGTH: 332
<212> TYPE: DNA
<213> ORGANISM: Rattus norvegicus

<400> SEQUENCE: 248
gatccgccac tccttctgca tacatgtcga tgagggctct ctccttcatg tccttcccat     60
agaggttgta tttggtggca atgtagttga gaatggctct ggtctgcacc agcttcatcc    120
catcaatctc caccatgggc acttgctgga acatcaaact cccatcattc cttagcctgg    180
ccaggtcatc ccgagttttc agaaattgtt cttcaaactc tactccagct gcagccagga    240
gccaccggat gggctccatt ctccccctgc catcgaagta gtgaaggact ggcttccccg    300
gcatggcagc aattgcttga gttctcttgt ta                                  332

<210> SEQ ID NO 249
<211> LENGTH: 481
<212> TYPE: DNA
<213> ORGANISM: Rattus norvegicus
<220> FEATURE:
<221> NAME/KEY: unsure
<222> LOCATION: (1)..(481)
<223> OTHER INFORMATION: unsure at all n locations

<400> SEQUENCE: 249
gatcctgggt gttcgcagca cagtcctggg tcactggccc agaggagccg tggtatcaag     60
gcacaaagtg aggaagtggt cctgggaggg gcggggcgg ggcagctccg agctcaggca    120
gtagggcact catggtacca tgaggtggc cagtctgcag gaggcatgga gtgaaggcca    180
gtgctggctc cacttgggaa gaaagggctt acagagcccc ggagtccgag gcagttggtc    240
tctgccancc atggcgtatc caagcctcct atccattccc cctgtacctc tggagatagc    300
ctgtccataa gatggctgtc ctgccctact ggggccactt gaagaacaaa atgtcatttt    360
attctcttga gaaagaaaaa gagggaatc atttttgccc ctgcttggat gcctagaagt    420
ctaataagcc tcattacaaa aagacgtttt ctcggtctca tctggcgttt tctttggctt    480
``` a                                                                481

<210> SEQ ID NO 250
<211> LENGTH: 441
<212> TYPE: DNA
<213> ORGANISM: Rattus norvegicus

<400> SEQUENCE: 250
gatcctgtgg taggagtctt gaaatgcccg ttgaactgct gagaggatac tccacactcc    60
accatcgact tccgtaggct tctcagcaac ttggaattgt tcttgatctt caggtttggt   120
gaccaccatg tgcgtgagag gagtgacaaa attgtacttg agtgacaagt tcagaacttg   180
ggcctcgagg gcctctaact cagctcctga ggctgaaatc tctgctcca gctgttgctg    240
tatggtcagc aacgcccaga gtctctccat aaagttatga agatgtact taggaccctg    300
gaactctttc tcttgttggg ctatgctggc ctccgtttgg aaagtgatgt tctgcaggtg   360
catctgccca ctgactttgg ctaagaggac atcagggccc tggtcccgga cttcccagcc   420
accaccatct ctgagccctt a                                             441

<210> SEQ ID NO 251
<211> LENGTH: 193
<212> TYPE: DNA
<213> ORGANISM: Rattus norvegicus

<400> SEQUENCE: 251
gatccacaca accaaaccaa catgagtgaa agagttagca acacggcctg tggttcgcct    60
atgtttgggt gtcttggagc aaagctgcta tggagaaatg tgcaggtgcc tagggggatgc  120
tgtactgctc tagaggatgt aactcaactc acaggtgac ttttttgatgc ctgacccaat   180
tactagttga tta                                                      193

<210> SEQ ID NO 252
<211> LENGTH: 156
<212> TYPE: DNA
<213> ORGANISM: Rattus norvegicus
<220> FEATURE:
<221> NAME/KEY: unsure
<222> LOCATION: (1)..(156)
<223> OTHER INFORMATION: unsure at all n locations

<400> SEQUENCE: 252
gatcctggga ggatgttgac cacacccttg ggaatgccag ccttcagtgt cagctcggca    60
aacttcaagg ntgtgagtgg ggtcacctgg gcaggcttga tcaccacggt gttcccagcc   120
gccaggcagg ctgcatcttc caggatacca tcatta                             156

<210> SEQ ID NO 253
<211> LENGTH: 101
<212> TYPE: DNA
<213> ORGANISM: Rattus norvegicus
<220> FEATURE:
<221> NAME/KEY: unsure
<222> LOCATION: (1)..(101)
<223> OTHER INFORMATION: unsure at all n locations

<400> SEQUENCE: 253
gatccgaacc caagaggtaa aaaccttccc gcgcgaccag aagtgtccga ggctttcccg    60
gaggcggtgg gacttacttt cccaagaana aagcaggatt a                       101

<210> SEQ ID NO 254

<211> LENGTH: 228
<212> TYPE: DNA
<213> ORGANISM: Rattus norvegicus

<400> SEQUENCE: 254

```
gatctgcacc gttttgaagg aggaattcta ccacagctat ttgcccgtgt gccgcagccc      60
acatcagggg agtaaatcct tcttcatccg tgtgattgat aacattttct tgttcaatac     120
gagtagccag gtagagcatc tctccctgag ctgccaactg gtgaacagac agagaatttg     180
ctaacagagg tgtggtggag acctcgtttc ccctgtgctt gttggtta                   228
```

<210> SEQ ID NO 255
<211> LENGTH: 177
<212> TYPE: DNA
<213> ORGANISM: Rattus norvegicus

<400> SEQUENCE: 255

```
gatctttacg tggtggctct ttaggtagtg gactttattt tactcccaag ggcatcattt      60
caaactctcc ccctcttggt gaaagttcag attccacagc aggtgctgat agtacaacca     120
tgtccatttc ataacaatat gtaggatgtt tgatcttcaa gttggtgaat gctgtta        177
```

<210> SEQ ID NO 256
<211> LENGTH: 447
<212> TYPE: DNA
<213> ORGANISM: Rattus norvegicus

<400> SEQUENCE: 256

```
gatcttgggg tgtgggtagg gatttccagg gtgaaggtag attatttatt agggtgggaa      60
tgtttcattt acatgaagag gaatatgcca agaacctgct ggacaagttc atatcctgaa     120
agaggaagtt gaatctgtaa tctggccata agttatgtga ctttcctcag aggatttctg     180
gggttacagg caggagtggc tgattggtca taacagtacc taattatcat atggtgggaa     240
ggactgagtg ggatgtatgt gctgaacctt gtggcacttg caggaagctt tgtgcaaggc     300
cattctctag ataaggtcag gcacttgtgc ttagaacact ttccagataa gattgggcaa     360
aggagaggaa accccactga gaaagggagt cttccatttt gcaccaggtt cagagagctt     420
atctagacat ggtcgacttc aacctta                                         447
```

<210> SEQ ID NO 257
<211> LENGTH: 350
<212> TYPE: DNA
<213> ORGANISM: Rattus norvegicus

<400> SEQUENCE: 257

```
gatctaaaat acctcgggaa tacatgtcaa tcagggctct ctccttcatg tccttcccat      60
agaggtcata tttggtggcg atgtagttga gaatggctct ggtctgtgcc agcttcatcc     120
cgtcaatctc caccatgggc acttggtcaa acatcaaatt cccgtctttc tttagctttt     180
ccaagtcttc tggactctgt ataaacttct cttcaaactc cactcctgct gcagccagga     240
gccaccggat gcactccatt ctgccccggg cattgaagta gtgaagcact ggcttcccag     300
acatagcagc aactgtgctt tcactgtcta gcgagaatcg tggcttctta                350
```

<210> SEQ ID NO 258
<211> LENGTH: 155
<212> TYPE: DNA
<213> ORGANISM: Rattus norvegicus

<400> SEQUENCE: 258

```
gatcttcacc attggggttc ccagttcttg caaagttggc ccagtacttc atcaccctcc    60
tcttcagcag ctcctcctcc tcagtgaggt caaaggtcat gccccacaag taggagccaa   120
agacaaagag aatgtcatca ccatggtctg cctta                              155
```

<210> SEQ ID NO 259
<211> LENGTH: 37
<212> TYPE: DNA
<213> ORGANISM: Rattus norvegicus

<400> SEQUENCE: 259

```
gatccgtacc ctaggtcaga gctgtgatct ctgctta                             37
```

<210> SEQ ID NO 260
<211> LENGTH: 40
<212> TYPE: DNA
<213> ORGANISM: Rattus norvegicus
<220> FEATURE:
<221> NAME/KEY: unsure
<222> LOCATION: (1)..(40)
<223> OTHER INFORMATION: unsure at all n locations

<400> SEQUENCE: 260

```
gatcctggng atcagtgtgg ggctcacctc caatgggtta                          40
```

<210> SEQ ID NO 261
<211> LENGTH: 224
<212> TYPE: DNA
<213> ORGANISM: Rattus norvegicus
<220> FEATURE:
<221> NAME/KEY: unsure
<222> LOCATION: (1)..(224)
<223> OTHER INFORMATION: unsure at all n locations

<400> SEQUENCE: 261

```
gatcctatgg gctccgtggt cagctagcct agccagcata nggagctcca ggttcagtga    60
gaagacttgt ctcaaaaata gagggaaaa agcaaatgag ttgtcacaa atgtgtactc     120 gtcatacaaa tgccatccat gcaaatgtat acacacacac actcacacac tcacacacac   180
acacacacac acanacanac acacacacnc ncnnataccc atta                    224
```

<210> SEQ ID NO 262
<211> LENGTH: 31
<212> TYPE: DNA
<213> ORGANISM: Rattus norvegicus

<400> SEQUENCE: 262

```
gatcttgaaa agactgtttc cttcatgatt a                                   31
```

<210> SEQ ID NO 263
<211> LENGTH: 53
<212> TYPE: DNA
<213> ORGANISM: Rattus norvegicus

<400> SEQUENCE: 263

```
gatcttcgaa ctaaacgctg gggcgcccac ctccgaatcc caatttctaa tta            53
```

<210> SEQ ID NO 264
<211> LENGTH: 63
<212> TYPE: DNA
<213> ORGANISM: Rattus norvegicus

<400> SEQUENCE: 264

```
gatcctaact cattagtgta aacgaccctc tccagcgtcc ctgcgcccat ctttctgtcc    60
tta                                                                  63
```

<210> SEQ ID NO 265
<211> LENGTH: 105
<212> TYPE: DNA
<213> ORGANISM: Rattus norvegicus

<400> SEQUENCE: 265

```
gatcctattg aggcgagcag ggacctggct ggacaaggac acacttaaaa cccgattttg    60
ttccaaattc tgggaaacat agacatttaa ctctgaagat gccta                   105
```

<210> SEQ ID NO 266
<211> LENGTH: 66
<212> TYPE: DNA
<213> ORGANISM: Rattus norvegicus

<400> SEQUENCE: 266

```
gatctaaagg accaagcagt atgtcagtag ttgttaacgt agcagtagct gtctgtctgt    60
atgcta                                                               66
```

<210> SEQ ID NO 267
<211> LENGTH: 137
<212> TYPE: DNA
<213> ORGANISM: Rattus norvegicus

<400> SEQUENCE: 267

```
gatcttggcc acaaagcagc ccctggctt caagacatga gtagcaatgt taagggcggc    60
aagcagaagc tgggcctgca tgtactcatc tacatcatgg aggccagtga catcaggagc   120
cccgtcacac actacta                                                  137
```

<210> SEQ ID NO 268
<211> LENGTH: 197
<212> TYPE: DNA
<213> ORGANISM: Rattus norvegicus
<220> FEATURE:
<221> NAME/KEY: unsure
<222> LOCATION: (1)..(197)
<223> OTHER INFORMATION: unsure at all n locations

<400> SEQUENCE: 268

```
gatccagtcc cctccagctc tgacntgcta ctgctcagcc aggctccata cctgacaggt    60
tgtttcttgg ctcctctctt gtcatctcac ttgtcctgcc ttctcctgac agtaacagct   120
gttcntcagg tcaactggat caggccccca tgtcctctaa ggagcaggaa gtcctcctac   180
ctaccctacc caccta                                                   197
```

<210> SEQ ID NO 269
<211> LENGTH: 40
<212> TYPE: DNA
<213> ORGANISM: Rattus norvegicus

<400> SEQUENCE: 269

```
gatccgcctc tcccaggagc atcaagccta ccgctggcta                          40
```

<210> SEQ ID NO 270
<211> LENGTH: 109
<212> TYPE: DNA
<213> ORGANISM: Rattus norvegicus

<400> SEQUENCE: 270

```
gatcctattg gagctggtga aataggtcat tttcttatca agaaaaacaa cttctgaaga      60
cagggtttca cacatctcag gattggccat gaactcacta tgcagccta               109

<210> SEQ ID NO 271
<211> LENGTH: 51
<212> TYPE: DNA
<213> ORGANISM: Rattus norvegicus

<400> SEQUENCE: 271
aattcacaag gaaggagctt agaacagaca tctatttctt actgattgtt a              51

<210> SEQ ID NO 272
<211> LENGTH: 36
<212> TYPE: DNA
<213> ORGANISM: Rattus norvegicus

<400> SEQUENCE: 272
aattctacag aaccgtgttt atgatacagc cgttta                               36

<210> SEQ ID NO 273
<211> LENGTH: 36
<212> TYPE: DNA
<213> ORGANISM: Rattus norvegicus

<400> SEQUENCE: 273
aattcagcct taggaaaaaa taaaattgct gcctta                               36

<210> SEQ ID NO 274
<211> LENGTH: 67
<212> TYPE: DNA
<213> ORGANISM: Rattus norvegicus

<400> SEQUENCE: 274
gatccacttt tattaggaac aaatgcaatc tcaaatcagt acaattaggc ttcaagagtt     60
gatatta                                                               67

<210> SEQ ID NO 275
<211> LENGTH: 287
<212> TYPE: DNA
<213> ORGANISM: Rattus norvegicus
<220> FEATURE:
<221> NAME/KEY: unsure
<222> LOCATION: (1)..(287)
<223> OTHER INFORMATION: unsure at all n locations

<400> SEQUENCE: 275
ggcaatgaac cactgtagcg gggctttgca ttgctggctc tacctacagc tattactggt     60
cattggaaga ccttagagtc agaatcttct tgtgtaagag ccctgaatgn tgtgaccaac    120
cccagtgtct acagcatctt tgcagctgtt aatctcactg ttctcgttcc tattgaagaa    180
attactggcc cagaaatgcc tttggtgtgt ttggcagact ttaaggcaca tgcgcaaaag    240
cagctgtcta agacctcctg ggacttattg aaggagaagc tgacgac                  287

<210> SEQ ID NO 276
<211> LENGTH: 260
<212> TYPE: DNA
<213> ORGANISM: Rattus norvegicus

<400> SEQUENCE: 276
ggctccagct ggaaggttga atattgagtg tcctgggagg tcacattgct gtcagacatg     60
```

```
gctgctggac atggtcacga acacggacat ggtcatggta aaatggaact tccagattac    120
agacagtgga aaattgaagg gacgccatta gaagcaatgc agaagaagct tgctgcacga    180
gggctgaggg atccatgggc tcgcaatgag gcttggagat acatgggcgg cttgcagaca    240 atatcaccctt cacgagcgta                                               260

<210> SEQ ID NO 277
<211> LENGTH: 299
<212> TYPE: DNA
<213> ORGANISM: Rattus norvegicus

<400> SEQUENCE: 277
ctacaacagc accagagaca ccattgtgat agagtgggac ttggtgtgca gtccaacaaa     60
ctgaaggaga tggcccagtc gatcttcatg gcaggcatac tggttggagg acctgtgatt    120
ggagaactgt cagacaggtt tggccgcaag cctatcctga cctggagtta tctcatgctg    180
gcagccagcg gctctggtgc tgccttcagt cccagcctcc ctgtctatat gatcttccga    240
ttcctgtgtg gctgcagcat ctcgggcatt tctctgagca ccgttatctt gaatgtgga     299

<210> SEQ ID NO 278
<211> LENGTH: 139
<212> TYPE: DNA
<213> ORGANISM: Rattus norvegicus
<220> FEATURE:
<221> NAME/KEY: unsure
<222> LOCATION: (1)..(139)
<223> OTHER INFORMATION: unsure at all n locations

<400> SEQUENCE: 278
gngagatacc atgatcacga aggtggtttt cccagggcga ggcttatcca ttgcactccg     60
gatgtgctga cccctgcgat ttccccaaat gcgggaaact cgactgcata atttgtggta    120
gtgggggact gcgttcgcg                                                 139

<210> SEQ ID NO 279
<211> LENGTH: 328
<212> TYPE: DNA
<213> ORGANISM: Rattus norvegicus
<220> FEATURE:
<221> NAME/KEY: unsure
<222> LOCATION: (1)..(328)
<223> OTHER INFORMATION: unsure at all n locations

<400> SEQUENCE: 279
gatagactca ggaagcaatc atggtgctct ctgcagatga caaaaccaac atcaagaact     60
gctgggggaa gattggccat ggtggtgaat atggcgagga ggccctacag aggatgttcg    120
ctgccttccc caccaccaag acctactctc tcacattga tgtaagcccc ggctctgccc    180
aggtcaaggc tcacggcaag aaggttgctg atgccttggc caaagctgca gaccacgtcg    240
aagacctgcc tggtgccctg tccactctga gcgactgcat gcccacaact gcgtgtggat    300
cctgtcantt cagttcctga gccatgct                                       328

<210> SEQ ID NO 280
<211> LENGTH: 312
<212> TYPE: DNA
<213> ORGANISM: Rattus norvegicus

<400> SEQUENCE: 280
ttacaaccca ggtgtggatg ctggagtgtt tcctttgtct tctattttaa agatatcttg     60
```

```
aaaaaaacct gtcactgtcc ttttcctgcg accatgtctt ccatcaagat tgaatgtgtt    120
ttaagggaga actacaggtg tggggagtcc cctgtgtggg aggaggcatc aaagtgtctg    180
ctgtttgtag acatcccttc aaagactgtc tgccgatggg attcgatcag caatcgagtg    240
cagcgagttg gtgtagatgc cccagtcagt tcagtggcat tcgacagtca ggaggctatg    300
ttgccaccat gg                                                         312

<210> SEQ ID NO 281
<211> LENGTH: 289
<212> TYPE: DNA
<213> ORGANISM: Rattus norvegicus
<220> FEATURE:
<221> NAME/KEY: unsure
<222> LOCATION: (1)..(289)
<223> OTHER INFORMATION: unsure at all n locations

<400> SEQUENCE: 281
ccttgaacgg acatgacnct ganaagttag aaatgagctc agggacccgg agaccccgcnt    60 cattctccct agcctgcntc tcttgccccg naacgcgggg ngcaggtttg ctcctaaaan    120
ctctgtgcat cttcgatgat aaggaccaac agctgggggt gtagctcagg gcagagtctt    180
gcctggnaag cccggatgcn ttgaggcctt gaccaccnc agcacanana naaaatgaag     240
gaagacccaa ggnaccttct ggaagacctc atccccaaan aagcaagtg                289

<210> SEQ ID NO 282
<211> LENGTH: 250
<212> TYPE: DNA
<213> ORGANISM: Rattus norvegicus

<400> SEQUENCE: 282
actgactgta ctggtcagga ggtcacagat ccagccaaat gcaacctgct ggcagaaaag    60
caatatggct tctgcaaggc gactctcatc cacagacttg gtggggaaga ggtttcagtg    120
gcctgcgcct gtagccccac cagctggccc acctgaatcc gtggtggtag gacccgtggc    180
agttcctcta ggacttccag accaccgaac ccaccatgac ctacggcatg ccttctctcc    240
tgtggcttct                                                           250

<210> SEQ ID NO 283
<211> LENGTH: 285
<212> TYPE: DNA
<213> ORGANISM: Rattus norvegicus
<220> FEATURE:
<221> NAME/KEY: unsure
<222> LOCATION: (1)..(285)
<223> OTHER INFORMATION: unsure at all n locations

<400> SEQUENCE: 283
agccactgtn gccgatctcg cgcacgcnaa ctgctgctgn tngcacgtag tcccccatcg    60
tgcannaanc ggtcncaaaa gattcnaann caagatggna gcccncacg aacaggncat    120 tgtgaatgtn cttaaggaag aacaggtncc ccanaacaan atnaaagttg ttgggggtgg    180
tgtgntggca ngggttgtgc catcagnanc tcaangaang actgggtgat gagntgcccc    240
ttgttgatgn cacacaagan aanctaaacn gagagangan cgatc                    285

<210> SEQ ID NO 284
<211> LENGTH: 266
<212> TYPE: DNA
<213> ORGANISM: Rattus norvegicus
<220> FEATURE:
<221> NAME/KEY: unsure
```

```
<222> LOCATION: (1)..(266)
<223> OTHER INFORMATION: unsure at all n locations

<400> SEQUENCE: 284
gaccctgtnt ccaggagcca acagctagac tggtcccagt cagacgnagg aaacctggnc    60
cagcttttgc actttcnang tgacgatggn cntacagagg acccaatcct tgcttctgct   120
ctgttgctga ccctgctggg gttagggttg tacagccctc ctatggccaa gatagaatgt   180
accaacggtt ccttagacag catgtggacc ctgagggac aggcggcagg acaactactg    240
caacgtgatg atgcagagac ggaggt                                        266

<210> SEQ ID NO 285
<211> LENGTH: 250
<212> TYPE: DNA
<213> ORGANISM: Rattus norvegicus

<400> SEQUENCE: 285
gtagctttcc cctttgctg gcacagaagt ctgtccatct gcaagcgctt tggaacacag     60
actgcctgga gccaccttcc tttgggagac cttcctgcct cagctgtcgt cctgtgtcgt   120
cattcactaa agctcctgac gtcagattaa gcaagcagtg atgggttaca ttagagacaa   180
gccgcagaga taaggcctgt tgctgttcg cagataatga tgagttttaa ttacccactg    240
gtttgtatgg                                                          250

<210> SEQ ID NO 286
<211> LENGTH: 118
<212> TYPE: DNA
<213> ORGANISM: Rattus norvegicus
<220> FEATURE:
<221> NAME/KEY: unsure
<222> LOCATION: (1)..(118)
<223> OTHER INFORMATION: unsure at all n locations

<400> SEQUENCE: 286
gtangactng catcggcaag ggctacagag gaaccatgtn caagacaaag actggtgtta    60
ccnntncaat agtggagtga gcacgtgccc cccacgtagc ccaaanactc ccccaggc     118

<210> SEQ ID NO 287
<211> LENGTH: 262
<212> TYPE: DNA
<213> ORGANISM: Rattus norvegicus
<220> FEATURE:
<221> NAME/KEY: unsure
<222> LOCATION: (1)..(262)
<223> OTHER INFORMATION: unsure at all n locations

<400> SEQUENCE: 287
gagagnacct ttgtctcgga gtaactcccg taccccaagt cctaaaagcc ttccgtctta    60
cctcaatggg gtcatgcctc caacacagag ctttgccccc gacccaagt atgtcagcag    120 caaagccctg cagaganaga gcagcgaagg gtctgccaag gcccctgca tcctgcccat    180 ncattgagaa tgggaagaag gtcagctcca gcnttattca cctactacct gagcggacgg   240
cancaccttg ncaaatatga gc                                            262

<210> SEQ ID NO 288
<211> LENGTH: 282
<212> TYPE: DNA
<213> ORGANISM: Rattus norvegicus
<220> FEATURE:
<221> NAME/KEY: unsure
<222> LOCATION: (1)..(282)
```

<223> OTHER INFORMATION: unsure at all n locations

<400> SEQUENCE: 288

```
tgagctgcnc ctgacatttg tccatctccc aaannctctc tggagcancc ntngaagtcc      60
ctngtcctgc tcctttnnnt tgctcagatt ctagagctgc caatcagctc cacaaggtgc     120
agggctgggt tttcgagaat tggctttnat gacccggaaa aaaanccntt nanctttgat     180
agccgtggac tacctcaata aacatcttct tcagggattc aggcagatct tgaatcagat     240
gacaaagtaa ggtgtggtct cggcggccct tcgganaggt gt                        282
```

<210> SEQ ID NO 289
<211> LENGTH: 265
<212> TYPE: DNA
<213> ORGANISM: Rattus norvegicus

<400> SEQUENCE: 289

```
catagaccca tctctcagct gggatgatat taaatggctc agacggttga cctcactgcc      60
cattgttgta aagggaattt tgagaggtga tgatgcccag gaagctgtta aacatggtgt     120
ggatgggatc ttagtgtcga atcatggggc acgacaactg gatggggtgc cagctactat     180
tgatgccctg ccagagatcg ttgaggctgt ggaagggaag gtagaagtct tcctggatgg     240
gggagtcagg aaaggcaccg atgtt                                            265
```

<210> SEQ ID NO 290
<211> LENGTH: 199
<212> TYPE: DNA
<213> ORGANISM: Rattus norvegicus
<220> FEATURE:
<221> NAME/KEY: unsure
<222> LOCATION: (1)..(199)
<223> OTHER INFORMATION: unsure at all n locations

<400> SEQUENCE: 290

```
ccctgcaagc tgtgttgcag ggcccggaag gctcactgtt ccgaaatggc cgacagtcag      60
acaaggatgt gagatacact ctggagagat cagagacaag cacaganact gtgtcncact     120
agtgncgttg cagtctnaac atctgtggag atcnanncan tggtanntna ctggcncgan     180
ncgtncnatg caaannacg                                                   199
```

<210> SEQ ID NO 291
<211> LENGTH: 285
<212> TYPE: DNA
<213> ORGANISM: Rattus norvegicus
<220> FEATURE:
<221> NAME/KEY: unsure
<222> LOCATION: (1)..(285)
<223> OTHER INFORMATION: unsure at all n locations

<400> SEQUENCE: 291

```
tacgcaccat ggacacangc acangcctca tcaganctat gcatagtagt ntaaatcana      60
agtgtgatct tgttcaacta cagttatgga gaagcaactc attggccagn ttctgggaga     120
ntttgtgnng tanttaatgc agcngtatgg naacnnaata cnatttangt ttcnggtgct     180
gntantaatg gtcnatgcct tctacagtgg gttgtccann nggantactt ccancgnnat     240
aggngntgga gcntatgttc tcgccgatat ganggttgcn gngta                     285
```

<210> SEQ ID NO 292
<211> LENGTH: 268
<212> TYPE: DNA
<213> ORGANISM: Rattus norvegicus

```
<220> FEATURE:
<221> NAME/KEY: unsure
<222> LOCATION: (1)..(268)
<223> OTHER INFORMATION: unsure at all n locations

<400> SEQUENCE: 292
ccacgctgga gcgaanacca ttgctcgtga gcacatgggg agactgctgc accagctact      60
ctgcgcaggg cacctctcta ctgtccagta ctaccaaggg ctgtatgaaa cactagaatt     120
ggctgaggac atggaaatcg acatccctca tgtatggctt tacctggcag aactgataac     180
acctattctt caggaagacg gggtacccat gggagagctc tttagggaaa ttacgaagcc     240
tctgagaccc atgggcaaag ccacttct                                        268

<210> SEQ ID NO 293
<211> LENGTH: 185
<212> TYPE: DNA
<213> ORGANISM: Rattus norvegicus
<220> FEATURE:
<221> NAME/KEY: unsure
<222> LOCATION: (1)..(185)
<223> OTHER INFORMATION: unsure at all n locations

<400> SEQUENCE: 293
ctcattgcca ccatgaactt ctccggcaag taccaagtgc agagccaaga gaactttgag      60
cccttcatga aggcgatgg gtctgctgag gacttcatcc nagaaaggga aggacntcaa     120 ggggtntnn gaatncngcn nnnanggaag aaantnnaac tcnccatcan ctannggncc     180 aangt                                                                 185

<210> SEQ ID NO 294
<211> LENGTH: 286
<212> TYPE: DNA
<213> ORGANISM: Rattus norvegicus
<220> FEATURE:
<221> NAME/KEY: unsure
<222> LOCATION: (1)..(286)
<223> OTHER INFORMATION: unsure at all n locations

<400> SEQUENCE: 294
agctaagtag aaaaatatgt gtgaataaag ccaataatat ctcccanatg ttattaccaa      60
ttaataagat gttctatttt ctggtatgat ataaaattat ctctacttaa tgtcataact     120
ggcaaaaaaa aaactatcat tgcaaatgcc tcccagtgaa accaataact tctcanatat     180
ttagaattat tggttataac tcactaacct agtttcctaa natcanttta anatttgatt     240
tatngtanag cantggnnaa tgatgccnct ctnatgttgt ttnnac                    286

<210> SEQ ID NO 295
<211> LENGTH: 225
<212> TYPE: DNA
<213> ORGANISM: Rattus norvegicus

<400> SEQUENCE: 295
gcctcccggc ttgcctgccc agttttatcc ctagaagcag ctagctactc caggtgcaca      60
ggtgccatgc agccccgaat gctcctcatc gtggccctcg tggctctcct ggcctctgcc     120
cgagctgatg agggagaggg atccttgctg ctgggctcta tgcagggcta catggaacaa     180
gcctccaaga cggtccagga tgcactaagc agcatgcagg agtct                     225

<210> SEQ ID NO 296
<211> LENGTH: 278
<212> TYPE: DNA
```

<213> ORGANISM: Rattus norvegicus
<220> FEATURE:
<221> NAME/KEY: unsure
<222> LOCATION: (1)..(278)
<223> OTHER INFORMATION: unsure at all n locations

<400> SEQUENCE: 296

| | | |
|---|---|---|
| acaccatcna cctgtatgcn gtnactggcc gtgnggacat tccagccagc agcaagccat | 60 |
| nttccatcaa ntatcanaca naaattgaca agccatccca natgcangtg acggntgtcc | 120 |
| aggacaacag catcagtgtc aggtggctgc cttcaattct nctgtggaca ggtaccgagg | 180 |
| nccagcggtt ccncaaaant gggtactgac naacanaatc tcaaactgtc nagtccagat | 240 |
| canacagaga tgnccattga aggntgcaac ccaccgtg | 278 |

<210> SEQ ID NO 297
<211> LENGTH: 290
<212> TYPE: DNA
<213> ORGANISM: Rattus norvegicus
<220> FEATURE:
<221> NAME/KEY: unsure
<222> LOCATION: (1)..(290)
<223> OTHER INFORMATION: unsure at all n locations

<400> SEQUENCE: 297

| | | |
|---|---|---|
| gtggaaagga aacctcattg ccaccatgaa cttctccggc aagtaccaag tgcagagcca | 60 |
| agagaagttc gaggtggana ggaaacctca ttgccaccat gaacttctcc ggcaagtacc | 120 |
| aagtgcagag ccaagagaac tttgagccct tcatgaaggn nanggnctg nctnaggnct | 180 |
| tcatncngaa angganggnc atcaaggggg tgtcagntat nctgcatgan gggganctcnt | 240 |
| caaatnanca ncactatgng tncaagtgat cnaatgagtt cacttggggc | 290 |

<210> SEQ ID NO 298
<211> LENGTH: 296
<212> TYPE: DNA
<213> ORGANISM: Rattus norvegicus
<220> FEATURE:
<221> NAME/KEY: unsure
<222> LOCATION: (1)..(296)
<223> OTHER INFORMATION: unsure at all n locations

<400> SEQUENCE: 298

| | | |
|---|---|---|
| agcaagccta tttctgactg gnctgctgtg cagaatctag accactggca gtgggtgaca | 60 |
| gcccagttga ggttaatcga agtctcgtcg caggctctgc tgtaagtctg gcctcttggc | 120 |
| ctcacatctt ctttgtggga tccttcccta tctccagctt cctcagctgg tcaggagat | 180 |
| ttggtccaga actagaagcc ttaataatct gagcaggtaa gagaggagta aaatgtacag | 240 |
| tcttggacat tgactaaagg gtcctgcaga ggatatcaag gtaagtggct tggagg | 296 |

<210> SEQ ID NO 299
<211> LENGTH: 277
<212> TYPE: DNA
<213> ORGANISM: Rattus norvegicus
<220> FEATURE:
<221> NAME/KEY: unsure
<222> LOCATION: (1)..(277)
<223> OTHER INFORMATION: unsure at all n locations

<400> SEQUENCE: 299

| | | |
|---|---|---|
| ggtggccctg ccttgtcttg gctctgctct ctggcttgga gacctctggc tttccaagga | 60 |
| gtcccctccg gctgcttggg aaacggagcc ttccagaagg ggtggtggat gcattgagat | 120 |
| ctacagcacc aagatcagct gcaaggtgac ctcccgcttt gctcacaatg ttgtcaccac | 180 |

```
aagggctgtc aaccgtgcag acaaggccaa gaagtttcct ttgatgtgga ctgcccaaga      240
cagcctncat caccaacttc accttgatat ngatggg                               277
```

<210> SEQ ID NO 300
<211> LENGTH: 287
<212> TYPE: DNA
<213> ORGANISM: Rattus norvegicus

<400> SEQUENCE: 300

```
ctcagtttct gaagagaagc accctggcac agttcttctg agttttggac ctaggtctac      60
aaccatgaag gtagcaatta tctttcttct cagtggcttt ggccctgctc aatttagcag     120
gtaacactac agctaaggtg attgggaaaa aggctaattg ccctaataca cttgttggat     180
gccccaggga ttatgatcct gtgtgtggta ctgacggaaa aacttacgcc aatgaatgca     240
ttctatgctt tgaaaacagg aaatttggaa catctatccg cattcag                   287
```

<210> SEQ ID NO 301
<211> LENGTH: 85
<212> TYPE: DNA
<213> ORGANISM: Rattus norvegicus
<220> FEATURE:
<221> NAME/KEY: unsure
<222> LOCATION: (1)..(85)
<223> OTHER INFORMATION: unsure at all n locations

<400> SEQUENCE: 301

```
tttcttctga cgctaggnaa cattccagtg tagctgaggc tgtcccaaac ccagtgaggn      60
gcccaggatg ttcctgaaag ggctg                                            85
```

<210> SEQ ID NO 302
<211> LENGTH: 295
<212> TYPE: DNA
<213> ORGANISM: Rattus norvegicus
<220> FEATURE:
<221> NAME/KEY: unsure
<222> LOCATION: (1)..(295)
<223> OTHER INFORMATION: unsure at all n locations

<400> SEQUENCE: 302

```
gcgacacagg tgaaccatnt ctnctgacgc taggaaacat ccagtgtagc tgaggctgtc      60
ccaacccagt gaggagccca ggatgtnccn gaaggctgtg gtgctgaccg tggccctggt     120
ggccatcacc gggacccagg ctgaggtcac ttccgaccng gtggccaatg tgatgtggga     180
ctacttcacc cagcnaagca acaatgccaa ggaggctgtg gaacaactgc agaagacaga     240
tgtcactcaa cagctcaata ccctcttcca ggacaaactt ggaacattaa cacct          295
```

<210> SEQ ID NO 303
<211> LENGTH: 279
<212> TYPE: DNA
<213> ORGANISM: Rattus norvegicus
<220> FEATURE:
<221> NAME/KEY: unsure
<222> LOCATION: (1)..(279)
<223> OTHER INFORMATION: unsure at all n locations

<400> SEQUENCE: 303

```
cttcatctct cttggggccc catggggcgg ttccatcaag cccatgcgga tcctggcctc      60
aggtgacaac cagggcatcc cgatcatgtc caacataaag ctgagagaag aacagcgcat     120
aaccacaact tcccccctgga tgtttccagc tcaccacgtg tggcctgaag accacgtgtt    180
```

```
catttccaca ccaaacttca cnacacaggc caagacttcg agcgtttttt tgcagatctt      240
cattttgaag aaggctggca catgtttcta cagtctcgt                            279
```

<210> SEQ ID NO 304
<211> LENGTH: 306
<212> TYPE: DNA
<213> ORGANISM: Rattus norvegicus

<400> SEQUENCE: 304

```
cttgggagtc ctcggctgct tacaacttgg agccacctgt gtcctggccc ccaagttctc      60
tgcttcccga tactgggctg agtgccggca gtacagtgtg acagtggtcc tgtatgtggg     120
tgaagtcctg cgatacttgt gtaatgtccc agggcaacca gaagacaaga aacatacagt     180
gcggttcgca ttgggcaatg gacttcgggc agacgtgtgg gaaaacttcc agcaacgatt     240
tggtcccatt cagatctggg aactctacgg ctccacagag ggcaacgtgg gcttaatgaa     300
tatggg                                                               306
```

<210> SEQ ID NO 305
<211> LENGTH: 296
<212> TYPE: DNA
<213> ORGANISM: Rattus norvegicus

<400> SEQUENCE: 305

```
gggtttctct gtatttaccc ctacaagatc cctggatggt gtctctgggt tcttccaagg      60
ggccttcctg ctcagtctat ttctggtgct gttcaaggca gtccaattct acttacgaag     120
gcaatggctg ctcaaggccc tcgagaagtt cccatccacg ccttcccact ggctttgggg     180
ccacgacctg aaggacagag aattccagca ggttcttacg tgggtagaga aattcccagg     240
tgcctgctta cagtggctct cagggagcaa aacacgagtc ctgctctatg accctg         296
```

<210> SEQ ID NO 306
<211> LENGTH: 147
<212> TYPE: DNA
<213> ORGANISM: Rattus norvegicus
<220> FEATURE:
<221> NAME/KEY: unsure
<222> LOCATION: (1)..(147)
<223> OTHER INFORMATION: unsure at all n locations

<400> SEQUENCE: 306

```
tcagcttcgg tgcntcccat gagncntccc tgcaatcagn aactatgctt tccctgaggg      60
tcncctgctt catcctnagc ttggccagca cagtctggac tgcagacacc ggcaccacaa     120
ttgaattcat anaagcagga ggnnata                                         147
```

<210> SEQ ID NO 307
<211> LENGTH: 312
<212> TYPE: DNA
<213> ORGANISM: Rattus norvegicus
<220> FEATURE:
<221> NAME/KEY: unsure
<222> LOCATION: (1)..(312)
<223> OTHER INFORMATION: unsure at all n locations

<400> SEQUENCE: 307

```
gcatccgcta agtgcgtggt gcgaactgnc gctgggtgcg gttgtcgcgg tcgccactgc      60
ctctcggtcc aatgagctgc accaggatga tccacgtgct ggatccacga cctttgacaa     120
gttcagtcat gcccgtggac atggccatga ggatttgctt ggcacattca ccaccctga     180 agagtttcct gggtccttac aatggtcttc agcgaagaca ttttgtgaat aaaccgaagc     240
```

```
ccttgaaacc gtgtctcagc gtcaagcagg aagccaaatc acagaaggaa tggaagagcc    300
cacacagcca ag                                                        312
```

<210> SEQ ID NO 308
<211> LENGTH: 284
<212> TYPE: DNA
<213> ORGANISM: Rattus norvegicus
<220> FEATURE:
<221> NAME/KEY: unsure
<222> LOCATION: (1)..(284)
<223> OTHER INFORMATION: unsure at all n locations

<400> SEQUENCE: 308

```
gtcagtttca ctgtggaggt cctgcttcca gacaaagcag cagaagagaa gttgaatcag     60 caggggcag tcaccccaa ataacatctc cctcctgcag caggcctggc cccctcagt       120 gtcttcctgt cagtttcttt atagtcattt tcctacaacc tattagccca agaaactgg    180 gctggaggga agacttcaga ctggacggag cacccgttca gagtcagaag cggataanta   240
gctagagggg tcctccncat cagaatacta aagggtctcc agag                    284
```

<210> SEQ ID NO 309
<211> LENGTH: 293
<212> TYPE: DNA
<213> ORGANISM: Rattus norvegicus

<400> SEQUENCE: 309

```
gtagccactc taactagggg cgtgctgaga caagaccacc tcattcctct gctgcttttc     60
agacaggact gtcctgccga cccaccatga tccaggctgc actgttcctt ggctgtatct   120
tactgtcctc ggtgaccgcc tttccatgga agactcagga tggtggcctg ccccatcagc   180
cagctggcac agaaactgag cctacacaac tgctctacag caagagtcct cctccgacct   240
ccagtacctg tcggaacctc ctaagcatgg cgcccctgcc cctgtagtc ctc           293
```

<210> SEQ ID NO 310
<211> LENGTH: 208
<212> TYPE: DNA
<213> ORGANISM: Rattus norvegicus
<220> FEATURE:
<221> NAME/KEY: unsure
<222> LOCATION: (1)..(208)
<223> OTHER INFORMATION: unsure at all n locations

<400> SEQUENCE: 310

```
gtccctgang cctacaccat cctgcgtgag agatgcccgt ctcattttga ctcagagtct     60
gtccctctgc ttgtcttctn caagccatnt ggctctacct gctggcactg gtgggcctgt   120
ggaacctcct gcgcttgttc agggagngga nngtggtnag cnatctccaa gacaagtatg   180
tcttcatcac gggctgtgat caggcttt                                       208
```

<210> SEQ ID NO 311
<211> LENGTH: 280
<212> TYPE: DNA
<213> ORGANISM: Rattus norvegicus
<220> FEATURE:
<221> NAME/KEY: unsure
<222> LOCATION: (1)..(280)
<223> OTHER INFORMATION: unsure at all n locations

<400> SEQUENCE: 311

```
ggctgtaatg gggctgcctg gctccccttg gcagtgggtg ctgttgctgt tggggctact     60
```

```
gctccctcct gccaccnnct tctggctcct caatgtgctc ttcccccgc acaccacgcc    120 caaggctgaa ctcagtaacc acacacggcc tgtcatcctg tgcctggct gcatggggaa    180 ccggctagaa gccaagcttg ataaaccaaa tgtggtaaac tggctgtgct accgaaanac   240
agaggatttt ttaccacngn ctggattcan anntttcnnc                        280
```

<210> SEQ ID NO 312
<211> LENGTH: 181
<212> TYPE: DNA
<213> ORGANISM: Rattus norvegicus
<220> FEATURE:
<221> NAME/KEY: unsure
<222> LOCATION: (1)..(181)
<223> OTHER INFORMATION: unsure at all n locations

<400> SEQUENCE: 312

```
ctggaacact ttaattctgt ccacaagggc agagtgnacn aactcccagc aatctaggac    60 tncaacctt agcctttagc ctcactcctg agggttatgg tgatcaattt tcctggatct    120
gaagacttgg acatggactg agacctcagt tacagacagc ctgttgtgag acttctcagc   180
c                                                                   181
```

<210> SEQ ID NO 313
<211> LENGTH: 174
<212> TYPE: DNA
<213> ORGANISM: Rattus norvegicus
<220> FEATURE:
<221> NAME/KEY: unsure
<222> LOCATION: (1)..(174)
<223> OTHER INFORMATION: unsure at all n locations

<400> SEQUENCE: 313

```
cacnaagcta tntataatgg ccagactata cttggtttga aggaatacct tttcatgcct    60
ttgggattgc cnaaganaac tttgcaaaat gtttgtaata aagtttgtgg tgaaanacga   120
agatttgatt tcattggctt atcccaagtc aggaacgacg cgccggctcg naat         174
```

<210> SEQ ID NO 314
<211> LENGTH: 289
<212> TYPE: DNA
<213> ORGANISM: Rattus norvegicus
<220> FEATURE:
<221> NAME/KEY: unsure
<222> LOCATION: (1)..(289)
<223> OTHER INFORMATION: unsure at all n locations

<400> SEQUENCE: 314

```
atttttgttt acccactcga gaagtaagcg ccaaaggggc tagtaagaga acagacagcg    60
ctggtggtgg ctatttgctc caggcctaac cagtggggaa gtggatttgc gggacacgtg   120
tctcagcctg gacacttagg ggttcttagc ttgtgaagcc aatccnggtg gaaccgatgt   180
ggatnaggnt gcantgnnnc tctgtttccc cccaaacttc cccagtaacc tttgggcaag   240
gtggatgaac ncagngattt ttgaaaagtc aaaaacttcg gtttgttta                289
```

<210> SEQ ID NO 315
<211> LENGTH: 309
<212> TYPE: DNA
<213> ORGANISM: Rattus norvegicus

<400> SEQUENCE: 315

```
gcccagtgtt ctaggaccac tgccatggag gacccagaca agaaagggga agccagagcc    60
gggagcgaag tagggtctgc cagccccgag gagcaacttg acggatcagc cagcccagtg   120
```

```
gagatgcagg atgagggatc agaggagctt cacgagacag gagagcccct gcccccttc      180 ctgctgaagg agggtggaga tgaggggcta cactcggcag agcaggatgc cgatgatgag      240
gcagctgatg atacagatga caccagctcg gtgacctcct ctgccagtct accacctcct      300
ctcagagtg                                                              309
```

```
<210> SEQ ID NO 316
<211> LENGTH: 211
<212> TYPE: DNA
<213> ORGANISM: Rattus norvegicus

<400> SEQUENCE: 316
cagacctcca ggagaacctg gaagaagtcc ttcccaagct gctagctgag aacattcgat      60
gcttctacct tggccacagc tcacccactc cgggcgtaga ggctctagga gctgccctgg     120
acgctgcacc ttctgaccca gtgcctgcca agcttcgtgc taatataaag tggaaatccc     180
cagccatatt catctatact tcagggacca c                                    211
```

```
<210> SEQ ID NO 317
<211> LENGTH: 282
<212> TYPE: DNA
<213> ORGANISM: Rattus norvegicus
<220> FEATURE:
<221> NAME/KEY: unsure
<222> LOCATION: (1)..(282)
<223> OTHER INFORMATION: unsure at all n locations

<400> SEQUENCE: 317
agccggcagc cgagtcggat tgngctgctg cagacgccag gccactccag ccagcactgc      60
cgttttcacg ccccggctgc agacagctag gaggctttat ctagtttgaa ccaggctgct     120
ggagctcgct ccttccctct cttttttttcc acgaggctgt ttttttattt ggctgcatgc    180
atgaaatccc aatggtgtag accagtggcg atggatctag gagtttacca actgagacat     240
ttttcaattt ctttcttgtc gtctttgctg ggaatgaaaa cg                        282
```

```
<210> SEQ ID NO 318
<211> LENGTH: 261
<212> TYPE: DNA
<213> ORGANISM: Rattus norvegicus
<220> FEATURE:
<221> NAME/KEY: unsure
<222> LOCATION: (1)..(261)
<223> OTHER INFORMATION: unsure at all n locations

<400> SEQUENCE: 318
aagggagaga aatcaatgaa ttttcaatct tgttttttta atgaggcagt gatattatag      60
catggttaaa ctgctttaat ttacactttt gattgggtgc tggggaataa acctaaagca     120
tggcatatta atgaagaaca tatggtaacc atgaactcca tctctggatt cctttatcgg     180
cnatttttta aaggttgaat attcgcacca gagaatgaca agtggttttg acaacatact     240
ctaggccttc tattaaaaac a                                               261
```

```
<210> SEQ ID NO 319
<211> LENGTH: 273
<212> TYPE: DNA
<213> ORGANISM: Rattus norvegicus

<400> SEQUENCE: 319
cgtggttaca ccaggaccat ggagcccagt atcttgctcc tccttgctct cctcgtgggc      60
```

```
ttcttgttac tcttagtcag gggacaccca aagtcccgtg gcaacttccc accaggacct      120 cgtcccttc ccctcttggg gaacctcctg cagttggaca gagggggcct cctcaattcc       180
ttcatgcagc ttcgagaaaa atatggagat gtgttcacag tacacctggg accaaggcct     240
gtggtcatgc tatgtgggac agacaccata aag                                   273
```

<210> SEQ ID NO 320
<211> LENGTH: 205
<212> TYPE: DNA
<213> ORGANISM: Rattus norvegicus
<220> FEATURE:
<221> NAME/KEY: unsure
<222> LOCATION: (1)..(205)
<223> OTHER INFORMATION: unsure at all n locations

<400> SEQUENCE: 320

```
ccaggaccat ggagcccagt atcttgctcc tccttgctct ccttgtgggt tcttgttact      60
cttagtcagg ggacaccnaa attccntggg aaatttccna caagacttg nnccctttcc      120 cntntngggg aacncntgaa nttggaaana ggaggcntcc tnantncntt cangnagttt    180
cgcgaaaaat atgganatgt ntnca                                            205
```

<210> SEQ ID NO 321
<211> LENGTH: 289
<212> TYPE: DNA
<213> ORGANISM: Rattus norvegicus

<400> SEQUENCE: 321

```
caccaggacc atggagccca gtatcttgct cctccttgct ctccttgtgg gcttcttgtt      60
actcttagtc aggggacacc caaagtcccg tggcaacttc ccaccaggac ctcgtcccct    120 tccctcttg gggaacctcc tgcagttgga cagaggaggc ctcctcaatt ccttcatgca     180
gtttcgcgaa aaatatggag atgtgttcac agtacacctg gaccaaggc ctgtggtcat     240 gctatgtggg acagacacca taaggaggc tctggtgggc caagctgaa                  289
```

<210> SEQ ID NO 322
<211> LENGTH: 265
<212> TYPE: DNA
<213> ORGANISM: Rattus norvegicus
<220> FEATURE:
<221> NAME/KEY: unsure
<222> LOCATION: (1)..(265)
<223> OTHER INFORMATION: unsure at all n locations

<400> SEQUENCE: 322

```
gccatttggc tcccaaggac attgacctca cgcccaagga gagtggcatt ggaaaaatac      60
ctccaacgta ccagatctgc ttctcagctc ggtgatccgg ctgaggcagc catgtgcccc    120
agttctgttg ggaatggcct catgtttctg cctctggggg acctgctgaa aaccaggctc     180
aaggccactg ctcacatctt cctattgcag ttctccaaag tcccaaggct ttttcntatt     240
cctgtgaatg gcactgaaga agtca                                            265
```

<210> SEQ ID NO 323
<211> LENGTH: 234
<212> TYPE: DNA
<213> ORGANISM: Rattus norvegicus

<400> SEQUENCE: 323

```
gtaaaatgcc atacactgat gcagttatcc atgagattca gaggttttca gatcttgtcc      60
ctattggagt accacacaga gtcaccaaag acaccatgtt ccgagggtac ctgcttccca    120
```

| agaacactga agtgtacccc atcctgagtt cagctctcca tgacccacag tactttgacc | 180 |
| acccagacag cttcaatcct gaacacttcc tggatgccaa tggggcactg aaaa | 234 |

<210> SEQ ID NO 324
<211> LENGTH: 235
<212> TYPE: DNA
<213> ORGANISM: Rattus norvegicus
<220> FEATURE:
<221> NAME/KEY: unsure
<222> LOCATION: (1)..(235)
<223> OTHER INFORMATION: unsure at all n locations

<400> SEQUENCE: 324

| gaaacttggt cattctagca gcacagantc agaactgaga actggccatg gcacggaaac | 60 |
| aaccacatag ctggctgaan gctgtgctct ttgggctcct gcttattctt atccatgtgt | 120 |
| ggggtcagga ctcaccagag tccagctcca tcaggaccac acaanatann attnanaaan | 180 |
| gnaagcttga cnacgtgagg gacactaaag ctggtgtcca nacaacanaa ngttc | 235 |

<210> SEQ ID NO 325
<211> LENGTH: 263
<212> TYPE: DNA
<213> ORGANISM: Rattus norvegicus
<220> FEATURE:
<221> NAME/KEY: unsure
<222> LOCATION: (1)..(263)
<223> OTHER INFORMATION: unsure at all n locations

<400> SEQUENCE: 325

| aaagtcccaa ggnttgttct tattcctgtg aatggcactg aagaagtcaa tcgactgtct | 60 |
| tattttgaca tgtgaacaga gatttcatga gtacacatct catgctgagt cacttccctc | 120 |
| ttcctcctaa tagcccacgt ccccacttat cagccctcca tggtctgtga tctgtgctaa | 180 |
| tggactctgt atatggtctc agtgctatgt ctacagactt acatagtatg tatggttcag | 240 |
| gtaaacagat cacagagtgt gtg | 263 |

<210> SEQ ID NO 326
<211> LENGTH: 300
<212> TYPE: DNA
<213> ORGANISM: Rattus norvegicus
<220> FEATURE:
<221> NAME/KEY: unsure
<222> LOCATION: (1)..(300)
<223> OTHER INFORMATION: unsure at all n locations

<400> SEQUENCE: 326

| gtgcagaaag actgaaggag ccagaaanta tcaatgccag ggaaactgtc ttcgagaccc | 60 |
| aacaggaact gatacacgag ccaaaccagc aatgtcttcc cctgcacagc ctgcagttcc | 120 |
| tgccccactg gccaacttga agattcaaca caccaagatc ttnataaaca atgaatggca | 180 |
| tgattcagtg atggcaagna attacctgtc cttaaccctg caatgaggag gtcatctgac | 240 |
| atgtggaaga agggacaagg cagatgttga caagctgtga agccgcaaga caggctttcc | 300 |

<210> SEQ ID NO 327
<211> LENGTH: 350
<212> TYPE: DNA
<213> ORGANISM: Rattus norvegicus

<400> SEQUENCE: 327

| attggtgtta acacagatga gtactgttgc accattccta tggtcatggg cactgctcaa | 60 |

| | |
|---|---|
| ataataaagg agctatccag agagaacctg caggctgttc taaaggatac agcagcacaa | 120 |
| atgatgcttc ctcctgagtg tggtgacctg ctcatggaag agtacatggg gaacactgat | 180 |
| gattcccaga ccctacaaat acagtacaca gagatgatgg gagacttcct gtttgtgatc | 240 |
| cctgcactcc aagtagcaca ctttcagcgt tcccatgccc ctgtctactt ctatgagttc | 300 |
| caacatgcac ccagctattc aagaatgtca ggccacccca gtgaaggtga | 350 |

<210> SEQ ID NO 328
<211> LENGTH: 258
<212> TYPE: DNA
<213> ORGANISM: Rattus norvegicus
<220> FEATURE:
<221> NAME/KEY: unsure
<222> LOCATION: (1)..(258)
<223> OTHER INFORMATION: unsure at all n locations

<400> SEQUENCE: 328

| | |
|---|---|
| agantgtnga gcgagcnaag naatatgtcc ttgganancc tctgnnccaa gnaatanatc | 60 |
| agggccctca gattnacaag gagcaacatg ataaaatcct tgatctcant gagagtggga | 120 |
| agaangaagg agccaanctn gagtgtggtn taggacgcng ggggnacaaa ggcttcnttg | 180 |
| tccancccnn agtcatctcc aatgtgacng atgagatgng cattnccnaa gaggngatat | 240 |
| ttggancagn gcaacaaa | 258 |

<210> SEQ ID NO 329
<211> LENGTH: 245
<212> TYPE: DNA
<213> ORGANISM: Rattus norvegicus
<220> FEATURE:
<221> NAME/KEY: unsure
<222> LOCATION: (1)..(245)
<223> OTHER INFORMATION: unsure at all n locations

<400> SEQUENCE: 329

| | |
|---|---|
| gaaatgatgt ggccaggttc atcaactggt tggaggnaga atttaactac cccctagaca | 60 |
| atgtccacct cttagggtac agtcttggag cccatgctgc tggcgtggca ggaagtctga | 120 |
| ccaacagaag gtcaatagaa ttactggctt ggatccagct gggcctaact ttgagtatgc | 180 |
| agaagcccct agtcgccttt ctcctgatga tgcggatttc gtagatgtct tacacacatt | 240 |
| tacca | 245 |

<210> SEQ ID NO 330
<211> LENGTH: 191
<212> TYPE: DNA
<213> ORGANISM: Rattus norvegicus

<400> SEQUENCE: 330

| | |
|---|---|
| gattatttgt agccaccatg agagactttg ggataggaaa gcagagtgtg gaggatcaga | 60 |
| taaaggagga ggccaaatgt ttagtggagg aactgaagaa tcatcaggga gtctccctgg | 120 |
| acccaacgtt cctcttccag tgcgtcacag gcaacataat ctgctccatt gtctttggag | 180 |
| agcgctttga c | 191 |

<210> SEQ ID NO 331
<211> LENGTH: 265
<212> TYPE: DNA
<213> ORGANISM: Rattus norvegicus

<400> SEQUENCE: 331

| | |
|---|---|
| aggaagccct gcagagcatc agaggcccag ctagagggac aacacagagg agtaatttgc | 60 |

```
tgacagacct gcagggatgg acctgctttc agctctcaca ctggaaacct gggtcctcct      120
ggcagtcgtc ctggtgctcc tctacggatt tgggacccgc acacatggac ttttcaagaa      180 acagggggatt cctgggccca aacctctgcc ttttttttggc actgtgctga attactatat     240
gggtttatgg aaattcgatg tggag                                             265

<210> SEQ ID NO 332
<211> LENGTH: 296
<212> TYPE: DNA
<213> ORGANISM: Rattus norvegicus

<400> SEQUENCE: 332
gactgctgga accaacgtcc tctcttaccc tccaccttct tctgtcacct ctaccacggt       60
caccatgtcg caagcccggc ctgccactgt gctgggtgcc atggagatgg gtcgccgcat      120
ggatgtgacc tccagctccg cgtcggtgcg cgccttcctg cagcgcggcc acacggagat      180
agacaccgcc ttcgtgtatg cgaacggtca gtctgagacc atcctaggag acctggggct      240
cggactgggc cgcagcggct gcaaagtaaa aattgccacc aaggctgccc caatgt         296

<210> SEQ ID NO 333
<211> LENGTH: 214
<212> TYPE: DNA
<213> ORGANISM: Rattus norvegicus

<400> SEQUENCE: 333
gagatgttcc ctgtcatcga acagtatgga gacatttggg taaaatactt gaggcaagag       60
aaaggcaaac ctgtccctgt gaaagaagtg tttggtgcct acagcatgga tgtgatcacc      120
agcacatcat ttggagtgaa tgttgattcc ctcaacaacc cgaaggatcc ttttgtggag      180
aaagccaaga agctcttaag aattgatttt tttg                                  214

<210> SEQ ID NO 334
<211> LENGTH: 183
<212> TYPE: DNA
<213> ORGANISM: Rattus norvegicus

<400> SEQUENCE: 334
ggcagcattg atcctatgt atatctgccc tttggaaatg gacccaggaa ctgcattggc        60
atgaggtttg ctctcatgaa tatgaaactc gctctcacta agttctgcaa aaacttctcc      120
ttccagcctt gtaaggaaac acagatacct ctgaaattaa gcagacaagg acttcttcaa      180
cca                                                                    183

<210> SEQ ID NO 335
<211> LENGTH: 174
<212> TYPE: DNA
<213> ORGANISM: Rattus norvegicus

<400> SEQUENCE: 335
attggcacca aggagggaat cctgcagtac tgccaagagg tctaccctga actgcagatc       60
acaaacgtgg tggaagccaa ccagccagtg accatccaga actggtgcaa gcggggccgc      120
aagcagtgca agacgcacac ccacatcgtg attcttaccg gtgcctagtt ggtg            174

<210> SEQ ID NO 336
<211> LENGTH: 241
<212> TYPE: DNA
<213> ORGANISM: Rattus norvegicus
```

```
<400> SEQUENCE: 336
atttgggcat ggggaaaagg aacattgagg atcgtgttca agaggaagca cggtgccttg      60
tggaggaact gaggaaaacc aatggctcac cctgtgaccc cacgtttatc ctgggctgtg     120
ctccttgcaa tgtcatctgc tccattattt tccagaatcg ttttgattat aaagatcagg     180
attttcttaa cttgatggaa aaactcaatg agaacatgaa gattttgagc agtccctgga     240
c                                                                    241

<210> SEQ ID NO 337
<211> LENGTH: 289
<212> TYPE: DNA
<213> ORGANISM: Rattus norvegicus
<220> FEATURE:
<221> NAME/KEY: unsure
<222> LOCATION: (1)..(289)
<223> OTHER INFORMATION: unsure at all n locations

<400> SEQUENCE: 337
atgaaggtct ttgtgcccac tggcttttca gccttccctt ccgagctact gcatgcccca      60
gaaaaagtgg gtgaaggtca agtacccaa actcatctcc tattcctaca tggaacgtgg     120
gggccacttt gctgcctttg aagagcccaa gcttctggcc aggacatccg caagttcgtg     180
tccctggctg agctgnagta ntnacggntt annaaantgt ggctttagna naanccgtgt     240
tccccanagn aannttgggn aacccccctn gggaaaaant tntcccccc                 289

<210> SEQ ID NO 338
<211> LENGTH: 243
<212> TYPE: DNA
<213> ORGANISM: Rattus norvegicus
<220> FEATURE:
<221> NAME/KEY: unsure
<222> LOCATION: (1)..(243)
<223> OTHER INFORMATION: unsure at all n locations

<400> SEQUENCE: 338
tgggcagaaa ggaagccctg cagagcatca gangcccagc tagagggaca acacagagga      60
gtaatttgct gacagacctg cagggatgga cctgctttca gctctcacac tggaaacctg     120
ggtcctcctg gcagtcgtcc tggtgctcct ctacggattt gggacccgca catggact      180 tttcaagaaa caggggattc ctgggcccaa acctctgcct ttttttggca ctgtgctgaa     240
tta                                                                  243

<210> SEQ ID NO 339
<211> LENGTH: 289
<212> TYPE: DNA
<213> ORGANISM: Rattus norvegicus
<220> FEATURE:
<221> NAME/KEY: unsure
<222> LOCATION: (1)..(289)
<223> OTHER INFORMATION: unsure at all n locations

<400> SEQUENCE: 339
gcagaaagga agccctgcag agcatcagag gcccagncag agggacaaca cagaggagta      60
atttgctgaa cagacctgca gggatggacc tgctttcagc tctcacactg gaaacctggg    120
tcctcctggc agtcgtcctg gtgctcctct acggatttgg gacccgcaca catggacttt    180
ncaagaaaca ggggattcct gggcccaaac ctctgccttt ntttggcatg tgctgaattn    240
ctatatgggt ttatggaaat tcgatgtgga gtgccataaa aagtatgga                289
```

```
<210> SEQ ID NO 340
<211> LENGTH: 289
<212> TYPE: DNA
<213> ORGANISM: Rattus norvegicus

<400> SEQUENCE: 340
atttaaggtg atctatctca tcagaaatcc cagagatgtt cttgtttctg gttattattt      60
ctggggtaag acaactcttg cgaagaagcc agactcactg ggaacgtatg ttgaatggtt     120
cctcaaagga aatgttccgt atggatcatg gtttgagcac atccgtgcct ggctgtctat     180
gcgagaatta gacaacttct tgttactgta ctatgaagac atgaaaaagg atacaatggg     240
aaccataaag aagatatgtg acttcctggg gaaaaaatta gagccagat                289

<210> SEQ ID NO 341
<211> LENGTH: 278
<212> TYPE: DNA
<213> ORGANISM: Rattus norvegicus

<400> SEQUENCE: 341
atggaatacc tggatatggt gttgaatgaa accctcagat tgtatccaat tggtaataga      60
cttgagagag tctgtaaaaa agatgttgaa atcaatggtg tgtttatgcc caaagggtca     120
gtggtcatga ttccatctta tgctcttcac cgtgatccac agcactggcc agagcctgag     180
gaatttcgcc cagaaaggtt cagcaaggag aacaagggca gcattgatcc ttatgtatat     240
ctgccctttg gaaatggacc caggaactgc attggcat                            278

<210> SEQ ID NO 342
<211> LENGTH: 312
<212> TYPE: DNA
<213> ORGANISM: Rattus norvegicus
<220> FEATURE:
<221> NAME/KEY: unsure
<222> LOCATION: (1)..(312)
<223> OTHER INFORMATION: unsure at all n locations

<400> SEQUENCE: 342
cggtcggtac cggagagcgc aggttgtatc accaacatgg gggactctca cgaagacacc      60
agtgccacca tgcctgangc cgtggctgaa gaagtgtctc tattcagcac gacggacatg     120
gttctgtttt ctctcatcgt gggggtcctg acctactggt tcatctttag aaagaagaaa     180
gaagagatac cggagttcag caagatccaa acaacggccc cacccgtcaa agagagcagc     240
ttcgtggaaa agatgaagaa aacgggaagg aacattatcg tattctatgg ctcccagacg     300
ggaaccgctg ag                                                        312

<210> SEQ ID NO 343
<211> LENGTH: 287
<212> TYPE: DNA
<213> ORGANISM: Rattus norvegicus
<220> FEATURE:
<221> NAME/KEY: unsure
<222> LOCATION: (1)..(287)
<223> OTHER INFORMATION: unsure at all n locations

<400> SEQUENCE: 343
agctagtgag gcctctgggg ctgcgaccta cctcgcagag gggtttgcac taaggcgctg      60
ggcgccgtga ctccgggcgc tgtggaccat ggctccgccc caggcgccca acagggaccg     120
tgcangccag gaggatgagg accgttggga cacggggggg accgcaaggc ccggaagccc     180
ctggtggaga agaagcgacg cgcgcggatc aacgagagtc ttcaggagtt gcggctgctg     240
```

```
ctagcgggca ccgngtgcag gccaagctag agaacgccga ggtgctg                         287
```

```
<210> SEQ ID NO 344
<211> LENGTH: 232
<212> TYPE: DNA
<213> ORGANISM: Rattus norvegicus

<400> SEQUENCE: 344
cattcttgac cagtaccaca tttttgagcc caagtgcctg gacgccttcc caaacctgaa           60
ggacttcctg gcccgctttg agggcctgaa gaagatctct gcctacatga attgcagccg         120
ctacctctca acacctatat tttcgaagtt ggcccaatgg agtaacaagt aggcccttgc         180
tacactggca ctcacagaga ggacctgtcc acattggatc ctgcaggcac cc                 232

<210> SEQ ID NO 345
<211> LENGTH: 223
<212> TYPE: DNA
<213> ORGANISM: Rattus norvegicus

<400> SEQUENCE: 345
tgtctgcaag cacaacattg aatcagtaac agttgtcagg gttggtgact gcccatggaa          60
tggatctttt attcatgagc aattcagccc caaaatgaat ttggaaaact tttgcctgaa        120
gtacttattg aaatacaatc aagagacctg ctgaatattt tgatgcgttc tcaaaagtgt        180
atggtcctgt atttactctt tactttggca tgaagcccac tgt                           223

<210> SEQ ID NO 346
<211> LENGTH: 278
<212> TYPE: DNA
<213> ORGANISM: Rattus norvegicus
<220> FEATURE:
<221> NAME/KEY: unsure
<222> LOCATION: (1)..(278)
<223> OTHER INFORMATION: unsure at all n locations

<400> SEQUENCE: 346
atggagtaac aagtaggccc ttgctacact ggcactcaca gagaggacct gtccacattg          60
gatcctgcag gcaccctggc cttctgcact gtggttctct ctccttcctg ctcccttctc        120
cagctttgtc agccccatct cctcaacctc accccagtca tgcccacata gtcttcattc        180
tccccacttt ctttcatagt ggnccccttc tttattgaca ccttaacaca acctcacagt        240
ccttttctgt gattgaggtc tgccctgaac tcagtctc                                 278

<210> SEQ ID NO 347
<211> LENGTH: 295
<212> TYPE: DNA
<213> ORGANISM: Rattus norvegicus
<220> FEATURE:
<221> NAME/KEY: unsure
<222> LOCATION: (1)..(295)
<223> OTHER INFORMATION: unsure at all n locations

<400> SEQUENCE: 347
gcgggccgtg ggtgatctgg tcggtaccgg agagcgcagg ttgtatcacc aacatggggg          60
actctcacga agacaccagt gccaccatgc ctgaggccgt ggctgaagaa gtgtctctat        120
tcagcacgac ggacatggtt ctgttttctc tcatcgtggg ggtcctgacc tactggttca        180 tcttttagaaa gaagaaagaa gagataccgg agttcagcaa gatccaaaca acggccccac        240
ccgtcaaaga gagcagcttc gtggaaaaga tgaagaaaac gggaangaac ttatc             295
```

<210> SEQ ID NO 348
<211> LENGTH: 230
<212> TYPE: DNA
<213> ORGANISM: Rattus norvegicus

<400> SEQUENCE: 348
tcagtgacag aacaggaact taacctttgg tgattctcat gggactacct ccatccacat      60
ctggttgtct ctgttaattt cttttgatag taaccttgtc tctgtaattt gatcaagaat     120
ttttcatgaa aatgtgaact attgtgacaa ctttaattgt agatttggta tcagatgttt     180
tagatgcatt attctacact aaatgttaca tggaaaaaat gtgaataaac                230

<210> SEQ ID NO 349
<211> LENGTH: 282
<212> TYPE: DNA
<213> ORGANISM: Rattus norvegicus
<220> FEATURE:
<221> NAME/KEY: unsure
<222> LOCATION: (1)..(282)
<223> OTHER INFORMATION: unsure at all n locations

<400> SEQUENCE: 349
cccggctcta tattaggcca acagcggccc tagccgaggc tgttcgtgaa gaagggcact      60
ggtcggttta gcgtcctccg ctcgngtgcc caccgccgtc tcgtcgagag cccgcgcagg     120
acccgggaca ctttgcagac atggagactg tcgttcgcag atgcccattc ttatcccgag     180
tccctcaggc ntttctgcag aaggcaggga atctctgct gttctatgct caaaactgcc      240
ccaagatgat ggaagtcggg gccaagccgg ctcctcggac cg                        282

<210> SEQ ID NO 350
<211> LENGTH: 280
<212> TYPE: DNA
<213> ORGANISM: Rattus norvegicus
<220> FEATURE:
<221> NAME/KEY: unsure
<222> LOCATION: (1)..(280)
<223> OTHER INFORMATION: unsure at all n locations

<400> SEQUENCE: 350
ccgaggcagt tcacccgagg ccgatctccg aggtctgcca gcggctactt cccacagcct      60
ccgccatggg tctggagctt ctacctggac ctgatgtccc agcnntgccg tgccgtctac     120
atcttcgcca agaagaacgg catcccttc cagctgcgta ccatcgagct gcttaaaggt      180
cagcattaca ctgatgcctt tgcccaggtg naccctttga ggaaggtgcc ggctttgaag     240
gatggggact tcgtcttggc agagagtgtg ccatcttgct                           280

<210> SEQ ID NO 351
<211> LENGTH: 309
<212> TYPE: DNA
<213> ORGANISM: Rattus norvegicus
<220> FEATURE:
<221> NAME/KEY: unsure
<222> LOCATION: (1)..(309)
<223> OTHER INFORMATION: unsure at all n locations

<400> SEQUENCE: 351
tcttagccaa catgatcagt gaacccagaa tcagttacgg caacgatgct ctcatgcctt      60
ctttgactga nacgaagacc actgtggagc tccttcccgt gaatggcgaa ttcagcctgg     120
atgatctcca accgtggcat ccttttgggg tggactctgt gccagccaat acagaaaatg     180
aagggtctgg gttgacaaac atcaagacag aagagatctc agaagtgaag atggatgcgg     240

```
agttcggaca tgattcangc ttcgaatccg ccatcaaaaa ctggtggtct tgcagaagng    300
tgggtcaaa                                                           309
```

<210> SEQ ID NO 352
<211> LENGTH: 228
<212> TYPE: DNA
<213> ORGANISM: Rattus norvegicus

<400> SEQUENCE: 352

```
gctggctgca aaatcttcga gagccgaccc aaactggctg cgtggcgtca gcgggtggaa    60
gccgcagtgg gggagagcct cttccaggag gcccatgaag tcgtcctgaa ggccaaagat   120
atgcctccct tgatggaccc gaccttgaag gagaaactga agctctctgt tcaatgcctg   180
ctgcactgag ggaacagcct gaagtcaagg gaaacttggt gtgtgcgt                228
```

<210> SEQ ID NO 353
<211> LENGTH: 298
<212> TYPE: DNA
<213> ORGANISM: Rattus norvegicus
<220> FEATURE:
<221> NAME/KEY: unsure
<222> LOCATION: (1)..(298)
<223> OTHER INFORMATION: unsure at all n locations

<400> SEQUENCE: 353

```
caggatcatg gatactagtg tccttctcct ccttgctgtc ctcctcagct tcttgctatt    60
cctggtcaga ggccatgcaa aagttcatgg tcatcttcca ccaggacccc gtcccttacc   120
cctcttggga aacctcttgc agatggacag aggaggcttt cgtaagtctt tcattcagct   180
tcaagaaaaa cacggagatg tgttcacagt atactttgga cctaggcctg tggtcatgct   240
gtgtgggaca cagaccataa gggaggctct ggtggacatg ctgaggnttc tctggcgg     298
```

<210> SEQ ID NO 354
<211> LENGTH: 326
<212> TYPE: DNA
<213> ORGANISM: Rattus norvegicus
<220> FEATURE:
<221> NAME/KEY: unsure
<222> LOCATION: (1)..(326)
<223> OTHER INFORMATION: unsure at all n locations

<400> SEQUENCE: 354

```
gacaaaatcc cagaataagg aaactctgaa ccaggagtca tggaagtcaa acccaagctc    60
tactactttc aaggcagggg aaggatggag tcgatccgct ggctgctggc tacagctgga   120
gtggagtttg aagaagaatt tcttgagacg agagaacaat atgagaagtt gcaaaaggat   180
ggatgcctgc tttttggcca agtcccattg gtggaaatag acgggatgct actgacacag   240
accagagcca tcctcagcta cctggccgcc aagtacaact tgtatgggaa ggacctgaan   300
gagagagtca ggattgacat gtatgc                                       326
```

<210> SEQ ID NO 355
<211> LENGTH: 274
<212> TYPE: DNA
<213> ORGANISM: Rattus norvegicus
<220> FEATURE:
<221> NAME/KEY: unsure
<222> LOCATION: (1)..(274)
<223> OTHER INFORMATION: unsure at all n locations

<400> SEQUENCE: 355

```
tccttctcct ccttgctgtc ctcctcagct tcttgctatt cctggtcaga ggccatgcaa    60
```

| | |
|---|---|
| aagttcatgg tcatcttcca ccaggacccc gtcccntacc cctcttggga aaacnctttg | 120 |
| aagaatggac agaggaggct ttgtaagtct ttcattnagc ttcaagaaaa acacggagat | 180 |
| gtgttcacaa gtatacttgg aactaggcct gtggtcatgc tgtgtgggac acagaccata | 240 |
| agggaggctc tggtggacat gctgangctt ctct | 274 |

<210> SEQ ID NO 356
<211> LENGTH: 148
<212> TYPE: DNA
<213> ORGANISM: Rattus norvegicus
<220> FEATURE:
<221> NAME/KEY: unsure
<222> LOCATION: (1)..(148)
<223> OTHER INFORMATION: unsure at all n locations

<400> SEQUENCE: 356

| | |
|---|---|
| cggcccccact gcctcagaga cctacaggac cgcgggncgt gggtgatctg gtcggtaccg | 60 |
| gagagcgcag gttgtatcac caacatgggg gactctcacg aagacaccag tgccaccatg | 120 |
| cctgaggccg tggctgaaga agtgtctc | 148 |

<210> SEQ ID NO 357
<211> LENGTH: 302
<212> TYPE: DNA
<213> ORGANISM: Rattus norvegicus

<400> SEQUENCE: 357

| | |
|---|---|
| ttagatctga ctgaaatgat tatccaattg gtaatatgtc ccccagacca aagagaagcc | 60 |
| aagaccgcct tggcaaaaga caggaccaaa aaccggtact tgcctgcctt tgaaaaggtg | 120 |
| ttgaagagcc atggccaaga ctaccttgta ggtaacaggc tgacccgggt agacatccac | 180 |
| ctgctggaac ttctcctcta tgttgaagag tttgatgcca gccttctgac ctctttccct | 240 |
| ctgctgaagg ccttcaagag cagaatcagc agcctcccca atgtgaagaa gttcctgcag | 300 |
| cc | 302 |

<210> SEQ ID NO 358
<211> LENGTH: 286
<212> TYPE: DNA
<213> ORGANISM: Rattus norvegicus

<400> SEQUENCE: 358

| | |
|---|---|
| cggaagtgaa ccaaggcact gagcggcatc taatgcacct ggagttggac atctcagact | 60 |
| ccaagatcag gtatgaatct ggagatcacg tggctgtgta cccagccaat gactcagccc | 120 |
| tggtcaacca gattggggag atcctgggag ctgacctgga tgtcatcatg tctctaaaca | 180 |
| atctcgatga ggagtcaaac aagaagcatc cgttcccctg ccccaccacc taccgcacgg | 240 |
| ccctcaccta ctacctggac atcactaacc cgccacgcac caatgt | 286 |

<210> SEQ ID NO 359
<211> LENGTH: 320
<212> TYPE: DNA
<213> ORGANISM: Rattus norvegicus

<400> SEQUENCE: 359

| | |
|---|---|
| caagttcctg cagaacaagg ccttcctaac aggaccccat atctccgtgg ctgacttggt | 60 |
| ggccatcaca gaactgatgc atcctgtcag tgctggctgc aaaatcttcg agagccgacc | 120 |
| caaactggct gcgtggcgtc aggggtggaa gccgcagtgg gggagagcct cttccaggag | 180 |

```
gcccatgaag tcgtcctgaa ggccaaagat atgcctccct tgatggaccc gaccttgaag      240
gagaaactga agtctctgtt caatgctgct gcatgaggga acagcctgaa gtcaagggaa      300
acttgtgtgt gcgtgtgtgt                                                  320

<210> SEQ ID NO 360
<211> LENGTH: 288
<212> TYPE: DNA
<213> ORGANISM: Rattus norvegicus
<220> FEATURE:
<221> NAME/KEY: unsure
<222> LOCATION: (1)..(288)
<223> OTHER INFORMATION: unsure at all n locations

<400> SEQUENCE: 360
tngcctctgt ccaccgaggc agttcacccg aggccgatct ccgaggtctg ccagcggcta       60
cttcccacag cctccgccat gggtctggag ntctacctgg actgatgtcc cagccctgcc     120
gtgccgtcta catcttcgcn aagaagaacg gcatcccttc cagctgcgta ccatcgagct     180
gcttaaaggt cagcattaca tgatgcnttg cncaggtgaa cntttgngga aggtgccggc     240
nttgaagcng gagattcgtc ttgccaanna tgtggcancn tgctgtat                  288

<210> SEQ ID NO 361
<211> LENGTH: 272
<212> TYPE: DNA
<213> ORGANISM: Rattus norvegicus

<400> SEQUENCE: 361
gaactctgct caacagcctc tttctctagt tcctgcagac aaaatcccag aataaggaaa      60
ctctgaacca ggagtcatgg aagtcaaacc caagctctac tactttcaag gcaggggaag    120
gatggagtcg atccgctggc tgctggctac agctggagtg gagtttgaag aagaatttct    180
tgagacgaga gaacaatatg agaagttgca aaaggatgga tgcctgcttt ttggccaagt    240
cccattggtg gaaatagacg ggatgctact ga                                  272

<210> SEQ ID NO 362
<211> LENGTH: 286
<212> TYPE: DNA
<213> ORGANISM: Rattus norvegicus
<220> FEATURE:
<221> NAME/KEY: unsure
<222> LOCATION: (1)..(286)
<223> OTHER INFORMATION: unsure at all n locations

<400> SEQUENCE: 362
ggcccatgga gcacacccag gctgtggact atgttaagaa gctgatgacc aagggccgct      60
actcactaga tgtgtggagt aggagctacc accctcccac ccctcgctcc ctgtaatcac    120
ctaacttctg ccgacctcca cctctggtgg ttcctgcctg gcctggacac agggaggccc    180
agggactgac tcctggcctg agtngtgccc tcctgggccc ctaagcagag tccggtccat    240
tgtatcaggc agcccagccc caaggcacat ggcaagaggg attgac                   286

<210> SEQ ID NO 363
<211> LENGTH: 288
<212> TYPE: DNA
<213> ORGANISM: Rattus norvegicus
<220> FEATURE:
<221> NAME/KEY: unsure
<222> LOCATION: (1)..(288)
<223> OTHER INFORMATION: unsure at all n locations

<400> SEQUENCE: 363
```

```
gtaaaagang ccttgattga tcatggggag gagtttgctg aaagaggaag cttcccagta    60
gctgaaaaaa ttaataaaga ccttggaatt gtttttagcc atggaaatag atggaaagaa   120
ataagacgct taccctcacg actctgcgga atttgggcat ggggaaaagg aacattgagg   180
ntcgtgttca anaggcaanc ccggnancct nggggaggac ctgnggaaan ccatggggcn   240
caccgtgnna ccccangtnt atccctgggc tgngcncctt gnannacc               288
```

<210> SEQ ID NO 364
<211> LENGTH: 237
<212> TYPE: DNA
<213> ORGANISM: Rattus norvegicus

<400> SEQUENCE: 364

```
tcacagctaa agtccaggaa gagattgatc gtgtggttgg caaacatcgc agcccttgca    60
tgcaggacag gagccgcatg ccctacacag atgccatgat tcatgaggtc cagaggttca   120
ttgacctcat tcctaccaac ctgccacatg cggtgacctg tgacattaag ttcaggaact   180
acctaatacc caagggaaca acaataaataa catcactctc atcagtgctg catgaca      237
```

<210> SEQ ID NO 365
<211> LENGTH: 304
<212> TYPE: DNA
<213> ORGANISM: Rattus norvegicus

<400> SEQUENCE: 365

```
ggagaatgga gcccatccgg tggctcctgg ctgcagctgg agtagagttt gaagaacaat    60
ttctgaaaac tcgggatgac ctggccaggc taaggaatga tgggagtttg atgttccagc   120
aagtgcccat ggtggagatt gatgggatga agctggtgca gaccagagcc attctcaact   180
acattgccac caaatacaac ctctatggga aggacatgaa ggagagagcc ctcatcgaca   240
tgtatgcaga aggagtggcg gatctggatg aaatagttct ccattaccct tacattcccc   300
ctgg                                                                304
```

<210> SEQ ID NO 366
<211> LENGTH: 218
<212> TYPE: DNA
<213> ORGANISM: Rattus norvegicus
<220> FEATURE:
<221> NAME/KEY: unsure
<222> LOCATION: (1)..(218)
<223> OTHER INFORMATION: unsure at all n locations

<400> SEQUENCE: 366

```
ggcactggtc ggtttagcgt cctccgctcg agtgcccacc gncgtctcgt acgagagccc    60
gcgcaggacc cggcgacact ntgcagacnt ggagactgtc gtttcgcaga tgcccattct   120
tatcccgagt ccctcaggcn tttctgcaga aggcagggaa atctctgctg ttctatgctc   180
aaaactgccc caagatgatg gaatcggggc naanccgg                          218
```

<210> SEQ ID NO 367
<211> LENGTH: 269
<212> TYPE: DNA
<213> ORGANISM: Rattus norvegicus
<220> FEATURE:
<221> NAME/KEY: unsure
<222> LOCATION: (1)..(269)
<223> OTHER INFORMATION: unsure at all n locations

<400> SEQUENCE: 367

-continued

```
ggtcnccatg gatctggtca ctttcctggt acttactctc tcctctctca ttctcctctc    60
actctggaga nagnnccgct aggagaagga agctcnctcc tggccccact cctctcccna   120
ttatcggtaa tttccctccn gatagatgtg aagaacatca gccaatccta accaagtttt   180
caaaaaccta tggccctgtg ttcactctgt atttgggctc acagcccnct gtcatattgc   240
atggatntga agcnataaag gagctctgt                                     269
```

<210> SEQ ID NO 368
<211> LENGTH: 270
<212> TYPE: DNA
<213> ORGANISM: Rattus norvegicus
<220> FEATURE:
<221> NAME/KEY: unsure
<222> LOCATION: (1)..(270)
<223> OTHER INFORMATION: unsure at all n locations

<400> SEQUENCE: 368

```
gagaccgcca gttccgtctc tactcttttg tgaggactgc agccaacacc gctgacaatg    60
cagatctttg tgaaaacctt aactggtaag accatcaccc tggaggtcga gcccagtgac   120
accattgaaa atgtcaaggc aaagatccag gacaaggagg gcatcccccc tgaccagcag   180
aggctgatct ttgcaggcaa gcagctggaa gatggccgca ccctgttcag actacaacat   240
ccagaaggag tccaccntgc acctggtcct                                    270
```

<210> SEQ ID NO 369
<211> LENGTH: 238
<212> TYPE: DNA
<213> ORGANISM: Rattus norvegicus

<400> SEQUENCE: 369

```
ggaagcaatg attctaggtg tgtttctggg gcttttctca acatgtctgc ttctcctttc    60
actgtggaag cagaattttc agagaagaaa ccttcctcct ggccccacac ctcttcctat   120
cattggaaat attcttcaga tagatcttaa ggacatcagc aaatctctga ggaattttc    180 aaaagtctat ggccctgtgt tcaccctgta ctttggcagg aagcctgctg tggtgtta    238
```

<210> SEQ ID NO 370
<211> LENGTH: 260
<212> TYPE: DNA
<213> ORGANISM: Rattus norvegicus
<220> FEATURE:
<221> NAME/KEY: unsure
<222> LOCATION: (1)..(260)
<223> OTHER INFORMATION: unsure at all n locations

<400> SEQUENCE: 370

```
aaaggaccag ttctgtattg gtggttagta ggctacgttg tcatggtggc ctctggcaac    60
ccaggtacct gaaaaccagt ttcagggaca gcagtggaga acatactcta ggcaaacata   120
ctggcctgtt tccattataa caagatacct aaggccaact actttnttta ccaagagaag   180
aggtttgtta cagcacaaga tgaggtggcc ccgtcgttag cccttggagg gccatgtgga   240
aaataacacg tggtgaggga                                               260
```

<210> SEQ ID NO 371
<211> LENGTH: 283
<212> TYPE: DNA
<213> ORGANISM: Rattus norvegicus
<220> FEATURE:
<221> NAME/KEY: unsure
<222> LOCATION: (1)..(283)
<223> OTHER INFORMATION: unsure at all n locations

<400> SEQUENCE: 371

```
cgcgcgtccc ttaccccgtt ggctgcggcg atgcgtacga tgagctggat ggcctcggtc    60
atgtagaagc gaccgtccnc gcccacaacc agcgtggcct cctgcctcaa cgccggctcc   120
acggtggaga cgatgctttg gatgaaattc tccgcatagt tagcgttgcc ctggaacacc   180
tncactcgct tccgcaaccc gctggtgccc ggcttctgat ccggntatgc ctgcgtcttc   240
actgtcacga tcttcaccat ggtggccggg gctgcgnggc gac                     283
```

<210> SEQ ID NO 372
<211> LENGTH: 273
<212> TYPE: DNA
<213> ORGANISM: Rattus norvegicus
<220> FEATURE:
<221> NAME/KEY: unsure
<222> LOCATION: (1)..(273)
<223> OTHER INFORMATION: unsure at all n locations

<400> SEQUENCE: 372

```
gaaaagttca tgcctatcgt ttacactncc acngngngtc ntgcatgnca gcaatacagt    60
tggcattccg gaagccaaga ngcctcttta tcagnatcca cganaaaggg natattgctt   120
cagttctgaa cgcatggcca gaagatgttg tnanngctat tgtggtgact gatgggatag   180
nggatcctnc ggntgggcg acctttgtnn tanngggtg gcatncctg gggtgtaaag    240
ggtccctgna aacaggttng gggggtngat ccc                               273
```

<210> SEQ ID NO 373
<211> LENGTH: 301
<212> TYPE: DNA
<213> ORGANISM: Rattus norvegicus

<400> SEQUENCE: 373

```
tacggaagta gttcccgctg cttatgccat ggtcctggaa ctgtacctgg atctgctgtc    60
gcagccctgt ccgcgctatt tatatcttcg ccaagaagaa caatatcccg ttccagatgc   120
atactgtgga gctgcgcaag ggtgagcacc tcagcgatgc cttttgcccag gtgaaccca   180
tgaagaaggt accagccatg aaggatggtg gcttcacctt gtgtgagagt gtggccatcc   240
tgctctacct ggcgcacaag tataaggttc ctgaccactg gtaccccaa gacctgcagg   300
c                                                                   301
```

<210> SEQ ID NO 374
<211> LENGTH: 309
<212> TYPE: DNA
<213> ORGANISM: Rattus norvegicus

<400> SEQUENCE: 374

```
gggtctccat ggatctggtc actttcctgg tacttactct ctcctctctc attctcctct    60
cactctggag acagagctct aggagaagga agctccctcc tggccccact cctctcccaa   120
ttattggtaa tttcctccag atagatgtga agaacatcag ccaatcctta accaagtttt   180
caaaaaccta tggccctgtg ttcactctgt atttgggctc acagcccact gtcatattgc   240
atggatatga agcaataaag gaagctctga ttgataacgg ggagaagttt tctggtagag   300
gaagctatc                                                          309
```

<210> SEQ ID NO 375
<211> LENGTH: 298
<212> TYPE: DNA

<213> ORGANISM: Rattus norvegicus
<220> FEATURE:
<221> NAME/KEY: unsure
<222> LOCATION: (1)..(298)
<223> OTHER INFORMATION: unsure at all n locations

<400> SEQUENCE: 375

| | |
|---|---|
| gtacccacat gtcacagcta aagtccagga agagattgac cgtgtgattg gcagacatcg | 60 |
| cagcccctgc atgcaggata gaaaacacat gccctacaca gatgccatga ttcatgaggt | 120 |
| acagagattc attaactttg tcccgaccaa cctgccccat gcagtgacct gtgacattaa | 180 |
| attcaggaac tacctcatcc cgaaggaaca aaagtgttaa catcactgac atcagtgctg | 240 |
| catgacagca aggagttccc naacccagag atgtttgacc ctggccactt tctagatg | 298 |

<210> SEQ ID NO 376
<211> LENGTH: 234
<212> TYPE: DNA
<213> ORGANISM: Rattus norvegicus

<400> SEQUENCE: 376

| | |
|---|---|
| cagacatcgc agcccctgca tgcaggatag aaaacacatg ccctacacag atgccatgat | 60 |
| tcatgaggga acaaaagtgt taacatcact gacatcagtg ctgcatgaca gcaaggagtt | 120 |
| ccccaaccca gagatgtttg accctggcca ctttctagat gagaatggaa actttaagaa | 180 |
| aagtgactac ttttttgcctt tctcagcagg aaaacgagct tgtgttggag aggg | 234 |

<210> SEQ ID NO 377
<211> LENGTH: 267
<212> TYPE: DNA
<213> ORGANISM: Rattus norvegicus

<400> SEQUENCE: 377

| | |
|---|---|
| gtcctgacca ggctacgatc tggtacggcg gatgtctatt gtctatgcac taggcgcctg | 60 |
| gtcggtgctg ggctcggcga ttttccttac acgaaaaccg aagatgtcag actatgggga | 120 |
| aaatgaagag gatgactcaa gcaatgaaat gccttttttct acaagtgaag actctgattt | 180 |
| agcgatggaa agggctgagc ctattaaagg gtttttatacg aagacaattg taaagtattc | 240 |
| agaaaattct gttccattac tcagagg | 267 |

<210> SEQ ID NO 378
<211> LENGTH: 249
<212> TYPE: DNA
<213> ORGANISM: Rattus norvegicus
<220> FEATURE:
<221> NAME/KEY: unsure
<222> LOCATION: (1)..(249)
<223> OTHER INFORMATION: unsure at all n locations

<400> SEQUENCE: 378

| | |
|---|---|
| aatccggnag aggatccacc tgagacctga ggncgcctta ttcttctttg tcaacaacac | 60 |
| tatccctccc accagtgcta ccatgggaca gctgtatgag acaaccatg aggaagacta | 120 |
| ttttctgtat gtggcctaca gtgatgaaag tgtctacggg aaatgaggca gaagcccagc | 180 |
| agatgggagc gcctggactt gggggtaggg gaggggtgcg tgtgggactt ggggaaccag | 240 |
| agggagggc | 249 |

<210> SEQ ID NO 379
<211> LENGTH: 292
<212> TYPE: DNA
<213> ORGANISM: Rattus norvegicus

```
<400> SEQUENCE: 379
gaagggagct cagcacgttc agccctgcaa ggggcagtac acaaaattga gagtaaagct      60
cgaagagaga cttgtttaaa gaaaacggca atggatttga tcccaaactt ttccatggaa     120
acctggctgc tcctggttat cagcctggtg ctcctctacc tatatggaac tcattcacat    180 ggaatttta aaaagttggg aattcctggg cccaaacctt tgcctttctt ggggacgatt     240
ctgcttacag gaagggctct gggaattgac aaatactgcc ataaaaaata tg            292

<210> SEQ ID NO 380
<211> LENGTH: 168
<212> TYPE: DNA
<213> ORGANISM: Rattus norvegicus

<400> SEQUENCE: 380
ctagcccgta tggagttatt tttattcctg accacgattt tacaaaactt taagctgaaa      60
tctgtacttc acccaaagga tatcgataca actccagttt tcaatggatt tgcctctctg     120
ccaccatttt atgagctgtg cttcattcct ctctaaagag atcaaatt                  168

<210> SEQ ID NO 381
<211> LENGTH: 298
<212> TYPE: DNA
<213> ORGANISM: Rattus norvegicus
<220> FEATURE:
<221> NAME/KEY: unsure
<222> LOCATION: (1)..(298)
<223> OTHER INFORMATION: unsure at all n locations

<400> SEQUENCE: 381
accagtttct ggttccactc gcagagaagc agagaagcgg agnaagcggc gcgttccaga      60
acctncgggc aagaccagcc tctcccagag catccccacc gcgaaggcan accttctcca     120
gagcataccc cagcggagcg naccttccc cagagcatcc ccgccgccaa gcgcaacctt      180
ccagaagcag agagcggcga catggccaag aaaacagcga tcggcatcga cctgggcacc     240
acctactcgt gcgtgggcgt gttccagcac ggcaaggtgg agatcatcgc caacgacc       298

<210> SEQ ID NO 382
<211> LENGTH: 297
<212> TYPE: DNA
<213> ORGANISM: Rattus norvegicus
<220> FEATURE:
<221> NAME/KEY: unsure
<222> LOCATION: (1)..(297)
<223> OTHER INFORMATION: unsure at all n locations

<400> SEQUENCE: 382
ananaataga agaacaccag gaatcattgg atgttacaaa ccctcgtgat tttgttgatt      60
attacctgat taaacaaaaa caggcaaaca acatcgaaca atcagaatat tcacatgaaa     120
atctgacatg cagtatcatg gatctcattg gtgcagggac agagacaatg agcacaacat     180
tgagatatgc tctcctgctt ctgatgaagt acccacatgt cacagctaaa gtccaggaag     240
agattgaccg tgtgattggc agacatcgca gcccctgcat gcaggataga aaacaca       297

<210> SEQ ID NO 383
<211> LENGTH: 234
<212> TYPE: DNA
<213> ORGANISM: Rattus norvegicus

<400> SEQUENCE: 383
```

```
aacgcagccg actctgcagc attgccatgt caggaatgat attgggaatc tttgctgtgc      60
tccttgtggg cggcatcatt agtgaagccc tcgggtggcc ctttgtcttt tatatctttg     120
gaagtattgg tgtggtctgc tgccttctct ggctcattct ggtttatgat gaccctgtct     180
ctcacccatg gataagtagc ccagaaaagg agtatatttt atcctccctg gacc            234
```

<210> SEQ ID NO 384
<211> LENGTH: 299
<212> TYPE: DNA
<213> ORGANISM: Rattus norvegicus
<220> FEATURE:
<221> NAME/KEY: unsure
<222> LOCATION: (1)..(299)
<223> OTHER INFORMATION: unsure at all n locations

<400> SEQUENCE: 384

```
agctgccatc ttgcgtcccc gcgtgtgtgc gccttatctc agctggtctg cccgagacnc      60
tctgagcgtg aaccttagtc ccccgcgcgg ccccatttcc actccgacaa gatgaaagaa     120
acgatcatga accaggaaaa actcgccaaa ctgcaggcac aagtgcgcat tggtgggaaa     180
ggaactgctc gtagaaagaa gaaggtggtt cacagaacag ccacagcaga cgataaaaaa     240
ctgcagttct ccttaaagaa gttaggggta acaatatct ctgtattgaa gaggtgaac       299
```

<210> SEQ ID NO 385
<211> LENGTH: 291
<212> TYPE: DNA
<213> ORGANISM: Rattus norvegicus

<400> SEQUENCE: 385

```
ctgacgttgt ctatagaaca gtggccaacc tttctggatg tgagcaggtg gactccaagg      60
ctctggtgaa ctgtctacga ggcaagagcg aggaagagat tatgtctatt aacaaggcct     120
tcaggatcat ctctggcata gtggatggta tcttccttcc cagacatccc aaggagctgt     180
tggcctctgc tgactttcac cccattccca gcattattgg tgtcaacaat gatgagtatg     240
gctggatcat tccctcgagc atgaccacca ctgactccaa gaagaaaatg g              291
```

<210> SEQ ID NO 386
<211> LENGTH: 304
<212> TYPE: DNA
<213> ORGANISM: Rattus norvegicus

<400> SEQUENCE: 386

```
actgagtgga cctgtgaaga atccaaattc caaacaattt tcaacatgga ttcccgtgaa      60
ttccggagaa gagggaagga gatggtggat tatatagctg actatctgga cggcattgag     120
ggacgtccag tgtaccctga cgtggagcct ggctaccttc gggccctgat ccccaccact     180 gcccccccagg agccagaaac atatgaggac ataatcagag acattgaaaa gataatcatg     240
ccagggtcac acactggcac agcccctact tcttcgctta cttccccagg ccagctccta     300
ccca                                                                    304
```

<210> SEQ ID NO 387
<211> LENGTH: 264
<212> TYPE: DNA
<213> ORGANISM: Rattus norvegicus
<220> FEATURE:
<221> NAME/KEY: unsure
<222> LOCATION: (1)..(264)
<223> OTHER INFORMATION: unsure at all n locations

<400> SEQUENCE: 387

-continued

| | |
|---|---|
| gngcggagga agccgactgt tccggatctc tgcatagcag ggcccaacct ttgctccana | 60 |
| gatcatggct gccgaggatg tggtggcgac tggngncgac cccagcgagc tggagggcgg | 120 |
| cgggctgctt caanagatnt tcacgncgcn tctcaacctg ctgctccttg gccatgcatc | 180 |
| ttcctgctct acaagatcga tcgcngggac cagcccggtg ccaatgggga caacnactcc | 240 |
| gacgagnngn ccncgctgnc ncng | 264 |

<210> SEQ ID NO 388
<211> LENGTH: 267
<212> TYPE: DNA
<213> ORGANISM: Rattus norvegicus
<220> FEATURE:
<221> NAME/KEY: unsure
<222> LOCATION: (1)..(267)
<223> OTHER INFORMATION: unsure at all n locations

<400> SEQUENCE: 388

| | |
|---|---|
| cggaacagtc gaggctagat tgacacagct gtccgttcag accccagcac catgcccatg | 60 |
| acactgggtt actgggganat ccgtgggggct agcgcatgcc atcgcctgc tcctggaata | 120 |
| cacagactcg agctatgagg agaagagata caccatggga gacgctcccg actttgacag | 180 |
| aagccagtgg ctgaatgaga agttcaaact gggcctggac ttccccaatc tgccctactt | 240 |
| aattgatgga tcacacaaga cacccag | 267 |

<210> SEQ ID NO 389
<211> LENGTH: 307
<212> TYPE: DNA
<213> ORGANISM: Rattus norvegicus

<400> SEQUENCE: 389

| | |
|---|---|
| gtgccctcac gcagcttaat gtggccttt cccgggagca ggcccacaag gtctatgtcc | 60 |
| agcaccttct gaagagagac agggaacacc tgtggaagct gatccacgag ggcggtgccc | 120 |
| acatctatgt gtgcggggat gctcgaaata tggccaaaga tgtgcaaaac acattctatg | 180 |
| acattgtggc tgagttcggg cccatggagc acacccaggc tgtggactat gttaagaagc | 240 |
| tgatgaccaa gggccgctac tcactagatg tgtggagcta ggagcttacc aacctcccac | 300 |
| ccctcgg | 307 |

<210> SEQ ID NO 390
<211> LENGTH: 248
<212> TYPE: DNA
<213> ORGANISM: Rattus norvegicus

<400> SEQUENCE: 390

| | |
|---|---|
| tcttggagaa ggcattgccc gaagtgaatt gttccttttc ttcactacca tcctccagaa | 60 |
| ctactcagtg tccagccctg tggatcctaa caccattgat atgactccca aggagagtgg | 120 |
| attagccaaa gtagccccag tgtacaagat ttgctttgta gcccgctgat tgtgctgagg | 180 |
| cagtcagccg actcacttct gttcaaaatg gccccatttt tctgattctg ggagacctgc | 240 |
| tggagacc | 248 |

<210> SEQ ID NO 391
<211> LENGTH: 283
<212> TYPE: DNA
<213> ORGANISM: Rattus norvegicus

<400> SEQUENCE: 391

-continued

```
atggttttgg acccctgtcat tccctgtgga gagctggtgg cagaagtact tcagatccct      60
tttgtaaaca cattgaggtt cagcatgggc tactccatgg agaaatactg cggccaactt     120
ccagttccac tttcgtatgt accggttgtc agggtgaact aacagaccat atgaccttta    180
cagagagggt gaaaaatatg atgctttcac tgttttttga gttttggctc cagcaatatg    240
actttgcatt ctgggatcag ttttacagta aaactctagg aag                      283
```

<210> SEQ ID NO 392
<211> LENGTH: 290
<212> TYPE: DNA
<213> ORGANISM: Rattus norvegicus
<220> FEATURE:
<221> NAME/KEY: unsure
<222> LOCATION: (1)..(290)
<223> OTHER INFORMATION: unsure at all n locations

<400> SEQUENCE: 392

```
ggactatctc cccttaagtg ggaagggctt agtcaaatgc agtanagagc tataaaacac      60
cgagaactct tgatgtgttg tgaaacttag agggagcagc ttttttaacaa gagaactcaa    120 gcaattgctg ccatgccggg gaagccagtc cttcactact tcgatggcag ggggagaatg    180
gagcccatcc ggtggctcct ggctgcagct ggagtagagt ttgaagaaca atttctgaaa    240
actcgggatg acctggccag gctaaggaat gatgggagtt tgatgttcca                290
```

<210> SEQ ID NO 393
<211> LENGTH: 281
<212> TYPE: DNA
<213> ORGANISM: Rattus norvegicus
<220> FEATURE:
<221> NAME/KEY: unsure
<222> LOCATION: (1)..(281)
<223> OTHER INFORMATION: unsure at all n locations

<400> SEQUENCE: 393

```
ttgcactacc ctgcaaggct gtgttgcagg gcccggaagg ctcactgttc cgaaatggcc      60
gagcagtcag acaaggatgt gaagtactac actctggang gagattcaga agcacaaaga    120
cagcaagagc acctgggtga tcctacatca taagtgtacg atctgaccaa gtttctcgaa    180
gagcatcctg gtggggaaga agtcctaaga gagcaagctg ggggtgatgc tactgagaac    240
ttgaggacgt ccgggcactc taacggatgc acgagaactg t                         281
```

<210> SEQ ID NO 394
<211> LENGTH: 287
<212> TYPE: DNA
<213> ORGANISM: Rattus norvegicus
<220> FEATURE:
<221> NAME/KEY: unsure
<222> LOCATION: (1)..(287)
<223> OTHER INFORMATION: unsure at all n locations

<400> SEQUENCE: 394

```
ccgctgctta tgccatggtc ctggaactgt acctggatct gctgtcgcag ccctgtcgcg      60
ctatttatat cttcgccaag aagaacaata tcccnttcca gatgcatact gtggagctgc    120
gcaagggtga gcacctcagc gatgctttgc ccagtgaacc ccatgaagaa ggtaccagcc    180
atgaaggatg gtggcttcac cttgtgtgag agtgtggcca tcctgctcta cctggcgcac    240
aagtataagg ttcctgacca ctggtacccc caagactgca ggcccgt                   287
```

<210> SEQ ID NO 395
<211> LENGTH: 293

```
<212> TYPE: DNA
<213> ORGANISM: Rattus norvegicus

<400> SEQUENCE: 395
aagagaatcg cattaaagag aaagaaaagc aaagaatgga ctttcttcag ctgatgataa      60
actcccagaa ttccaaagtc aaagactctc ataaagcatt atccgatgtg agattgtgg     120
cccagtcagt tatcttcatt tttgccggct atgagaccac tagcagtgct ctttcctttg    180
ttttgtattt gctggccatt caccctgata tacagaagaa actgcaggat gaaattgatg    240
cagctctccc caataaggca catgccacct atgatccct gctacaaatg gag            293

<210> SEQ ID NO 396
<211> LENGTH: 266
<212> TYPE: DNA
<213> ORGANISM: Rattus norvegicus

<400> SEQUENCE: 396
gttggcctcc caataagtag ggtcaacatt tagtcaaaat atgcgattgt tgcaaagctt     60
tcgaaggctg gctttgtggg tacagtgtat ccatagatgc ctgaattaac tgaagatctt    120
aactgcagat tctacacatt tctcatcctc taatggcttc ctctggctgc ccagggctga    180
agaaacttct tcactgtggg gaggttgctg actctggttc tccagggcct cagcagaggg    240
aagttggcca agcgtgggg tccact                                           266

<210> SEQ ID NO 397
<211> LENGTH: 259
<212> TYPE: DNA
<213> ORGANISM: Rattus norvegicus

<400> SEQUENCE: 397
gtcaaatggc tacccaaaa cgatctgctt ggtcatccaa aggctcgggc gttcatcaca      60
cactccggtt cccatggtat ttatgaagga atatgcaatg gggttccaat ggtgatgatg    120
cccttgtttg gtgatcagat ggacaacgcc aagcgcatgg aaactcgggg agctggggtg    180
accctgaatg tcctggaaat gactgccgat gatttggaaa acgcccttaa aactgtcatc    240
aataacaaga gttacaagg                                                  259

<210> SEQ ID NO 398
<211> LENGTH: 252
<212> TYPE: DNA
<213> ORGANISM: Rattus norvegicus

<400> SEQUENCE: 398
gaaactttaa gaaagtgac tacttttgc ctttctcagc aggaaaacga gcttgtgttg       60
gagagggcct ggcccgcatg cagttgtttc tattcttgac aaccatttta cagaacttta    120
acctgaaatc tctggttcac ccaaaggaca ttgatacgat gccagttctg aatggttttg    180
cctctctgcc acccacttac cagctctgct tcattccttc ctgaatagat caggcatttt    240
ggctctactg tg                                                         252

<210> SEQ ID NO 399
<211> LENGTH: 272
<212> TYPE: DNA
<213> ORGANISM: Rattus norvegicus
<220> FEATURE:
<221> NAME/KEY: unsure
<222> LOCATION: (1)..(272)
<223> OTHER INFORMATION: unsure at all n locations
```

```
<400> SEQUENCE: 399
gngagccaat ggcnctcttc atttttctgg ggatttggcn ttcttntttg gttttcntt      60 ttctatngaa tcagcaccat gtcagangga agctcccacc nggtcccact cctctaccaa    120
tttttggcaa tattttgcaa ntgggtgtta aaaatatcag caaatctatg tgcatgcnag    180
cgaaagagta cgggcctggn tcaccatgta tctgggcatg aagcccactg tggtgctgta    240
tggatatgaa gtattgaaag aagctctgat tg                                  272

<210> SEQ ID NO 400
<211> LENGTH: 294
<212> TYPE: DNA
<213> ORGANISM: Rattus norvegicus

<400> SEQUENCE: 400
catccgtggg ctggctcacg ccattcgcct gttcctggag tatacagaca caagctatga    60
ggacaagaag tacagcatgg gggatgctcc cgactatgac agaagccagt ggctgagtga   120
gaagttcaaa ctgggcctgg acttccccaa tctgccctac ttaattgatg ggtcacacaa   180
gatcacccag agcaatgcca tcctgcgcta ccttggccgg aagcacaacc tttgtgggga   240
gacagaggag gagaggattc gtgtggacgt tttggagaac caggctatgg acac          294

<210> SEQ ID NO 401
<211> LENGTH: 276
<212> TYPE: DNA
<213> ORGANISM: Rattus norvegicus

<400> SEQUENCE: 401
gctgcgagca ggtctgaccc attgctctct ctgctcagag ttccccaggt ctgaagtctg    60
cctgaaagat gtcagccctc aaagctgtct tccagtacat tgacgaaaac caggaccgct   120
ttgtcaagaa acttgcagaa tgggtggcca tccagagcgt gtccgcgtgg ccggagaaga   180
gaggagagat cagaaggatg acggaagcgg cagtgcagat gtccagaggc tgggggatc   240 tgtggagctg gtggatatcg ggaagcagaa gctccc                             276

<210> SEQ ID NO 402
<211> LENGTH: 271
<212> TYPE: DNA
<213> ORGANISM: Rattus norvegicus
<220> FEATURE:
<221> NAME/KEY: unsure
<222> LOCATION: (1)..(271)
<223> OTHER INFORMATION: unsure at all n locations

<400> SEQUENCE: 402
ctgacctgac ccatgatgta agggnccgta ggggagcatc accactgcaa aggctgacta    60
aggnctgttn ggctaaaggt cnctttgaag cccagtgtct anagtcacac cttctttgct   120
ctgggcccag gaggcctact tcttcttttt ctcgnggaat cctggaatct taaagataaa   180
agaacctaga aagaaaatca aacccacttt ccttgtgggg cagatggtaa tatgggactg   240
agaacagcaa acctggggtc ttggagagga g                                   271

<210> SEQ ID NO 403
<211> LENGTH: 253
<212> TYPE: DNA
<213> ORGANISM: Rattus norvegicus

<400> SEQUENCE: 403
cgcactgctc ctagggcaag agccttcacc tcttctacag ccaacaccat gcgcgagatc    60
```

| | |
|---|---|
| gtgcacatcc aggcgggcca atgcggcaac cagatcggcg ctaaggcaac aaatatgtac | 120 |
| ctcgggccat cctagtggac ctggagccag gcaccatgga ctcagtgagg tcgggaccat | 180 |
| tcggccagat cttcaggcca gacaactttg tgttcggtca gagtggtgca ggaaataact | 240 |
| gggcaaaggg cca | 253 |

<210> SEQ ID NO 404
<211> LENGTH: 312
<212> TYPE: DNA
<213> ORGANISM: Rattus norvegicus

<400> SEQUENCE: 404

| | |
|---|---|
| cagctggctt cctacataca gttctgtgaa agagatcaga gagtgaaaga aagatggcgg | 60 |
| gggattcaag ccgctgggct gcagtctccc ttctctctgc ctgtcagcaa agttattttg | 120 |
| ctttgcaagt cggacgagta agattaaaat acaagatcgc acctccagca gtcacgggct | 180 |
| ctctggagtt tgagagaata tttcgcgcac agcaaaactc tttggagttt tattccgtat | 240 |
| tcatcatatc gctgtggatg gctggatggt atttcaatca gttttttgca acctgtctgg | 300 |
| gtctcctgta ca | 312 |

<210> SEQ ID NO 405
<211> LENGTH: 245
<212> TYPE: DNA
<213> ORGANISM: Rattus norvegicus
<220> FEATURE:
<221> NAME/KEY: unsure
<222> LOCATION: (1)..(245)
<223> OTHER INFORMATION: unsure at all n locations

<400> SEQUENCE: 405

| | |
|---|---|
| ctgccggtcg cttcctgagc ctcctctggc tctgtgtctc tgtcctcagc ttccacgtcc | 60 |
| tcgcccgacn gcgccatgga gggttaccat aagccagatc agcagaagct ccaggccctg | 120 |
| aaggacacag ccaatcgcct gcgcatcagc atccanncca ggccaccacc gcggcaggcg | 180 |
| nggacacccc acatcttgna gtagcgcngn cggagagcng gtcgnnctgn tattnnnnac | 240 |
| caggc | 245 |

<210> SEQ ID NO 406
<211> LENGTH: 299
<212> TYPE: DNA
<213> ORGANISM: Rattus norvegicus

<400> SEQUENCE: 406

| | |
|---|---|
| tcatacccaa gggaacagca gtactaacat cacttacatc agtgctgcat gacagtaagg | 60 |
| aattccccaa cccagagatg tttgacccag gtcactttct agatgagaat ggaaacttta | 120 |
| agaaaagtga ctacttcatg cctttctcag caggaaaacg gaaatgtgtg ggagagggcc | 180 |
| ttgccagtat ggagctgttt tgttcctga ccaccatttt acagaatttc aaactgaaat | 240 |
| ctctgtctga tccaaaggac atcgatataa actcaatacg ttctgagttt tcatcaatc | 299 |

<210> SEQ ID NO 407
<211> LENGTH: 290
<212> TYPE: DNA
<213> ORGANISM: Rattus norvegicus

<400> SEQUENCE: 407

| | |
|---|---|
| ggaaggggaa gaatgccagt ttttgaaaag gctactaaag gactgggcat tagttttagc | 60 |

```
cgtggaaatg tatggagagc cacaagacat ttcacagtca atacccctgag gagtttgggc    120 atggggaaac ggaccattga gatcaaagtg caagaggaag cagagtggct agtgatggaa    180
ctgaagaaaa ccaaaggctc accctgtgat cccaaattca tcataggatg tgctccctgc    240
aatgtcatct gctccattat cttccagaat cgtttcgatt ataaagataa                290
```

<210> SEQ ID NO 408
<211> LENGTH: 221
<212> TYPE: DNA
<213> ORGANISM: Rattus norvegicus
<220> FEATURE:
<221> NAME/KEY: unsure
<222> LOCATION: (1)..(221)
<223> OTHER INFORMATION: unsure at all n locations

<400> SEQUENCE: 408

```
catcagttct gtgttcaaag ttaacatcag agataatggg ctcctgncnt cncntcccnt    60
ttttgntngc tnggggcantg gnaaccngga agnccnntgg aganttccan aaaagaaaaa    120 atttagggc acaaatgtga gaaaaancnt cacaancttn ggnananannc ccctgntgc    180 gcctnttgtg gggctgccct atgtccaatc cagctatatt g                        221
```

<210> SEQ ID NO 409
<211> LENGTH: 116
<212> TYPE: DNA
<213> ORGANISM: Rattus norvegicus
<220> FEATURE:
<221> NAME/KEY: unsure
<222> LOCATION: (1)..(116)
<223> OTHER INFORMATION: unsure at all n locations

<400> SEQUENCE: 409

```
attttgagat ggaacgattt gaagtcttgg gtgtcccctt cagtctccaa ctttgggaca    60
ctgctggtca ggagaggttc aagtgcatcg cttccacaca acatangagn gnnatt        116
```

<210> SEQ ID NO 410
<211> LENGTH: 275
<212> TYPE: DNA
<213> ORGANISM: Rattus norvegicus
<220> FEATURE:
<221> NAME/KEY: unsure
<222> LOCATION: (1)..(275)
<223> OTHER INFORMATION: unsure at all n locations

<400> SEQUENCE: 410

```
cacagcccct accagcncac cctccataac tgcaccaaga ggatctatcc aacacctccc    60
tgagcaggag gagcctgaag actccaaggg aaagagtcct gaggaaccct ttcctgtgca    120
gctggatcta accacaaacc cacagggtga cacactggat gtctccttcc tctacctgga    180
gcctgaggaa aagaaactgg tggtcctgcc tttccctggg aaggaacagc gctcccctga    240
gtgcccgggg cccgaaaagc aaagaacccc ctgat                              275
```

<210> SEQ ID NO 411
<211> LENGTH: 300
<212> TYPE: DNA
<213> ORGANISM: Rattus norvegicus
<220> FEATURE:
<221> NAME/KEY: unsure
<222> LOCATION: (1)..(300)
<223> OTHER INFORMATION: unsure at all n locations

<400> SEQUENCE: 411

```
ccctcttcaa tatcctacgc ttccctctgt ccatgcttcc catggtgncc tcatcgatcc    60
```

```
tccaggccag tgtttctgtg gaccggctgg agaggtattt gggaggagac gatttagaca    120
catctgccat tcgccgcgtc agcaattttg ataaagctgt gaagttttca gaggcctctt    180
ttacttgggc ccggacttgg aagccacaat ccaagatgtg aacctggaca taaagccagg    240
ccaatggtgg ctgtggtggg cactgtagct ctgggaaatc ctctttggta tcagccatgt    300
```

<210> SEQ ID NO 412
<211> LENGTH: 286
<212> TYPE: DNA
<213> ORGANISM: Rattus norvegicus
<220> FEATURE:
<221> NAME/KEY: unsure
<222> LOCATION: (1)..(286)
<223> OTHER INFORMATION: unsure at all n locations

<400> SEQUENCE: 412

```
cnagaagtta gtggagtact tgaagcagag ttcgttgatg ctgtgtttct ggatcctttt     60
gatgtgtgtg ggctaactgg tgccaagtac tttctctccc gtcagtggtc ttcagcaggg    120
ggatattttg tcactatctt gaagaangct cccagtgccc cagtcctcct tcatatgtcc    180
ccagaggtat cttgaaactc acagatacca tgactttcaa ggaaagagtg tggaacttct    240
ttcctaatgg gggagcatgc attctgtccc agtttttcaa aactgc                   286
```

<210> SEQ ID NO 413
<211> LENGTH: 272
<212> TYPE: DNA
<213> ORGANISM: Rattus norvegicus

<400> SEQUENCE: 413

```
agagaagcct gctgaggaaa cactggaaag ccttacctca ggcactaagt tgaaggaaaa     60
acgacaatgg ccacaatggt agaactgagc cctacaagtg agcagtgtga gtttgtccta    120
ggtctgccag tgaataagaa gaccctcccc cggaaagtcc cgagtttatg ttccatgcgc    180
tattcaatag ccttcatcgc acatatctgc aacttcacat tgatagcaca gaattccatc    240
ataagcatca ccatggtagc catggtcaac aa                                  272
```

<210> SEQ ID NO 414
<211> LENGTH: 103
<212> TYPE: DNA
<213> ORGANISM: Rattus norvegicus
<220> FEATURE:
<221> NAME/KEY: unsure
<222> LOCATION: (1)..(103)
<223> OTHER INFORMATION: unsure at all n locations

<400> SEQUENCE: 414

```
agctccgggg gaggtcgccc acatccttca ggntgaaagc tgcagtgttg gctgtggccc     60
tggtcttcct gacaggttgc caagcttggg agttctggca gca                      103
```

<210> SEQ ID NO 415
<211> LENGTH: 273
<212> TYPE: DNA
<213> ORGANISM: Rattus norvegicus
<220> FEATURE:
<221> NAME/KEY: unsure
<222> LOCATION: (1)..(273)
<223> OTHER INFORMATION: unsure at all n locations

<400> SEQUENCE: 415

```
aacgccctta aaactgtcat caataacaag agttacaagg agaacatcat gcgcctctcc     60
```

```
agccttcaca aggaccgtcc tatcgagcct ctggacctgg ctgtgttctg ggtggagtac      120
gtgatgaggc acaaggnggc gccacacctg cgccccgccg cccacgacct cacctggtac      180
cagtaccact ccttggacgt gattggcttt ctcctggcca tcgtgttgac ggtggtcttc      240
attgtctata aaagttgtgc ctatggctgc cgg                                   273

<210> SEQ ID NO 416
<211> LENGTH: 106
<212> TYPE: DNA
<213> ORGANISM: Rattus norvegicus
<220> FEATURE:
<221> NAME/KEY: unsure
<222> LOCATION: (1)..(106)
<223> OTHER INFORMATION: unsure at all n locations

<400> SEQUENCE: 416
gaagannnac ctggacaccc agactgttgg agancntccg ggggatgtcg ctcacatcct      60
tcaggatgaa anctgcagtg gtggctgnag gnnctggtct ncctga                    106

<210> SEQ ID NO 417
<211> LENGTH: 294
<212> TYPE: DNA
<213> ORGANISM: Rattus norvegicus
<220> FEATURE:
<221> NAME/KEY: unsure
<222> LOCATION: (1)..(294)
<223> OTHER INFORMATION: unsure at all n locations

<400> SEQUENCE: 417
cactaaagca aagcagacaa ctccagctct ccacacagct ggtctctgac accttggggg      60
acacaagggc cctagctatg gagtgcgtat tccacagaca cctatggtta ccttggatac     120
tgccaaaact cttaaataca tggactttta cctcagaaac ttgtcttcag atatcctgtt     180
aatcttcagt ttttgtttgt ttttgttttt nggaggaagg cctctctcta tgtagctatg     240
gctgtcctag aatcactctg tagatcaggc tggcctcaga ctcatgcctc tgct           294

<210> SEQ ID NO 418
<211> LENGTH: 262
<212> TYPE: DNA
<213> ORGANISM: Rattus norvegicus

<400> SEQUENCE: 418
cgaggcttcc aggtagcggt cggtcgcagt ctgtcccagg gtacgacccg gccttgggca      60
cagattcgcg gacccggggc tgcctcttta agggaggggg tggagccacg agtgaggatc     120
gaaaagctcc agaaaacttg aggccagagc cccgcaccag ggtgcagcca tgagtgcgga     180
ggtgaaggtg acagggcaga accaggagca atttctgctc cttgccaagt cggctaaggg     240
ggcagcactg gccacactca tc                                              262

<210> SEQ ID NO 419
<211> LENGTH: 145
<212> TYPE: DNA
<213> ORGANISM: Rattus norvegicus
<220> FEATURE:
<221> NAME/KEY: unsure
<222> LOCATION: (1)..(145)
<223> OTHER INFORMATION: unsure at all n locations

<400> SEQUENCE: 419
acacaaagcn atttanantg ccagactata cttggtttaa aggaatacct tttcatgnct      60
ctgggattca aaagncactt tnccaaaatg tnnggnaana attttgtggn cnanccccga     120
```

```
nttcatntga ncggcttanc ccagt                                          145
```

<210> SEQ ID NO 420
<211> LENGTH: 271
<212> TYPE: DNA
<213> ORGANISM: Rattus norvegicus

<400> SEQUENCE: 420

```
ctccaacctg gtgcgccacc agcggctgca caccggggaa aagccgtatg tctgcagcca    60
gtgtggcaag gccttcatct ggagctctgt gctcatcgaa caccagcgca ttcacacagg   120
cgagaagccc tacaagtgtg aagactgcgg caaggccttc cgaggacggt cgcatttctt   180
ccggcactta cggacccaca cgggcgagaa gcccttctcc tgtggctcct gtggcaaagc   240
gtttggccag agctctcagc tcatccagca c                                  271
```

<210> SEQ ID NO 421
<211> LENGTH: 282
<212> TYPE: DNA
<213> ORGANISM: Rattus norvegicus
<220> FEATURE:
<221> NAME/KEY: unsure
<222> LOCATION: (1)..(282)
<223> OTHER INFORMATION: unsure at all n locations

<400> SEQUENCE: 421

```
cagttagaag ttcctgggna ggccctgtgt agacccagcc tagctgagta ctgattcatt    60
ttgatgtgag tgggaagaat gggggagatt cgcagctttg tcctcatcac tgttgctctg   120
attctgggca aggagagctg ggtcctcgga gatgagaact gtttgcagga gcaggtgagg   180
ctcagggctc agtgcgcca gcttgagacc cgggtcaaac aacaacgggt ggtgattgca   240
cagctcttgc acgagaagga ggtccagttc ctggatagag ga                     282
```

<210> SEQ ID NO 422
<211> LENGTH: 222
<212> TYPE: DNA
<213> ORGANISM: Rattus norvegicus
<220> FEATURE:
<221> NAME/KEY: unsure
<222> LOCATION: (1)..(222)
<223> OTHER INFORMATION: unsure at all n locations

<400> SEQUENCE: 422

```
ctgaagacca acttgtcctc agtgagcgac tgtgtgcagc aggtggtgga gcttctgcaa    60
gancagagca ttgttcccca caccaccatc aaaggcatcc atgaactctt tgtgccggaa   120
aacaaaattg atcaaatccg agctgagtta gagactctcc catcactacc aattaccaag   180
ctggatctgc agtgggtgca gattctgagc gaaggctggg cc                     222
```

<210> SEQ ID NO 423
<211> LENGTH: 275
<212> TYPE: DNA
<213> ORGANISM: Rattus norvegicus

<400> SEQUENCE: 423

```
gagaaaggcc accacctagc taggtgaggt gtgccagcat ggtcctgggg gtctcactgt    60
ccccagccct gggacgctgg ttccgccatg caatccctt cgctatcttc acgctgttac   120
ttctttatat cagtgtatgg ctcttccatg agtggccctt tgagttgcca gctcaaagaa   180
ctcagcagtc cggcctgtgg gaactcaagc tctcttctcc ttctccagcc ctcacctctc   240
```

-continued tgcttcctgt cacctcaggt gttttacaag gctga                                275

<210> SEQ ID NO 424
<211> LENGTH: 279
<212> TYPE: DNA
<213> ORGANISM: Rattus norvegicus
<220> FEATURE:
<221> NAME/KEY: unsure
<222> LOCATION: (1)..(279)
<223> OTHER INFORMATION: unsure at all n locations

<400> SEQUENCE: 424
attcctcatt gcatgatgcc ttcaaataaa gggcaacgtg aatacagttt ataaatcaac     60
gagtatttta agccttgttt aaaacatctt tttactccan nnnnnnnnnn nnnnnnnnnn    120
nncaaactaa atcattgtag ctaacctgta atatacgtag tagttgacct ggaaaagttg    180
taaaaatatn gctttaaccg acacgtaaat atttcagata aacattatat tctttgtata    240
taaaanaaag aaaannangn caatggnnga atnaactct                           279

<210> SEQ ID NO 425
<211> LENGTH: 288
<212> TYPE: DNA
<213> ORGANISM: Rattus norvegicus
<220> FEATURE:
<221> NAME/KEY: unsure
<222> LOCATION: (1)..(288)
<223> OTHER INFORMATION: unsure at all n locations

<400> SEQUENCE: 425
gtgttcgcag gttcccagca ctcttgccga aggactcttg tccttctcta ccagagcagc     60
atangaggga atggctgccg tgtctccacc taccagatgt caggcatcgg tgacgtttga    120
agatgtggct gtgaccttca cagatgacga gtggaagcgt ctggtaccca tgcagagagc    180
actctacaag accgtgatgc tggagaacta tgagagcatc atctctctgg ggcttcccgt    240
tcctcgacct gatgtgattc ttcagttcaa gagaaggggc gaatcctg                 288

<210> SEQ ID NO 426
<211> LENGTH: 286
<212> TYPE: DNA
<213> ORGANISM: Rattus norvegicus
<220> FEATURE:
<221> NAME/KEY: unsure
<222> LOCATION: (1)..(286)
<223> OTHER INFORMATION: unsure at all n locations

<400> SEQUENCE: 426
gtctgggctg gagctaaagg acacacagna gcaagtccac agatccgtga tgagtcccac     60
gggggcaggc ctganggcca ccatcttctg catcctgacc tgggtcagcc tgacagctgg    120
ggaccgcgta tacatccacc cctttcatct cctctactac agcaaganca nctgcgccca    180
gctggagaac cccagtgtgg agacgctccc agagccaacc tttgagcctg tgcccattca    240
ggccaagacc tcccccgtgg atgagaagac cctgcgagat aagtcg                   286

<210> SEQ ID NO 427
<211> LENGTH: 235
<212> TYPE: DNA
<213> ORGANISM: Rattus norvegicus

<400> SEQUENCE: 427
gaggattcac tcacatttgc ttcccgctgg ccatgagtga gctgcccttt ctgagtccag     60
agggagccag agggcctcac aacaacagag ggtctcagag ctccctggag gaaggctcag    120

```
ttacaggctc agaggctcgg cacagcttag gtgtcctgaa tgtgtccttc agcgtcagaa      180
ccgtgtcggg ccctggtgga acatcaaatc atgccagcag aagtgggaca ggaaa           235
```

<210> SEQ ID NO 428
<211> LENGTH: 249
<212> TYPE: DNA
<213> ORGANISM: Rattus norvegicus

<400> SEQUENCE: 428

```
ccctggttct ggaagtggag atcgtgagtc atggctgctc cccgagacgc agagatccac      60
aaggacgttc agaactacta tgggaatgta ctgaagacat ctgcagacct ccagactaat     120
gcttgtgtca ccccagccaa gggggtccct gagtacatcc ggaaaagtct gcagaatgta     180
catgaagaag ttatttccag gtattatggc tgcggtctgg tggtgcctga gcatctggaa     240
aactgccgg                                                             249
```

<210> SEQ ID NO 429
<211> LENGTH: 233
<212> TYPE: DNA
<213> ORGANISM: Rattus norvegicus

<400> SEQUENCE: 429

```
ctgaacttga ccaaagggag actcaggttg gaaacaaaat cccagggatg atacacggaa      60
aaactccatt aggcacagtg acatacatgt gtaattcaaa cgctgcactt gagagactga     120
ggcaggagga gatctatcga aaggttgaga ccaactagct gtaggctagc ctgggctatg     180
ctgttaagac cttgtcacaa agtacaagaa gggagaataa aagaatattt cct            233
```

<210> SEQ ID NO 430
<211> LENGTH: 287
<212> TYPE: DNA
<213> ORGANISM: Rattus norvegicus
<220> FEATURE:
<221> NAME/KEY: unsure
<222> LOCATION: (1)..(287)
<223> OTHER INFORMATION: unsure at all n locations

<400> SEQUENCE: 430

```
tcaagagcat atgtgcggca cagagtggac ntgatggctt tgttgttgt tttgttatgt       60 gtgcacatct atgttttcat atctaccggt tgggtatgcc tttgtccctg ggtagggact     120
ggctctctgg acaagtagat gtcctgttag cctgcagaca tcacatgact ctcaagaacg     180
aatcgtgtat cctggtccct gctcctgtgc atgcacattc ccctcctctg tcccgaggca     240
gaggcaaggg tgtgtgaggc ctatgggcag aggccatatt gtgaaga                   287
```

<210> SEQ ID NO 431
<211> LENGTH: 183
<212> TYPE: DNA
<213> ORGANISM: Rattus norvegicus

<400> SEQUENCE: 431

```
ctaaaattaa gatagagtga atgagacaga tatctgtaga cactgtatt tcttgtgtga       60 tcagatctag tgtggtggat gatagaagtt gaacttgctt tattgctatg tgttaaaata     120
ttttgtttgc attaaatggc ctattgaaat gcttttctgt tcctataata aaataaccctg    180 atg                                                                    183
```

<210> SEQ ID NO 432

-continued

```
<211> LENGTH: 287
<212> TYPE: DNA
<213> ORGANISM: Rattus norvegicus
<220> FEATURE:
<221> NAME/KEY: unsure
<222> LOCATION: (1)..(287)
<223> OTHER INFORMATION: unsure at all n locations

<400> SEQUENCE: 432
tcaagagcat atgtgcggca cagagtggac ntgatggctt tgttgttgt tttgttatgt       60 gtgcacatct atgttttcat atctaccggt tgggtatgcc tttgtccctg ggtagggact     120
ggctctctgg acaagtagat gtcctgttag cctgcagaca tcacatgact ctcaagaacg    180
aatcgtgtat cctggtccct gctcctgtgc atgcacattc ccctcctctg tcccgaggca    240
gaggcaaggg tgtgtgaggc ctatgggcag aggccatatt gtgaaga                   287

<210> SEQ ID NO 433
<211> LENGTH: 283
<212> TYPE: DNA
<213> ORGANISM: Rattus norvegicus
<220> FEATURE:
<221> NAME/KEY: unsure
<222> LOCATION: (1)..(283)
<223> OTHER INFORMATION: unsure at all n locations

<400> SEQUENCE: 433
ctgggntcan cacgttntgc tgagnannng gctgntgtgt accccagag atccctnctg       60 ttggaccttc accagtccng ggnggctgg gactcccaca cctcaagccc gagctatgac     120
ttacattcca ctgctgggag aagagaggcg gggcccagag tatcctgccc ttgggagtca    180
aagaccctag gngccaggct ggcacaggga tggggaggct ggncttttat aaatatnata    240
tgcagannaa aagannaaaa naagggcggc cnccgacaag nna                       283

<210> SEQ ID NO 434
<211> LENGTH: 295
<212> TYPE: DNA
<213> ORGANISM: Rattus norvegicus

<400> SEQUENCE: 434
aagatcggaa gaatcacagg gctggaccct gcaggaccta tgtttgaggg aacttccccc       60
aacgagcgcc tttctccaga tgatgccaat tttgtggatg ctattcatac ctttaccagg     120
gagcacatgg gtctgagtgt gggcatcaaa cagcccattg cccactatga cttctacccc    180
aacgggggct ccttccagcc tggctgccac ttcctggagc tctacaaaca cattgcagag    240
catgggctta aatgccataa cccagaccat caaatgtgcc catgagcgtt ctgtg           295

<210> SEQ ID NO 435
<211> LENGTH: 133
<212> TYPE: DNA
<213> ORGANISM: Rattus norvegicus

<400> SEQUENCE: 435
ccctgattct tttgctgtat agccctggat gtgtaatgca gacattatct aactgtgtgt       60
ggtaaccttg acatcacaga actgctagtg aacgaggtaa aataataaaa ggtacaacca     120
gtgcatcgca aaa                                                         133

<210> SEQ ID NO 436
<211> LENGTH: 212
<212> TYPE: DNA
<213> ORGANISM: Rattus norvegicus
```

```
<220> FEATURE:
<221> NAME/KEY: unsure
<222> LOCATION: (1)..(212)
<223> OTHER INFORMATION: unsure at all n locations

<400> SEQUENCE: 436
accaccagtt tcgaagctgg ccggtcttgt cttaggtcga tggtgaagac aacggcatct    60
tcaccagccg acaggaacgt gcagggagag tctggttcta gggccaactt gtgggatgct   120
cccttgagct gggccacacg cttggtgttc ttgcagcact gtgtagcang cttctcctgc   180
gactcggacc tgcccatccc ggcacacata gc                                 212

<210> SEQ ID NO 437
<211> LENGTH: 291
<212> TYPE: DNA
<213> ORGANISM: Rattus norvegicus

<400> SEQUENCE: 437
tttaataacg taatgacgcg gtccttttcc taatccctaa aaacctgtct cataaagtgt    60
aatgggggag cagcccttttt ggtgttgcaa aatgaagttc caggcttcta aaatgttgcc   120
atgtattgaa aggagctaat gccattgtaa atgttattag tttcacattt cttgagcagc   180
ctagagtaca gggtgaacat ttgtagatct tgtaatgatg tattgtgctg tggaagtact   240
gtgtgtgaat agcagtagtg gggcaaaaag caatcttgtc attggaatgt a             291

<210> SEQ ID NO 438
<211> LENGTH: 262
<212> TYPE: DNA
<213> ORGANISM: Rattus norvegicus

<400> SEQUENCE: 438
ggataaatga gacggctcgg gtcgagtgca tttgcagggg actcgggttt ggttcccagc    60
gtccacgttg ggcagcacac aagtgtccgt aactctagct ctatgggatc tgacccattt   120
ctggcctctt cagcacctgc acaaatgtgg cagacacata tacgcttaag taaaaataat   180
taaaaaaaac gaatctttaa aacatttttt aaaagaagtg atggagtgaa ttcctgcctt   240
atggcctgct ggaaatggaa ca                                            262

<210> SEQ ID NO 439
<211> LENGTH: 272
<212> TYPE: DNA
<213> ORGANISM: Rattus norvegicus

<400> SEQUENCE: 439
tgggcttctt tcactgggac acttgggaca ccgctgagtt actaacagct ttgtttacac    60
agtaggaaga ggggcataga gagctgtgcc tctatggtga gcctctggga ctgaagtttg   120
ccacgactag tggttggaca cctgggaggc tggctaccta cctgtcttac tccctgaagg   180
acagggttga atctctgggt tccagtcctt agggagatga agtactgtct gtcagctgct   240
ggctgtgctt tttgaagagg ccaaattgtt tc                                 272

<210> SEQ ID NO 440
<211> LENGTH: 284
<212> TYPE: DNA
<213> ORGANISM: Rattus norvegicus

<400> SEQUENCE: 440
acagaaccca acctgctact aatcacggag aagaatgtgg aggacaagaa taaggctaga    60
```

```
agccagagca agtgaggact gagcaaggga agggagaacc gattgccatc ggccttcatg      120
ctctggttag ggtgaggttg gggccaagag gactgggcct ggcagatctt caagtcattg      180
ggaagatgga gataccactg tagggtgaa caccgggaga cctaggagat cccctcccca       240 cccttctct tggcctccga ttcactcctg tcccgttccc tgac                        284
```

<210> SEQ ID NO 441
<211> LENGTH: 233
<212> TYPE: DNA
<213> ORGANISM: Rattus norvegicus

<400> SEQUENCE: 441

```
ctgaacttga ccaaagggag actcaggttg gaaacaaaat cccagggatg atacacggaa      60
aaactccatt aggcacagtg acatacatgt gtaattcaaa cgctgcactt gagagactga     120
ggcaggagga gatctatcga aaggttgaga ccaactagct gtaggctagc ctgggctatg     180
ctgttaagac cttgtcacaa agtacaagaa gggagaataa agaatatttt cct            233
```

<210> SEQ ID NO 442
<211> LENGTH: 273
<212> TYPE: DNA
<213> ORGANISM: Rattus norvegicus
<220> FEATURE:
<221> NAME/KEY: unsure
<222> LOCATION: (1)..(273)
<223> OTHER INFORMATION: unsure at all n locations

<400> SEQUENCE: 442

```
accgactgat gttcccacgg atgctaatga agctggtgag cctccggact ttgagcagcg      60
tccattcaga gcaagtgttt gcncttcgcc tgcaggacaa aaaacttccc cctctgctct     120
ccgagatctg ggatgtccac gaatgactgt ttctccgtgt cctcngtgtt ggcaaggcag     180
ctgaagttac nganngcttc nnngaagngg nananncctgg ggagagaaaa nntncagggg    240
gncgaggaaa agagacnctt ntnnngnaan aag                                   273
```

<210> SEQ ID NO 443
<211> LENGTH: 264
<212> TYPE: DNA
<213> ORGANISM: Rattus norvegicus
<220> FEATURE:
<221> NAME/KEY: unsure
<222> LOCATION: (1)..(264)
<223> OTHER INFORMATION: unsure at all n locations

<400> SEQUENCE: 443

```
gnaagaagga aggttctctc ttcacctgct tctatttact tgccagcaca tctgttggga      60
tctactaacc ttgtgagatg gagcaactac tagatccttg gacttccac tcatagctga     120 tcattgttag ggggttggac tacagactgt aaatcatcat aacaaactcc cttactgtat     180
agaggctatc cataagttct gtgactctag agaaccctga ctactacaga ccctgtttca     240 aaaagaagc aaaagttagc tggg                                              264
```

<210> SEQ ID NO 444
<211> LENGTH: 283
<212> TYPE: DNA
<213> ORGANISM: Rattus norvegicus
<220> FEATURE:
<221> NAME/KEY: unsure
<222> LOCATION: (1)..(283)
<223> OTHER INFORMATION: unsure at all n locations

<400> SEQUENCE: 444

```
gaggaatcca attttctgag ctccacaagc cactctgcan nntcagatag tcaccagggt      60
cactacagga ggaattgttc catctgagag acccagcatg cattatactc gctgtctgct     120
gcttctcctg gctggactct tggaactctc tcacagtcag ccagaccaag aagagcctga     180
caatacaacc aaccaaacct acagttgttc tcacagcaga acatctccag ctaccagatt     240
gcctctggna atgccaactt tgccttccgc ctctaccacc tga                       283
```

<210> SEQ ID NO 445
<211> LENGTH: 290
<212> TYPE: DNA
<213> ORGANISM: Rattus norvegicus
<220> FEATURE:
<221> NAME/KEY: unsure
<222> LOCATION: (1)..(290)
<223> OTHER INFORMATION: unsure at all n locations

<400> SEQUENCE: 445

```
gaaattcaat tttggttttc aaaattgatt cttaaganan ataccccc ataaggaaat        60 aatatcacaa tctcataagg natggggaat acagacnagg tacnttttca ggcacattca     120
gtgtaaatat atgtagtcat ttatactgnn atattaaata atattatatt tgtgaagaca     180
gagatttatg tcttacaatg taaatganaa acagacaaac ctaatcagat atctggctgg     240
tgaagccatt ggtcagtgtt aggaatttcc agtcaggaga agaccctcta                290
```

<210> SEQ ID NO 446
<211> LENGTH: 165
<212> TYPE: DNA
<213> ORGANISM: Rattus norvegicus
<220> FEATURE:
<221> NAME/KEY: unsure
<222> LOCATION: (1)..(165)
<223> OTHER INFORMATION: unsure at all n locations

<400> SEQUENCE: 446

```
ggggaaacac attcaaagaa gaatcaggaa gagggatgtg atagggtgct tatggatggg      60
aaaccgagaa agganataac atttgaaatg taaatgaaaa atatccaatt aaaaaaaaaa     120
aancaaaccc tgcccagant tttgccngng ngacaaaaan agaga                     165
```

<210> SEQ ID NO 447
<211> LENGTH: 173
<212> TYPE: DNA
<213> ORGANISM: Rattus norvegicus
<220> FEATURE:
<221> NAME/KEY: unsure
<222> LOCATION: (1)..(173)
<223> OTHER INFORMATION: unsure at all n locations

<400> SEQUENCE: 447

```
gggaggngcc cttttttccca ccaccagaag agtttgtgtt catccatgct gtacctgttg      60
aggaacgtgt gcggactgca gtccctccca agaccataga ggagtgtgag gtgattctga     120
tggtgggact tcctggatct ggaaagaccc agtgggcact gaaatatgca aaa            173
```

<210> SEQ ID NO 448
<211> LENGTH: 189
<212> TYPE: DNA
<213> ORGANISM: Rattus norvegicus

<400> SEQUENCE: 448

```
gttattaagg ataaactgtt taatcaaatt aacgttgctt agttactgct gagtactctt      60
```

```
cctcagagct ggcgtgcgga aggagaagaa gctcaaggaa cattctaacc cagttaccag      120
aactcagata gaagactaag gtgctgtgtg acgtcctgag tattagcact gtaataaaac      180
tgtcacatg                                                              189
```

<210> SEQ ID NO 449
<211> LENGTH: 165
<212> TYPE: DNA
<213> ORGANISM: Rattus norvegicus
<220> FEATURE:
<221> NAME/KEY: unsure
<222> LOCATION: (1)..(165)
<223> OTHER INFORMATION: unsure at all n locations

<400> SEQUENCE: 449

```
gtattttncc agancaganc gtgtattgaa acataaacgt atgtgccatg aaaatcacga      60
caaaaaacta nncngatgtn ccattcaaan gtggccttct gtacatcana ggnagattct     120
ggctttctac ggcaccagaa gntgtttcac tggcnanaan aaant                     165
```

<210> SEQ ID NO 450
<211> LENGTH: 184
<212> TYPE: DNA
<213> ORGANISM: Rattus norvegicus
<220> FEATURE:
<221> NAME/KEY: unsure
<222> LOCATION: (1)..(184)
<223> OTHER INFORMATION: unsure at all n locations

<400> SEQUENCE: 450

```
cnggggaca attaaaggga ctgtgcgtac gtttctctca tgaatgaagg aagctgtctg       60
aacaaagaat tactgattca gctacgcagc agaacatatg tgctctactc tttcaagatt     120
aataatcttg ctttatgtca tattgtatat ttaatcttag tctgttgcng gggagggtct     180
atgc                                                                   184
```

<210> SEQ ID NO 451
<211> LENGTH: 271
<212> TYPE: DNA
<213> ORGANISM: Rattus norvegicus
<220> FEATURE:
<221> NAME/KEY: unsure
<222> LOCATION: (1)..(271)
<223> OTHER INFORMATION: unsure at all n locations

<400> SEQUENCE: 451

```
tgcagcccct cctccggggg cattctgttt ccagnccact tcgggctatg tagtcctctc      60
ttctgtgctg aggcctggcc cacgtcacaa gcatttcctt ccagacccac aacctccagg     120
gactgggaca aactggggca ggatgatttg ccacttgctt ggcccgctga tcccagcccg     180
atacctctcc tctctactct cccaggagac tctcaggccc agtgtgaccc tggggcttgg     240
ctgagaagct gacccagccc cagggccagc a                                    271
```

<210> SEQ ID NO 452
<211> LENGTH: 103
<212> TYPE: DNA
<213> ORGANISM: Rattus norvegicus
<220> FEATURE:
<221> NAME/KEY: unsure
<222> LOCATION: (1)..(103)
<223> OTHER INFORMATION: unsure at all n locations

<400> SEQUENCE: 452

```
caaggagaag cagataaaga agcaaacggc tnctcgctga gctggtgaaa cancaagccc      60
```
aaggcccaca gaagattcag ctgaagacgg tgatgggtga tct    103

<210> SEQ ID NO 453
<211> LENGTH: 284
<212> TYPE: DNA
<213> ORGANISM: Rattus norvegicus
<220> FEATURE:
<221> NAME/KEY: unsure
<222> LOCATION: (1)..(284)
<223> OTHER INFORMATION: unsure at all n locations

<400> SEQUENCE: 453
gccacagtcc cagcggancc cacagccgct cccgccttct ccgtgtcggg cgatccccag    60
tctgtcccca aaatgcctgt ggacttcaac gggtactgga agatgctgag caacgagaat    120
ttcgaggagt acctgcgtgc gctcgatgtc aacgtggcct tgcgaaaaat cgccaacttg    180
ctgaagccgg acaaagagat cgtgcaggat ggcgaccaca tgatcatccg cacgctgagc    240
acttttcgaa actatatcat ggacttccaa gttgggaagg agtt    284

<210> SEQ ID NO 454
<211> LENGTH: 277
<212> TYPE: DNA
<213> ORGANISM: Rattus norvegicus
<220> FEATURE:
<221> NAME/KEY: unsure
<222> LOCATION: (1)..(277)
<223> OTHER INFORMATION: unsure at all n locations

<400> SEQUENCE: 454
ttctgcataa gggcttttcca aattaagtct gtccagtaga gtgatttgct ttattattac    60
caagaataca acagctagtg aaccgtagca gcatgcgaag aggggctgta actatcacca    120
tacatgcact gtcccgtgga ggtgtgacac gggagacgtg tggatcatgt gatcattgtg    180
aacaccttgt gagcttttaaa ataaagtcca ccctgtggtg tcaaaaaana aaaaananan    240
nannaggagn nannannncn ggattangga ccnccccc    277

<210> SEQ ID NO 455
<211> LENGTH: 155
<212> TYPE: DNA
<213> ORGANISM: Rattus norvegicus
<220> FEATURE:
<221> NAME/KEY: unsure
<222> LOCATION: (1)..(155)
<223> OTHER INFORMATION: unsure at all n locations

<400> SEQUENCE: 455
gaatggaacc catgaggaat gccaccaaag gctgcaacga gtctgtagat gaggtccaca    60
nggccatgta gctgccagga ctgctctgcc gtctgcngtc ccaaacccca tccccaccaa    120
tccctgacac actaataaag gctttgtgac ctcaa    155

<210> SEQ ID NO 456
<211> LENGTH: 277
<212> TYPE: DNA
<213> ORGANISM: Rattus norvegicus

<400> SEQUENCE: 456
ggggattagc tctatctgac accttctgta tcttcattct aaagtggggt catgctttta    60
ggggtggtgt ggcgggtgcc atggaagtgg taatgcatgt gttgatgcag ggattatgca    120
agctgaaact tgttctcagg ggccatgtca gatgtgtgag aatacctgga ctcctggttt    180

```
tcctccatag taaagggtg ttctcccact ctctacaagt ctcttcatgc cagagggttt      240
tcaagactcc catttagtgg ccaggaggat ttcattg                              277

<210> SEQ ID NO 457
<211> LENGTH: 277
<212> TYPE: DNA
<213> ORGANISM: Rattus norvegicus
<220> FEATURE:
<221> NAME/KEY: unsure
<222> LOCATION: (1)..(277)
<223> OTHER INFORMATION: unsure at all n locations

<400> SEQUENCE: 457
cgangatctt gagactggtg tttctgtggt cactggtgga caggatgtat gtagcgtgcg      60
cgtgtgtgta agtgtgggtg tgtgtgcgtg ctctgctcat ctctagggaa cttcgaggtg     120
ggaagtggga ggtgggaggt ggagggaccc agtagtgaga agaactagga ggtgaggcct     180
aatgggccgc agattggtca tgttttggtg ctgatgacag aggggccagt cccaggggag     240
gaggcttngc gggccnactt tnttgtctcc tgtcgna                             277

<210> SEQ ID NO 458
<211> LENGTH: 233
<212> TYPE: DNA
<213> ORGANISM: Rattus norvegicus

<400> SEQUENCE: 458
cctcattgaa catggctcca atgaattcac tatgttctga agacatgcaa gatttcatgc      60
caaatatata ttcagtgcta aaaaacaaa atcctgtgtt cagtttagaa tgttttgatg     120
tagctgagaa gctttgccca acaacaataa ctgaagctac tgtagttcat aaagttcaca     180
tggctttata gcctttgcaa aacatatcta taaatcaatt acttttgaa aat            233

<210> SEQ ID NO 459
<211> LENGTH: 294
<212> TYPE: DNA
<213> ORGANISM: Rattus norvegicus
<220> FEATURE:
<221> NAME/KEY: unsure
<222> LOCATION: (1)..(294)
<223> OTHER INFORMATION: unsure at all n locations

<400> SEQUENCE: 459
gttccgcgga ggcggaagct cggggtgagt ccgaactaaa ccttgcgttc aagattcggc      60
gtcacccgta atccaccgcc ctggccgagg aaggcatagc tgctggaggt gtaatggacg     120
tcaacactgc tctacaagag gtgctgaaga ccgccctcat ccacgatggc ctagcacgtg     180
gcatacgcga agtgccaaag ccttagacaa gcgccaagcc catctctgcg tgcttgcatc     240
caatgtgatg agcccatgta tgtcaagctg gtgnnggcct ttttnccgaa caaa           294

<210> SEQ ID NO 460
<211> LENGTH: 300
<212> TYPE: DNA
<213> ORGANISM: Rattus norvegicus
<220> FEATURE:
<221> NAME/KEY: unsure
<222> LOCATION: (1)..(300)
<223> OTHER INFORMATION: unsure at all n locations

<400> SEQUENCE: 460
atctggccat aatttaattc catctctagg ttttctgtct tattgtttca gaggcacatc      60
gagaaccaac catgggcagc tttactaagg aagagttgac tgccatatcc tcgatgaagg     120
```

```
nttcactgct aaggacattc tggaccaaaa aatcaatgaa gttctcctct gatgataagg    180
atgctttcta tgttgcggac ctcggagacg ttctaaagaa gcatctgagg tggctgaaag    240
tcttccccgt gtactccctt ctagctgtca gtgtatgaca gcgagccata gtgagcacct    300
```

<210> SEQ ID NO 461
<211> LENGTH: 121
<212> TYPE: DNA
<213> ORGANISM: Rattus norvegicus
<220> FEATURE:
<221> NAME/KEY: unsure
<222> LOCATION: (1)..(121)
<223> OTHER INFORMATION: unsure at all n locations

<400> SEQUENCE: 461

```
cngctccgct cgctctcgaa cctcngtctt cagctcactg ccttcactcc agacttcacc    60
atgtccgtca gggtgacnca gaaatcctan aagangtcca cctcnggtcc ccgggacttc    120
a                                                                  121
```

<210> SEQ ID NO 462
<211> LENGTH: 133
<212> TYPE: DNA
<213> ORGANISM: Rattus norvegicus
<220> FEATURE:
<221> NAME/KEY: unsure
<222> LOCATION: (1)..(133)
<223> OTHER INFORMATION: unsure at all n locations

<400> SEQUENCE: 462

```
cggggatccg agttgcagac nacgtgngtg cncangagcc acctcnggag tttgaaccan    60 gaccctata actccnnnag gctgtcctca gcttgngnac agcctnagcc actccaaant    120
tngatcaaac gtt                                                     133
```

<210> SEQ ID NO 463
<211> LENGTH: 281
<212> TYPE: DNA
<213> ORGANISM: Rattus norvegicus
<220> FEATURE:
<221> NAME/KEY: unsure
<222> LOCATION: (1)..(281)
<223> OTHER INFORMATION: unsure at all n locations

<400> SEQUENCE: 463

```
cnggcggcgg acgacgttcg tcatttggtg cgggagggng cgcgagangg tgcgtcgagc    60
ctccggtgtc ccaaactaga ggtgagcatg gcagaacagg aacccactgc tgagcagctc    120
gctcagatag ctggagagaa tgaggaagac gagcactctg tgaactacaa gcctccagcc    180
cagaagagca tccaggagat ccaggaactg gacaaggatg atgaaagcct tcgaaagtac    240
aaggnggccc tgctgggccg agtagctgtc tctgcagacc c                      281
```

<210> SEQ ID NO 464
<211> LENGTH: 264
<212> TYPE: DNA
<213> ORGANISM: Rattus norvegicus
<220> FEATURE:
<221> NAME/KEY: unsure
<222> LOCATION: (1)..(264)
<223> OTHER INFORMATION: unsure at all n locations

<400> SEQUENCE: 464

```
gctccggggng cnctgcgcgc cgnggngttc tgtgncttgc nggtctgttc cctccgattg    60
```

```
tgcctancaa tgaccaccca gcagantgtt ctccagggcc cgggacccng gggtttccga      120
ntcgtgggcg gcaaggactt tgagcaacct ctcgccattt cccgggtcac tcccgggagc      180
aaggntgnta tagctaactt atgcatagga gatttnatca cagccattga tggggnagat      240
accancagta tgacaaatnn gaag                                             264
```

```
<210> SEQ ID NO 465
<211> LENGTH: 277
<212> TYPE: DNA
<213> ORGANISM: Rattus norvegicus
<220> FEATURE:
<221> NAME/KEY: unsure
<222> LOCATION: (1)..(277)
<223> OTHER INFORMATION: unsure at all n locations

<400> SEQUENCE: 465
gcttctaggg aggctctctg caataggtgc ccggcccagc ttttttttca aaatgtctac      60
tgtccacgaa atcctgtgca acnctcagct tggaggtga tcattctaca cccccaagtg      120
ccnatgggtc ggtcaaaccc tacaccaact tcgacgntga gagggatgct ttgaacattg      180
aaacagcaat caagaccaaa ggcgtggacg aggtcaccat tgtcaacatt ctgactaacc      240
gcagcaatgc acagaggcag gacattgcct tcgccta                              277
```

```
<210> SEQ ID NO 466
<211> LENGTH: 249
<212> TYPE: DNA
<213> ORGANISM: Rattus norvegicus
<220> FEATURE:
<221> NAME/KEY: unsure
<222> LOCATION: (1)..(249)
<223> OTHER INFORMATION: unsure at all n locations

<400> SEQUENCE: 466
tgggatcccc aggggctaat ggcatcctg ttcttgcagc agggnactgt gagaaagtct       60
ctcaccgtga ccaagtttct ctgagtgtcc agccaaccca ggctcaccag ctccctcnag     120
ctaccgcncg tccatcaggt caactgccaa ccccaggctg aanaccaaac ccagctatga     180
gctcctggag gcatgactcc ctcagggcca gcagctccga tccctcccag tagtgatcat     240 gggcnaggg                                                             249
```

```
<210> SEQ ID NO 467
<211> LENGTH: 253
<212> TYPE: DNA
<213> ORGANISM: Rattus norvegicus
<220> FEATURE:
<221> NAME/KEY: unsure
<222> LOCATION: (1)..(253)
<223> OTHER INFORMATION: unsure at all n locations

<400> SEQUENCE: 467
tacacgccgc cgcttgtncc gccgccatgt ccctagtgat ccccgagaag tttcagcaca     60
tcctgcgagt actccaacac caacatcgat gggcggcgga aaatagcctt cgctatcact    120
gccattaagg ttctggccaa cggtctagac aacaagctgc gtgaggacct ggagcggctg    180
aagaaaatcc gagcccatag agggctgcgc cactttggg gccttcgtgt ccggggtcag     240
cacaccaaga cat                                                        253
```

```
<210> SEQ ID NO 468
<211> LENGTH: 301
<212> TYPE: DNA
<213> ORGANISM: Rattus norvegicus
```

```
<220> FEATURE:
<221> NAME/KEY: unsure
<222> LOCATION: (1)..(301)
<223> OTHER INFORMATION: unsure at all n locations

<400> SEQUENCE: 468
gctttctatg ttgcggacct cggagacgtt ctaaagaagc atctgaggtg gctganagta      60
cttccccgtg ttactcccct ctatgctgtc aagtgtaatg acagcagagc catagtgagc     120
accctggctg ccattgggac aggatttgat tgtgcaagca agactgaaat acagttggtg     180
caggggcttg gggtgcctcc agagaggatt atctatgcaa atccttgtaa gcnagtgtct     240
cagatcaagt atgctgccag taatggagtc cagatgatga cttttgacag tgaaattgag     300
t                                                                    301

<210> SEQ ID NO 469
<211> LENGTH: 136
<212> TYPE: DNA
<213> ORGANISM: Rattus norvegicus
<220> FEATURE:
<221> NAME/KEY: unsure
<222> LOCATION: (1)..(136)
<223> OTHER INFORMATION: unsure at all n locations

<400> SEQUENCE: 469
ttccggcgga ggccgctctt tcttttctc cgcagggtgc gcggtggcag ccgctgcggt       60
gcttggctcc ctaagctatc cggtgccatc cttgtcgntg cggcgacact cgcaacatct    120
gcagccatga ccgagc                                                    136

<210> SEQ ID NO 470
<211> LENGTH: 147
<212> TYPE: DNA
<213> ORGANISM: Rattus norvegicus
<220> FEATURE:
<221> NAME/KEY: unsure
<222> LOCATION: (1)..(147)
<223> OTHER INFORMATION: unsure at all n locations

<400> SEQUENCE: 470
attaaggaaa atggaggtct ggactcagag gaagtcttat cccnatgaag caaaaggatg      60
gatcnttgta aatacagagc tgagtatgnc tngtggctaa acgancacag ggtntgtggt    120
atcccctcng caaagagtna ngccttc                                        147

<210> SEQ ID NO 471
<211> LENGTH: 294
<212> TYPE: DNA
<213> ORGANISM: Rattus norvegicus
<220> FEATURE:
<221> NAME/KEY: unsure
<222> LOCATION: (1)..(294)
<223> OTHER INFORMATION: unsure at all n locations

<400> SEQUENCE: 471
gctaccagga cagctcatca tgtggggaga aatgttgggc gctgctatag gaggagttgt      60
ggctgtncgc agctgcaccc gnccgtcctg tctgccgtgg gcttcactgg gtcaggcatt    120
ggcagctgca tcccatagcg ggncaagatg atgtctgctg cagcagttgc caacgggggc    180
ggagtcgncn caggaagcct tggtagccan actacagtcc antangtgta tttggnnttn    240
tccaacatna ancaacnatc catcttgggg tcttttggng naanccatna gagt          294

<210> SEQ ID NO 472
```

<211> LENGTH: 300
<212> TYPE: DNA
<213> ORGANISM: Rattus norvegicus
<220> FEATURE:
<221> NAME/KEY: unsure
<222> LOCATION: (1)..(300)
<223> OTHER INFORMATION: unsure at all n locations

<400> SEQUENCE: 472

| attccagcga gagacagagg gagtgagcgg gcgggttgga agagcccagt gtgcagagcc | 60 |
| ccactccggg cttcctagga aggcagctct ggagtgagaa gggctttgcc tccaggcttg | 120 |
| ctgcctcctc gacccaatcc tcccgctgac ccaacatcag cggtcgcaac cctcgccgcc | 180 |
| tctgggaaac tttgcccatt gcaacgggca gacacttctc actggaactt acaatctgcg | 240 |
| agccaggaca ggatccccag gcgcagggan ggaattttgt ctattgggac agtgttctct | 300 |

<210> SEQ ID NO 473
<211> LENGTH: 276
<212> TYPE: DNA
<213> ORGANISM: Rattus norvegicus

<400> SEQUENCE: 473

| gtccctcagc agtcctggat tcagaatgga accatcaaag acaacatcct gtttgggtcc | 60 |
| gaatacaatg aaaagaagta ccagcaagtt ctcaaagcat gcgctctcct cccagacttg | 120 |
| gaaatattgc ctggaggaga catggctgag atcggagaga aggggataaa tctcagtggt | 180 |
| ggtcagaagc agcgagtcag cctggccaga gctgcctatc aagatgctga catctatatt | 240 |
| ctggacgatc ccctgtcggc tgtggatgct catgtg | 276 |

<210> SEQ ID NO 474
<211> LENGTH: 155
<212> TYPE: DNA
<213> ORGANISM: Rattus norvegicus
<220> FEATURE:
<221> NAME/KEY: unsure
<222> LOCATION: (1)..(155)
<223> OTHER INFORMATION: unsure at all n locations

<400> SEQUENCE: 474

| aacagctctc tgacacctga gagggatcag ccagagtaag agtcgtgggc ttgattgtaa | 60 |
| catcagaata gcctaagagt gaagcaanca ctctgccatt acttgggant cttctgcctc | 120 |
| ccgtgtgaga ggatgtgtcg gagaggttca ccagc | 155 |

<210> SEQ ID NO 475
<211> LENGTH: 282
<212> TYPE: DNA
<213> ORGANISM: Rattus norvegicus
<220> FEATURE:
<221> NAME/KEY: unsure
<222> LOCATION: (1)..(282)
<223> OTHER INFORMATION: unsure at all n locations

<400> SEQUENCE: 475

| gggncggctt ggtggcctcn attgagatnc ngaggatcna aggactgtgt anctacaatg | 60 |
| ttgtcaagac ttttccgtat gtatggnctc tttgnggtgt ctcatncnng ggaggtaatt | 120 |
| gtgggaacgg tgacacttac tatctgtatg atgnccatga acatgttcac cggcaacaac | 180 |
| aagatctgtg gttggaatta tgagtgccca nnatttgaag angacgtgct gancagcgac | 240 |
| atcatcancc tcagganaan ccggtnatcg ccatccgtac at | 282 |

<210> SEQ ID NO 476
<211> LENGTH: 225
<212> TYPE: DNA
<213> ORGANISM: Rattus norvegicus
<220> FEATURE:
<221> NAME/KEY: unsure
<222> LOCATION: (1)..(225)
<223> OTHER INFORMATION: unsure at all n locations

<400> SEQUENCE: 476
ggcggctcgg actgagcagg gctttccttg ccagtggatt gtgtagagtg tacagccagt      60
ctcttgtctt ctgtccaaca tggcatcttc tgatattcag gtgaaatgct tccggccagg     120
ctttgagtga tccagcctcg atcaaaagaa ttgtcccgag tcccctttcc cccaaagaga     180
ggncttcctg agaatcagag aatagantga agaaaganct agaca                     225

<210> SEQ ID NO 477
<211> LENGTH: 296
<212> TYPE: DNA
<213> ORGANISM: Rattus norvegicus
<220> FEATURE:
<221> NAME/KEY: unsure
<222> LOCATION: (1)..(296)
<223> OTHER INFORMATION: unsure at all n locations

<400> SEQUENCE: 477
aggacaccga gattgagatc tcgcacnctt cactggtaga aagggaaatc aataaagccc      60
agaacttgat ngctggggaa gggttgaaga ttagctctga tctcattagc ttggaggtta    120
gctctccaca tgtcccagac ctnactctga ttgaccttcc tggtatcaca agagtggctg    180
tgggtgacca gcctgcagac atcgaacaca agatcaagan acttatcact gaatacatcc    240
agaaacagga gaccatcaac ctggtggtgg tccccagcaa tgtggcattg ccacca        296

<210> SEQ ID NO 478
<211> LENGTH: 294
<212> TYPE: DNA
<213> ORGANISM: Rattus norvegicus
<220> FEATURE:
<221> NAME/KEY: unsure
<222> LOCATION: (1)..(294)
<223> OTHER INFORMATION: unsure at all n locations

<400> SEQUENCE: 478
gacagcactc tgcatggctt agagagcagc tcccctctct ccccactgtc agccagtgcg      60
cagttcacct ctgtgggctg cggagcacct ctgccgcagc ccagacatct ccctgagca     120 gaggcagaac aagcataggc gctttcagaa taccctagcc gtcctccgga agtctggttt    180
gntgggaatc actctgaaag ccaaggagtt gattcgtcag aaccaagcaa ctnaggtgna    240
actggaccag ctgaaggagc aaaccagatg ttnatagagg ccaccaagac aggg          294

<210> SEQ ID NO 479
<211> LENGTH: 281
<212> TYPE: DNA
<213> ORGANISM: Rattus norvegicus
<220> FEATURE:
<221> NAME/KEY: unsure
<222> LOCATION: (1)..(281)
<223> OTHER INFORMATION: unsure at all n locations

<400> SEQUENCE: 479
aaatcctgac aaaagaatct aatgttcagg aggttcgatg tccagtcact gtgtgtggag      60
atgtgcatgg gcaatttcat gacctcatgg aactctttag aattggtggt aaatcacaga    120

```
tacaaattac ttgtttatgg gagactatgt ggacagagga tattactcag ttgaaacagt      180
tacactgctt gtagctctta aggttcgtta ccgagagcgt atcaccatac tccganggaa      240
tcacgagagc agacagatca cacaagttta tggtttctac g                         281
```

<210> SEQ ID NO 480
<211> LENGTH: 293
<212> TYPE: DNA
<213> ORGANISM: Rattus norvegicus
<220> FEATURE:
<221> NAME/KEY: unsure
<222> LOCATION: (1)..(293)
<223> OTHER INFORMATION: unsure at all n locations

<400> SEQUENCE: 480

```
ggcggagcag tcactgtttg angagctctg agcnctggca gctgcacact tcagttcacc      60
aacccaggag cttctctctct gnggaagggg tgganatagc tgtttaaaga cactgcaacc    120
agaaagccaa gcattctgtc actaagcagg anactgagtg cccacttgga agaagaaata    180
aaagatggtt cttagcacag aggaaaacag gagtgttgat ttagtcaact tacccagtgt    240
cccactgccc gatggagagg ctggcgtagg ggagaacaac gggattcctt gna           293
```

<210> SEQ ID NO 481
<211> LENGTH: 298
<212> TYPE: DNA
<213> ORGANISM: Rattus norvegicus
<220> FEATURE:
<221> NAME/KEY: unsure
<222> LOCATION: (1)..(298)
<223> OTHER INFORMATION: unsure at all n locations

<400> SEQUENCE: 481

```
ctccagctag ctcagtctca cagcctaagc ccttaaagcg tttcaaacga gctacaggga      60
agaaaggtcc ccgcacccgt caggggtctg gtgcagagtc tgaagncctg tatgactttg     120 ttttttattgt ggctggtgag aaataggatg gtgaagagat ggagattggg gaagtagctt   180
gcgggaactc tggatngatc aatncccagc tngtttgggg gttccnagcc anaagaggca    240
nncccagnng attcgnnaat ttgnncacnc ctggagctgt cnacaattcc tcttccnc      298
```

<210> SEQ ID NO 482
<211> LENGTH: 65
<212> TYPE: DNA
<213> ORGANISM: Rattus norvegicus
<220> FEATURE:
<221> NAME/KEY: unsure
<222> LOCATION: (1)..(65)
<223> OTHER INFORMATION: unsure at all n locations

<400> SEQUENCE: 482

```
ggtgangtga agctgctaaa ccccatttg gctgctgctg tggagatgct gtgctttgag       60 agtna                                                                  65
```

<210> SEQ ID NO 483
<211> LENGTH: 270
<212> TYPE: DNA
<213> ORGANISM: Rattus norvegicus
<220> FEATURE:
<221> NAME/KEY: unsure
<222> LOCATION: (1)..(270)
<223> OTHER INFORMATION: unsure at all n locations

<400> SEQUENCE: 483

```
ggccggccgt gaggngcgct ggagctgccg gtactggttt tggattagga atggttttct      60
```

```
ccctcacctt ctttaagaga agaaagtggc cattagcctt tggttctggc gtgggactgg    120
ggatggccta ctccaactgt cagcatgact ttcaggctcc atatcttcta catggaaaat    180
atgtcaaaga gcagtgactt atgctangaa catcccagcg ggagaaaaga gaagcctcgt    240
ttattcctca ggaatactga agtgccctgg                                     270

<210> SEQ ID NO 484
<211> LENGTH: 277
<212> TYPE: DNA
<213> ORGANISM: Rattus norvegicus
<220> FEATURE:
<221> NAME/KEY: unsure
<222> LOCATION: (1)..(277)
<223> OTHER INFORMATION: unsure at all n locations

<400> SEQUENCE: 484
gggaagctac ctatccggta gacagctccc cctgcaccta cggctgccat gacttccgca    60
ctgacccaag ggctggaacg aatcccagac cagcttggct acctggtgct gagcgaaggt   120
gcagtgctag cgtcatctgg ggatcttgag aacgatgagc aggcagccag cgccatctna   180
gagctggtca gcacagcctg tgcttccgg ctgcaccatg gcacgaacat cccttttcaag  240 cgcctgtctg tggtctttgg tgaacacacg ctgctgg                            277

<210> SEQ ID NO 485
<211> LENGTH: 279
<212> TYPE: DNA
<213> ORGANISM: Rattus norvegicus
<220> FEATURE:
<221> NAME/KEY: unsure
<222> LOCATION: (1)..(279)
<223> OTHER INFORMATION: unsure at all n locations

<400> SEQUENCE: 485
caatgactca cagcgacagg gccactaagg atgctggcca gatatctggg ctaaatgtgc    60
tccgagtgat caacgagcct acagctgcag ctctggctta cggtctggac aaatccgaag   120
acaaagtcat tgctgtatat gatttaggtg gaggaaccct tgacatttct atcctggaaa   180
ttcagaaagg agtgtttnan gtgaaatcca ccaatgggga cactttctta ggaggtgaag   240
actttgacca gctttgttta cggcacattg tcaaggagt                          279

<210> SEQ ID NO 486
<211> LENGTH: 204
<212> TYPE: DNA
<213> ORGANISM: Rattus norvegicus
<220> FEATURE:
<221> NAME/KEY: unsure
<222> LOCATION: (1)..(204)
<223> OTHER INFORMATION: unsure at all n locations

<400> SEQUENCE: 486
ggggttacnn cttgcagtcn gtccgctgtt tgcaaatatt gcgtgggctc ngcgcgctgc    60
gggctgcggg anggtccgga cccggcgtcc gattgcagcg ccatccagtt tgcatgaaac   120
tttcacctgc gctcccggga acagtttctg ctccgactcc tgatcgttca cctccctgtt   180
ttcccgacag cggggactgt cttt                                          204

<210> SEQ ID NO 487
<211> LENGTH: 290
<212> TYPE: DNA
<213> ORGANISM: Rattus norvegicus
<220> FEATURE:
```

```
<221> NAME/KEY: unsure
<222> LOCATION: (1)..(290)
<223> OTHER INFORMATION: unsure at all n locations

<400> SEQUENCE: 487
gccgcccgcc tcggacgctt ggnactgtcg cgtctgtgtc gcctgtcgcc catcgcctgc     60
cgccgctgcc acccaccagc aaccatgagc gcgcccggcc ccgtgtagt ctgctgtcct    120 ctagattagt gctctcctcc gcgacggtcc gcagcatgga gtcgcccgcc gccagcccgc    180
cggccagctt gcctcagacc aaaggaaaat ccaaaaggaa aagggattta cgaatatcct    240
gtgtgtccaa gccacccgtg tccaaccccca caccccccgg aaactggact              290

<210> SEQ ID NO 488
<211> LENGTH: 166
<212> TYPE: DNA
<213> ORGANISM: Rattus norvegicus
<220> FEATURE:
<221> NAME/KEY: unsure
<222> LOCATION: (1)..(166)
<223> OTHER INFORMATION: unsure at all n locations

<400> SEQUENCE: 488
gacagccata catgacacca agccattggt tctgagtttt cctttgtcca gtcggcttta     60
cgtctgtgtc caggtcggtc tggctgtcca tcagctctcg tcatngggag agtcagcttc    120
ccggaggttt tggttgatgg gcgcttggca ggtngctgtt ggggaa                   166

<210> SEQ ID NO 489
<211> LENGTH: 262
<212> TYPE: DNA
<213> ORGANISM: Rattus norvegicus

<400> SEQUENCE: 489
gtggaagaaa gaacacagca agaatggaaa actttgcacc tggctttcag gttggagatg     60
gaattggaat ggatttaaaa ctatccaacc acgttttaa tgctttaaaa caacatgcct    120
actcggaaga acgtcgaagt gcccgtctcc atgagaagaa ggaacattcc accgctgaaa    180
aagcagttga tcctaagaca cgcttactta tgtataaaat ggtcaactct ggaatgttgg    240
agacaatcac tggctgtatt ag                                            262

<210> SEQ ID NO 490
<211> LENGTH: 25
<212> TYPE: DNA
<213> ORGANISM: Rattus norvegicus

<400> SEQUENCE: 490
ctctcctcct cattcaacac cttcg                                           25

<210> SEQ ID NO 491
<211> LENGTH: 21
<212> TYPE: DNA
<213> ORGANISM: Rattus norvegicus

<400> SEQUENCE: 491
ctgaagcctc taaagtctac a                                               21

<210> SEQ ID NO 492
<211> LENGTH: 22
<212> TYPE: DNA
<213> ORGANISM: Rattus norvegicus

<400> SEQUENCE: 492
```

```
ctctgtctgc catccctccc ac                                         22
```

<210> SEQ ID NO 493
<211> LENGTH: 27
<212> TYPE: DNA
<213> ORGANISM: Rattus norvegicus

<400> SEQUENCE: 493

```
ctcacctcag atcctttgtg tgtctgg                                    27
```

<210> SEQ ID NO 494
<211> LENGTH: 25
<212> TYPE: DNA
<213> ORGANISM: Rattus norvegicus

<400> SEQUENCE: 494

```
tccgatcata cctagtagtt tgagc                                      25
```

<210> SEQ ID NO 495
<211> LENGTH: 25
<212> TYPE: DNA
<213> ORGANISM: Rattus norvegicus

<400> SEQUENCE: 495

```
ccttcatttg ctgctggtag tgctc                                      25
```

<210> SEQ ID NO 496
<211> LENGTH: 26
<212> TYPE: DNA
<213> ORGANISM: Rattus norvegicus

<400> SEQUENCE: 496

```
cctactgtgg atgataccag tgctgc                                     26
```

<210> SEQ ID NO 497
<211> LENGTH: 25
<212> TYPE: DNA
<213> ORGANISM: Rattus norvegicus

<400> SEQUENCE: 497

```
tcgccatcct ctggcgtttt gtagg                                      25
```

<210> SEQ ID NO 498
<211> LENGTH: 24
<212> TYPE: DNA
<213> ORGANISM: Rattus norvegicus

<400> SEQUENCE: 498

```
tcccttctca tgctgttgtg gctc                                       24
```

<210> SEQ ID NO 499
<211> LENGTH: 27
<212> TYPE: DNA
<213> ORGANISM: Rattus norvegicus

<400> SEQUENCE: 499

```
ctctcctgct tctgatgaag tacccac                                    27
```

<210> SEQ ID NO 500
<211> LENGTH: 23
<212> TYPE: DNA
<213> ORGANISM: Rattus norvegicus -continued

```
<400> SEQUENCE: 500
cctctcactg ctcttcacat ggc                                           23

<210> SEQ ID NO 501
<211> LENGTH: 27
<212> TYPE: DNA
<213> ORGANISM: Rattus norvegicus

<400> SEQUENCE: 501
cactattctt gtcaaatggc taccca                                        27

<210> SEQ ID NO 502
<211> LENGTH: 24
<212> TYPE: DNA
<213> ORGANISM: Rattus norvegicus

<400> SEQUENCE: 502
ccttgtaaat gccagataac gcca                                          24

<210> SEQ ID NO 503
<211> LENGTH: 22
<212> TYPE: DNA
<213> ORGANISM: Rattus norvegicus

<400> SEQUENCE: 503
ctccacatag gcgggaaatt gc                                            22

<210> SEQ ID NO 504
<211> LENGTH: 25
<212> TYPE: DNA
<213> ORGANISM: Rattus norvegicus

<400> SEQUENCE: 504
cctcatagat gccatttgtt ccacc                                         25

<210> SEQ ID NO 505
<211> LENGTH: 24
<212> TYPE: DNA
<213> ORGANISM: Rattus norvegicus

<400> SEQUENCE: 505
catcctccca ttcattatcg ccgc                                          24

<210> SEQ ID NO 506
<211> LENGTH: 22
<212> TYPE: DNA
<213> ORGANISM: Rattus norvegicus

<400> SEQUENCE: 506
cacgtccctc attgctcttc ag                                            22

<210> SEQ ID NO 507
<211> LENGTH: 25
<212> TYPE: DNA
<213> ORGANISM: Rattus norvegicus

<400> SEQUENCE: 507
ccgatccctg tcctcccac cgtgc                                          25

<210> SEQ ID NO 508
<211> LENGTH: 24
<212> TYPE: DNA
<213> ORGANISM: Rattus norvegicus
```

```
<400> SEQUENCE: 508
ccaagactga tcgctgtctc cagg                                              24

<210> SEQ ID NO 509
<211> LENGTH: 25
<212> TYPE: DNA
<213> ORGANISM: Rattus norvegicus

<400> SEQUENCE: 509
ctgccctact taattgatgg atcgc                                             25

<210> SEQ ID NO 510
<211> LENGTH: 29
<212> TYPE: DNA
<213> ORGANISM: Rattus norvegicus

<400> SEQUENCE: 510
cctctgcttc taccgtctta ccatctgga                                         29

<210> SEQ ID NO 511
<211> LENGTH: 27
<212> TYPE: DNA
<213> ORGANISM: Rattus norvegicus

<400> SEQUENCE: 511
ccaaagtctc cgatcttcac ttgatgc                                           27

<210> SEQ ID NO 512
<211> LENGTH: 28
<212> TYPE: DNA
<213> ORGANISM: Rattus norvegicus

<400> SEQUENCE: 512
cccgttctca gttcagtggt gtgctcct                                          28

<210> SEQ ID NO 513
<211> LENGTH: 24
<212> TYPE: DNA
<213> ORGANISM: Rattus norvegicus

<400> SEQUENCE: 513
cctccgccgc cgagccgact tcct                                              24

<210> SEQ ID NO 514
<211> LENGTH: 27
<212> TYPE: DNA
<213> ORGANISM: Rattus norvegicus

<400> SEQUENCE: 514
cctctcacca ttacttcttc cctgtca                                           27

<210> SEQ ID NO 515
<211> LENGTH: 27
<212> TYPE: DNA
<213> ORGANISM: Rattus norvegicus

<400> SEQUENCE: 515
cccatcatca gcaagaatcc caaaggc                                           27

<210> SEQ ID NO 516
<211> LENGTH: 22
<212> TYPE: DNA
```

```
<213> ORGANISM: Rattus norvegicus

<400> SEQUENCE: 516
ctctatgaca ttgagcaaca gc                                        22

<210> SEQ ID NO 517
<211> LENGTH: 20
<212> TYPE: DNA
<213> ORGANISM: Rattus norvegicus

<400> SEQUENCE: 517
catctacgac tgtgtcccgt                                           20

<210> SEQ ID NO 518
<211> LENGTH: 26
<212> TYPE: DNA
<213> ORGANISM: Rattus norvegicus

<400> SEQUENCE: 518
ccagagtctt gttgacttac aaccac                                    26

<210> SEQ ID NO 519
<211> LENGTH: 21
<212> TYPE: DNA
<213> ORGANISM: Rattus norvegicus

<400> SEQUENCE: 519
gagcatcttt caggtggttg g                                         21

<210> SEQ ID NO 520
<211> LENGTH: 20
<212> TYPE: DNA
<213> ORGANISM: Rattus norvegicus

<400> SEQUENCE: 520
gtgcttagaa cactttccag                                           20

<210> SEQ ID NO 521
<211> LENGTH: 20
<212> TYPE: DNA
<213> ORGANISM: Rattus norvegicus

<400> SEQUENCE: 521
ctggaaaagc atcggttgag                                           20

<210> SEQ ID NO 522
<211> LENGTH: 23
<212> TYPE: DNA
<213> ORGANISM: Rattus norvegicus

<400> SEQUENCE: 522
tcactgtcca tgatggtgtg cag                                       23

<210> SEQ ID NO 523
<211> LENGTH: 21
<212> TYPE: DNA
<213> ORGANISM: Rattus norvegicus

<400> SEQUENCE: 523
tggcatgtca caccagatgt a                                         21

<210> SEQ ID NO 524
<211> LENGTH: 22
```

```
<212> TYPE: DNA
<213> ORGANISM: Rattus norvegicus

<400> SEQUENCE: 524
ggagactact ccaatttcag ac                                      22

<210> SEQ ID NO 525
<211> LENGTH: 24
<212> TYPE: DNA
<213> ORGANISM: Rattus norvegicus

<400> SEQUENCE: 525
tgagtcaagc ctagagtatc acag                                    24

<210> SEQ ID NO 526
<211> LENGTH: 22
<212> TYPE: DNA
<213> ORGANISM: Rattus norvegicus

<400> SEQUENCE: 526
agagcaccat cagctggaag gt                                      22

<210> SEQ ID NO 527
<211> LENGTH: 20
<212> TYPE: DNA
<213> ORGANISM: Rattus norvegicus

<400> SEQUENCE: 527
ccaagaggag agccgaacag                                         20

<210> SEQ ID NO 528
<211> LENGTH: 20
<212> TYPE: DNA
<213> ORGANISM: Rattus norvegicus

<400> SEQUENCE: 528
gcatctgtgt agggcatgtg                                         20

<210> SEQ ID NO 529
<211> LENGTH: 18
<212> TYPE: DNA
<213> ORGANISM: Rattus norvegicus

<400> SEQUENCE: 529
gccaccttgt ccacatcc                                           18

<210> SEQ ID NO 530
<211> LENGTH: 20
<212> TYPE: DNA
<213> ORGANISM: Rattus norvegicus

<400> SEQUENCE: 530
agtgtgtgat gaacgcccga                                         20

<210> SEQ ID NO 531
<211> LENGTH: 19
<212> TYPE: DNA
<213> ORGANISM: Rattus norvegicus

<400> SEQUENCE: 531
gagcggctaa agacggcac                                          19

<210> SEQ ID NO 532
```

```
<211> LENGTH: 17
<212> TYPE: DNA
<213> ORGANISM: Rattus norvegicus

<400> SEQUENCE: 532
cctgaacgcc tcacaga                                                  17

<210> SEQ ID NO 533
<211> LENGTH: 16
<212> TYPE: DNA
<213> ORGANISM: Rattus norvegicus

<400> SEQUENCE: 533
cgctggctca acacag                                                   16

<210> SEQ ID NO 534
<211> LENGTH: 19
<212> TYPE: DNA
<213> ORGANISM: Rattus norvegicus

<400> SEQUENCE: 534
ctcctttggc taccatgtg                                                19

<210> SEQ ID NO 535
<211> LENGTH: 18
<212> TYPE: DNA
<213> ORGANISM: Rattus norvegicus

<400> SEQUENCE: 535
cggagtttaa tcctgtgg                                                 18

<210> SEQ ID NO 536
<211> LENGTH: 18
<212> TYPE: DNA
<213> ORGANISM: Rattus norvegicus

<400> SEQUENCE: 536
gcgtccatta gcatctgc                                                 18

<210> SEQ ID NO 537
<211> LENGTH: 20
<212> TYPE: DNA
<213> ORGANISM: Rattus norvegicus

<400> SEQUENCE: 537
caccatgtac cgaggcacag                                               20

<210> SEQ ID NO 538
<211> LENGTH: 20
<212> TYPE: DNA
<213> ORGANISM: Rattus norvegicus

<400> SEQUENCE: 538
ctcagcacgg agtaatccag                                               20

<210> SEQ ID NO 539
<211> LENGTH: 20
<212> TYPE: DNA
<213> ORGANISM: Rattus norvegicus

<400> SEQUENCE: 539
ggtagcgcat tatggcattg                                               20
```

<210> SEQ ID NO 540
<211> LENGTH: 20
<212> TYPE: DNA
<213> ORGANISM: Rattus norvegicus

<400> SEQUENCE: 540
ctgtcctttc tggtacatgc                                           20

<210> SEQ ID NO 541
<211> LENGTH: 20
<212> TYPE: DNA
<213> ORGANISM: Rattus norvegicus

<400> SEQUENCE: 541
cggagcgtac cagaacactg                                           20

<210> SEQ ID NO 542
<211> LENGTH: 23
<212> TYPE: DNA
<213> ORGANISM: Rattus norvegicus

<400> SEQUENCE: 542
gagagacaca gccagaatac agc                                       23

<210> SEQ ID NO 543
<211> LENGTH: 20
<212> TYPE: DNA
<213> ORGANISM: Rattus norvegicus

<400> SEQUENCE: 543
gtcgcttacc catgatctca                                           20

<210> SEQ ID NO 544
<211> LENGTH: 19
<212> TYPE: DNA
<213> ORGANISM: Rattus norvegicus

<400> SEQUENCE: 544
acgggtgatg ggaatggtg                                            19

<210> SEQ ID NO 545
<211> LENGTH: 20
<212> TYPE: DNA
<213> ORGANISM: Rattus norvegicus

<400> SEQUENCE: 545
gcagtctatc tcaaccctgg                                           20

<210> SEQ ID NO 546
<211> LENGTH: 19
<212> TYPE: DNA
<213> ORGANISM: Rattus norvegicus

<400> SEQUENCE: 546
aaccatgatg agagagagc                                            19

<210> SEQ ID NO 547
<211> LENGTH: 18
<212> TYPE: DNA
<213> ORGANISM: Rattus norvegicus

<400> SEQUENCE: 547
tgtcgtcttc ggttagtc                                             18

```
<210> SEQ ID NO 548
<211> LENGTH: 22
<212> TYPE: DNA
<213> ORGANISM: Rattus norvegicus

<400> SEQUENCE: 548
tccttcaggt cactcccacc tt                                              22

<210> SEQ ID NO 549
<211> LENGTH: 17
<212> TYPE: DNA
<213> ORGANISM: Rattus norvegicus

<400> SEQUENCE: 549
ccaggaactt gttctgg                                                    17

<210> SEQ ID NO 550
<211> LENGTH: 22
<212> TYPE: DNA
<213> ORGANISM: Rattus norvegicus

<400> SEQUENCE: 550
ctcccaacta ctaccccaac ag                                              22

<210> SEQ ID NO 551
<211> LENGTH: 20
<212> TYPE: DNA
<213> ORGANISM: Rattus norvegicus

<400> SEQUENCE: 551
gtcctgtgtc aagaaaactg                                                 20

<210> SEQ ID NO 552
<211> LENGTH: 19
<212> TYPE: DNA
<213> ORGANISM: Rattus norvegicus

<400> SEQUENCE: 552
cctacatcct agcctctcc                                                  19

<210> SEQ ID NO 553
<211> LENGTH: 22
<212> TYPE: DNA
<213> ORGANISM: Rattus norvegicus

<400> SEQUENCE: 553
ctgaccatca ttccccagga cc                                              22

<210> SEQ ID NO 554
<211> LENGTH: 22
<212> TYPE: DNA
<213> ORGANISM: Rattus norvegicus

<400> SEQUENCE: 554
gtccagacct gattcagttc tc                                              22

<210> SEQ ID NO 555
<211> LENGTH: 23
<212> TYPE: DNA
<213> ORGANISM: Rattus norvegicus

<400> SEQUENCE: 555
cagcagagct agtagacaga atc                                             23
```

<210> SEQ ID NO 556
<211> LENGTH: 24
<212> TYPE: DNA
<213> ORGANISM: Rattus norvegicus

<400> SEQUENCE: 556
ccagacacat gctaacagga tcta                                              24

<210> SEQ ID NO 557
<211> LENGTH: 22
<212> TYPE: DNA
<213> ORGANISM: Rattus norvegicus

<400> SEQUENCE: 557
ggaacctcga tgtggctaag ct                                                22

<210> SEQ ID NO 558
<211> LENGTH: 22
<212> TYPE: DNA
<213> ORGANISM: Rattus norvegicus

<400> SEQUENCE: 558
tgccacagaa ggctgacagg ga                                                22

<210> SEQ ID NO 559
<211> LENGTH: 22
<212> TYPE: DNA
<213> ORGANISM: Rattus norvegicus

<400> SEQUENCE: 559
ggacagagac aatgagcaca ac                                                22

<210> SEQ ID NO 560
<211> LENGTH: 18
<212> TYPE: DNA
<213> ORGANISM: Rattus norvegicus

<400> SEQUENCE: 560
cacagtggtc gtcaagcc                                                     18

<210> SEQ ID NO 561
<211> LENGTH: 18
<212> TYPE: DNA
<213> ORGANISM: Rattus norvegicus

<400> SEQUENCE: 561
tcctcagacg ctcctgtg                                                     18

<210> SEQ ID NO 562
<211> LENGTH: 19
<212> TYPE: DNA
<213> ORGANISM: Rattus norvegicus

<400> SEQUENCE: 562
cctctaagga ttggtggag                                                    19

<210> SEQ ID NO 563
<211> LENGTH: 20
<212> TYPE: DNA
<213> ORGANISM: Rattus norvegicus

<400> SEQUENCE: 563

| | |
|---|---|
| atcccaactg ctatgacacc | 20 |

<210> SEQ ID NO 564
<211> LENGTH: 20
<212> TYPE: DNA
<213> ORGANISM: Rattus norvegicus

<400> SEQUENCE: 564

| | |
|---|---|
| ccaggctaga gactattctg | 20 |

<210> SEQ ID NO 565
<211> LENGTH: 19
<212> TYPE: DNA
<213> ORGANISM: Rattus norvegicus

<400> SEQUENCE: 565

| | |
|---|---|
| ccacagaagg ttgtatgga | 19 |

<210> SEQ ID NO 566
<211> LENGTH: 19
<212> TYPE: DNA
<213> ORGANISM: Rattus norvegicus

<400> SEQUENCE: 566

| | |
|---|---|
| tcgaatgact ctgaggagg | 19 |

<210> SEQ ID NO 567
<211> LENGTH: 18
<212> TYPE: DNA
<213> ORGANISM: Rattus norvegicus

<400> SEQUENCE: 567

| | |
|---|---|
| ggatacattg ccagcacg | 18 |

<210> SEQ ID NO 568
<211> LENGTH: 21
<212> TYPE: DNA
<213> ORGANISM: Rattus norvegicus

<400> SEQUENCE: 568

| | |
|---|---|
| cagagacagc catgatcttc g | 21 |

<210> SEQ ID NO 569
<211> LENGTH: 18
<212> TYPE: DNA
<213> ORGANISM: Rattus norvegicus

<400> SEQUENCE: 569

| | |
|---|---|
| gcaaaactat gtgtggca | 18 |

<210> SEQ ID NO 570
<211> LENGTH: 15
<212> TYPE: DNA
<213> ORGANISM: Rattus norvegicus

<400> SEQUENCE: 570

| | |
|---|---|
| ccgatccgcc tgctc | 15 |

<210> SEQ ID NO 571
<211> LENGTH: 19
<212> TYPE: DNA
<213> ORGANISM: Rattus norvegicus

<400> SEQUENCE: 571

| | |
|---|---|
| aggttatggc tcccttggc | 19 |

<210> SEQ ID NO 572
<211> LENGTH: 21
<212> TYPE: DNA
<213> ORGANISM: Rattus norvegicus

<400> SEQUENCE: 572

| | |
|---|---|
| tgccatccag atttgtaagg g | 21 |

<210> SEQ ID NO 573
<211> LENGTH: 21
<212> TYPE: DNA
<213> ORGANISM: Rattus norvegicus

<400> SEQUENCE: 573

| | |
|---|---|
| gctcttacac tcctttcgct g | 21 |

<210> SEQ ID NO 574
<211> LENGTH: 18
<212> TYPE: DNA
<213> ORGANISM: Rattus norvegicus

<400> SEQUENCE: 574

| | |
|---|---|
| gcttccactg tgccccac | 18 |

<210> SEQ ID NO 575
<211> LENGTH: 18
<212> TYPE: DNA
<213> ORGANISM: Rattus norvegicus

<400> SEQUENCE: 575

| | |
|---|---|
| cacggcaagc acgaagag | 18 |

<210> SEQ ID NO 576
<211> LENGTH: 21
<212> TYPE: DNA
<213> ORGANISM: Rattus norvegicus

<400> SEQUENCE: 576

| | |
|---|---|
| aggatgcttg tcagactctt c | 21 |

<210> SEQ ID NO 577
<211> LENGTH: 19
<212> TYPE: DNA
<213> ORGANISM: Rattus norvegicus

<400> SEQUENCE: 577

| | |
|---|---|
| gctatgctgt ttgccagtg | 19 |

<210> SEQ ID NO 578
<211> LENGTH: 18
<212> TYPE: DNA
<213> ORGANISM: Rattus norvegicus

<400> SEQUENCE: 578

| | |
|---|---|
| acgatgacga tgtctacc | 18 |

<210> SEQ ID NO 579
<211> LENGTH: 21
<212> TYPE: DNA
<213> ORGANISM: Rattus norvegicus

```
<400> SEQUENCE: 579
gagaagcagc agcacattgt g                                                  21

<210> SEQ ID NO 580
<211> LENGTH: 18
<212> TYPE: DNA
<213> ORGANISM: Rattus norvegicus

<400> SEQUENCE: 580
gatgatctgg agcagcag                                                      18
```